United States Patent
Aigner et al.

(10) Patent No.: US 9,956,199 B2
(45) Date of Patent: May 1, 2018

(54) CHROMANE-LIKE CYCLIC PRENYLFLAVONOIDS FOR THE MEDICAL INTERVENTION IN NEUROLOGICAL DISORDERS

(71) Applicants: Ludwig Aigner, Freilassing (DE); Sébastien Couillard-Despres, Wals-Siezenheim (AT)

(72) Inventors: Ludwig Aigner, Freilassing (DE); Eleni Priglinger, Leonding (AT); Sébastien Couillard-Despres, Wals-Siezenheim (AT); Francisco Javier Rivera, Valdivia (AT); Herbert Riepl, Dachau (DE); Corinna Urmann, Deggendorf (DE); Martin Biendl, Elsendorf (DE)

(73) Assignees: Ludwig Aigner, Freilassing (DE); Sébastien Couillard-Despres, Wals-Siezenheim (AT)

( * ) Notice: Subject to any disclaimer, the term of this patent is extended or adjusted under 35 U.S.C. 154(b) by 0 days. days.

(21) Appl. No.: 15/354,325

(22) Filed: Nov. 17, 2016

(65) Prior Publication Data
US 2017/0128411 A1 May 11, 2017

Related U.S. Application Data

(62) Division of application No. 14/127,029, filed as application No. PCT/EP2012/061524 on Jun. 15, 2012, now Pat. No. 9,527,860.

(30) Foreign Application Priority Data

Jun. 17, 2011 (EP) ..................... 11170298

(51) Int. Cl.
| | | |
|---|---|---|
| A61K 31/35 | (2006.01) | |
| A61K 31/352 | (2006.01) | |
| A61K 31/353 | (2006.01) | |
| A61K 31/36 | (2006.01) | |
| A61K 31/355 | (2006.01) | |

(52) U.S. Cl.
CPC .......... *A61K 31/352* (2013.01); *A61K 31/353* (2013.01); *A61K 31/355* (2013.01); *A61K 31/36* (2013.01); *A61K 31/35* (2013.01)

(58) Field of Classification Search
CPC ............................. A61K 31/35; A61K 31/353
USPC ....................................................... 514/456
See application file for complete search history.

(56) References Cited

U.S. PATENT DOCUMENTS

| 7,585,892 B2 | 9/2009 | Huang et al. |
| 7,736,677 B2 | 6/2010 | Tripp et al. |
| 9,527,860 B2 | 12/2016 | Aigner et al. |
| 2002/0040052 A1 | 4/2002 | Ito et al. |
| 2004/0063612 A1 | 4/2004 | Yalpani |
| 2005/0004046 A1 | 1/2005 | van Praag et al. |
| 2007/0281045 A1 | 12/2007 | Tripp et al. |

(Continued)

FOREIGN PATENT DOCUMENTS

| CN | 1772753 | 5/2006 |
| DE | 102 40 065 A1 | 3/2004 |
| EP | 1 415 657 A1 | 7/2002 |

(Continued)

OTHER PUBLICATIONS

Blasina, et al., "Differentiation induced by *Achyrocline satureioides* (Lam) infusion in PC12 cells," *Phytother. Res.*, 23(9):1263-9, 2009.

(Continued)

*Primary Examiner* — Kevin E Weddington
(74) *Attorney, Agent, or Firm* — Parker Highlander PLLC

(57) ABSTRACT

The present invention relates to certain chromane-like cyclic prenylflavonoids, in particular the compounds of formulae (I), (II) and (III) as described and defined herein, for use in the treatment or prevention of a neurological disorder, as well as their use in promoting neuronal differentiation, neurite outgrowth and neuroprotection.

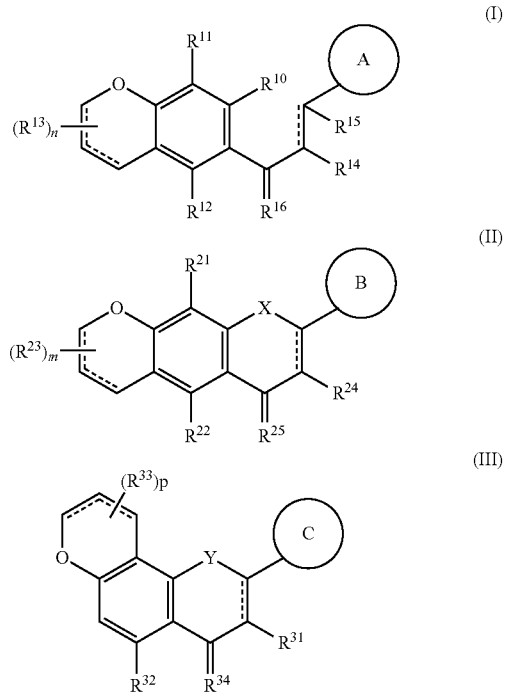

17 Claims, 37 Drawing Sheets

(56) References Cited

U.S. PATENT DOCUMENTS

Figure 1A:
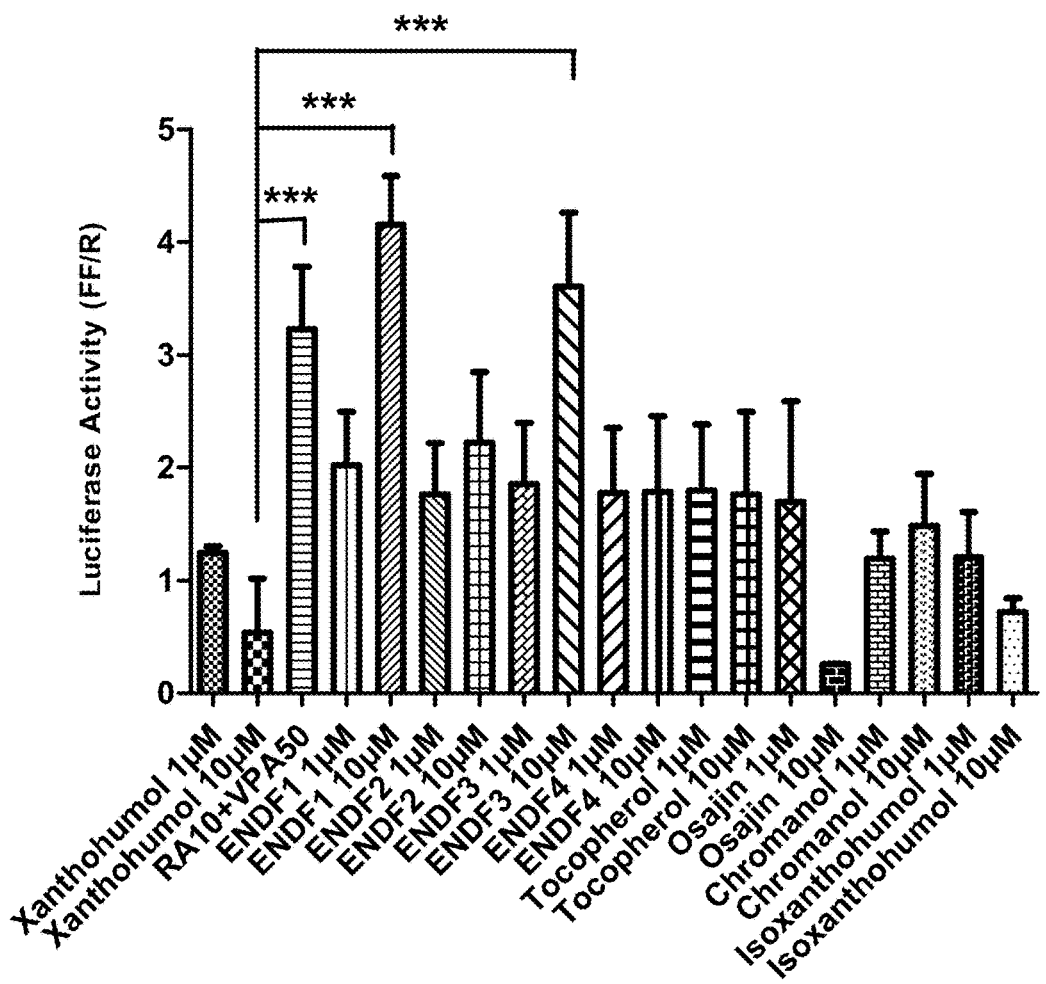

| | | |
|---|---|---|
| 2008/0031986 A1 | 2/2008 | Tripp et al. |
| 2009/0258094 A1 | 10/2009 | Ono et al. |

FOREIGN PATENT DOCUMENTS

| | | |
|---|---|---|
| IN | 921 CHE 2010 A | 10/2011 |
| KR | 10-0833652 | 5/2008 |
| KR | 2010037963 | 4/2010 |
| WO | WO 2000/012496 | 3/2000 |
| WO | WO 2003/031430 | 4/2003 |
| WO | WO 2004/007475 | 1/2004 |
| WO | WO 2007/016578 | 2/2007 |
| WO | WO 2007/067812 | 6/2007 |
| WO | WO 2007/149503 | 12/2007 |
| WO | WO 2008/095189 | 8/2008 |
| WO | WO 2008/147483 | 12/2008 |
| WO | WO 2009/130253 | 10/2009 |
| WO | WO 2010/006184 | 1/2010 |
| WO | WO 2010/128038 | 11/2010 |

OTHER PUBLICATIONS

Brattström, "Scientific evidence for a fixed extract combination (Ze 91019) from valerian and hops traditionally used as a sleep-inducing aid," *Wien Med Wochenschr*, 157(13-14):367-70, 2007.

Brunelli, et al., "8-Prenylnaringenin inhibits estrogen receptor-α mediated cell growth and induces apoptosis in MCF-7 breast cancer cells," *The Journal of Steroid Biochemistry and Molecular Biology*, 107(3-5):140-148, 2007.

Cho, et al., "Inhibition and structural reliability of prenylated flavones from the stem bark of *Morus ihou* on β-secretase (BACE-1)," *Bioorganic & Medicinal Chemistry Letters*, 21:2945-2948, 2011.

Choi, et al., "In vitro BACE-1 Inhibitory Phenolic Components from the Seeds of *Psoralea corylifolia*," *Planta Med*, 74:1405-1408, 2008.

Dajas, et al., "Neuroprotection by flavonoids," *Braz. J. Med. Biol. Res.*, 36(12):1613-20, 2003.

Dietz, et al, "Xanthohumol Isolated from *Humulus lupulus* Inhibits Menadione-Induced DNA Damage through Induction of Quinone Reductase," *Chem Res Toxicol.*, 18(8):1296-305, 2005.

Diller, et al. "Ability of Prenylflavanones Present in Hops to Induce Apoptosis in a Human Burkitt Lymphoma Cell Line," *Planta Medica*, 73(8):755-761, 2007.

Diller, et al. "Synthesis of Demethylxanthohumol, a New Potent Apoptosis-Inducing Agent from Hops," *Chemistry & Biodiversity*, 2(10):1331-1337, 2005.

Diopan, et al., "Electrochemical and Spectrometric Study of Antioxidant Activity of Pomiferin, Isopomiferin, Osajin, and Catalposide," *J Pharm Biomed Anal.*, 48(1):127-33, 2008.

Goto et al., "Enhanced antitumor activity of xanthohumol, a diacylglycerol acyltransferase inhibitor, under hypoxia," *Cancer Letters*, 219:215-222, 2005.

Gutierrez-Merino, et al., "Neuroprotective actions of flavonoids," *Curr. Med. Chem.* 18(8):1195-212, 2011.

Jang, et al., "A selective TrkB agonist with potent neurotrophic activities by 7,8-dihydroxyflavone," *Proc. Natl. Acad. Sci. USA*, 107(6):2687-92, 2010.

Jeon, et al., "Oroxylin A increases BDNF production by activation of MAPK-CREB pathway in rat primary cortical neuronal culture," *Neurosci. Res.*, 69(3):214-22, 2011.

Lee and Xia, "Concise total synthesis of biologically interesting pyranochalcone natural products: Citrunobin, boesenbergin A, boesenbergin B, xanthohumol C, and glabrachromene," *Synthesis*, (20):3240-3246, 2007.

Lee, et al.,"Oroxylin A, a Flavonoid, Stimulates Adult Neurogenesis in the Hippocampal Dentate Gyrus Region of Mice," *Neurochem Res.*, 35(11):1725-32, 2010.

Lee, et al., "Prenylflavones from *Psoralea corylifolia* Inhibit Nitric Oxide Synthase Expression through the Inhibition of I-κB-α Degradation in Activated Microglial Cells," *Biol. Pharm. Bull.*, 28(12):2253-2257, 2005.

Lee, et al., "Protection of Prenylated Flavonoids from *Mori cortex radicis* (Moraceae) against Nitric Oxide-induced Cell Death in Neuroblastoma SH-SY5Y Cells," *Arch. Pharm. Res.*, 35(1):163-170, 2012.

Li, et al., "Neuronal Differentiation of C17.2 Neural Stem Cells Induced by a Natural Flavonoid, Baicalin," *Chembiochem*, 12(3):449-56, 2011.

Lim, et al., "Wogonin induces differentiation and neurite outgrowth of neural precursor cells," *Biochem. Biophys. Res. Commun.*, 402(1):42-7, 2010.

Liu, et al., "Promotion of rat brain-derived progenitor cell neurogenesis by liquiritigenin treatment: Underlying mechanisms," *Neuroscience Letters*, 481(3):139-143, 2009.

Milligan, et al., "Identification of a potent phytoestrogen in hops (*Humulus lupulus* L.) and beer," *Journal of Clinical Endocrinology and Metabolism*, 84(6):2249-2252, 1999.

Miranda, et al., "Antiproliferative and cytotoxic effects of prenylated chalcones in human cancer cell lines and in cultured ret hepatocytes," *Food Chem. Toxicol.*, 37(4):271-85, 1999.

Miranda, et al., "Prenylated chalcones and flavanones as inducers of quinone reductase in mouse Hepa 1C1C7 cells," *Cancer Lett.* 149(1-2):21-9, 2000.

Office Action issued in U.S. Appl. No. 14/127,029, dated Aug. 17, 2015.

Office Action issued in U.S. Appl. No. 14/127,029, dated Jan. 8, 2016.

Office Action issued in U.S. Appl. No. 14/127,029, dated Jun. 10, 2016.

Page et al., "Procognitive compounds promote neurite outgrowth," *Pharmacology*, 96:131-136, 2015.

PCT International Search Report and Written Opinion issued in International Application No. PCT/EP2012/061524, dated Nov. 2, 2012.

Reznichenko, et al., "Green tea polyphenol (-)-epigallocatechin-3-gallate induces neurorescue of long-term serum-deprived PC12 cells and promotes neurite outgrowth," *J. Neurochem.*, 93(5):1157-67, 2005.

Sagara, et al., "Induction of PC12 cell differentiation by flavonoids is dependent upon extracellular sign-regulated kinase activation," *J. Neurochem.*, 90(5):1144-55, 2004.

Shiao, et al., "Neuroprotective Flavonoids from *Flemingia macrophylla*," *Planta Med.*, 71(9):835-40, 2005.

Valente, et al., "A diet enriched in polyphenols and polyunsaturated fatty acids, LMN diet, induces neurogenesis in the subventricular zone and hippocampus of adult mouse brain," *Journal of Alzheimer's Disease*, 18:849-865, 2009.

Vassar et al., "Function, therapeutic potential and cell biology of BACE proteases: current status and future prospects," *J Neurochem.*, 130(1):4-28, 2014.

Wilhelm and Wessjohann, "An efficient synthesis of the phytoestrogen 8-prenylnaringenin from xanthohumol by a novel demethylation process," *Tetrahedron*, 62(29):6961-6966, 2006.

Yan et al., "Can BACE1 inhibition mitigate early axonal pathology in neurological diseases?" *J Alzheimers Dis.*, 38(4):705-718, 2014.

Yao, et al., "Effects of Epimedium flavonoids on proliferation and differentiation of neural stem cells in vitro," *Neurol. Res.* 32(7):736-42, 2010.

CHROMANE-LIKE CYCLIC PRENYLFLAVONOIDS FOR THE MEDICAL INTERVENTION IN NEUROLOGICAL DISORDERS

This application is a divisional of U.S. application Ser. No. 14/127,029, filed Jul. 23, 2014, which is a national phase application under 35 U.S.C. § 371 of International Application No. PCT/EP2012/061524, filed Jun. 15, 2012, which claims priority to European Application No. 11170298.1, filed Jun. 17, 2011. The entire text of each of the above referenced disclosures is specifically incorporated herein by reference.

The present invention relates to certain chromane-like cyclic prenylflavonoids, including the compounds of formulae (I), (II) and (III) as described and defined herein, for use in the treatment or prevention of a neurological disorder, as well as their use in promoting neuronal differentiation, neurite outgrowth and neuroprotection.

Diseases of the central nervous system (CNS) are an assemblage of progressive neurological disorders accompanied with inexorable loss of neurons and axons for which there is currently no effective or intervening therapy. Previous pharmacological approaches were mostly unsuccessful due to no or very little efficacy, major side effects, and limited blood brain penetration of the tested molecules (Dziegielewska et al., 1979; Bauer & Bauer, 1998; Pardridge, 2001; Pardridge, 2002). The entry to the central nervous system across the blood brain barrier is tightly regulated by many factors such as molecular size, polarity, lipophilicity, hydrogen-bonding potential, etc. (Krämer et al., 2001; Tuszynski et al., 2005; Mensch et al., 2009).

The search for neuro-therapeutic agents is still ongoing. Initially, members of the neurotrophic factor family were quite promising. The first neurotrophin (nerve growth factor, NGF) was discovered in the 1950s followed by brain derived neurotrophic factor (BDNF), neurotrophin-3 (NT-3) and neurotrophin-4 (NT-4). Neurotrophines promote regeneration, growth, maintenance, and survival of neurons (Tuszynski 2005; Evans et al, 2008; Blesch & Tuszynski, 2009). Clinical trials with NGF or other neurotrophins however largely failed due to inefficacy or side effects. Also, clinical trials using small molecules with potential neuroprotective activity such as NMDA antagonists (Selfotel, Eliprodil, Aptiganel), ion channel blockers/agonists such as Nimodipine, Flunarizine, Fosphenytoin, Maxipost, or anti-inflammatory molecules such as aICAM, Enlimomab, LeukArrest, or radical scavenger molecules such as Tirilazad and Citicoline were either stopped due to side effects or did not show any efficacy.

Besides neuroprotection, the stimulation of adult neurogenesis might be an attractive approach for neuroregeneration and brain repair. The concept of neurogenesis dates back to the 20th century where Ramon y Cajal (1913) suggested that neurogenesis was a process of generating functionally integrated neurons from progenitors which occurred only during the development in the mammalian central nervous system (CNS) and ceased during the post developmental period. This concept of Ramon y Cajal was later challenged by the work of Josef Altman and G. Das (1962, 1969) who showed that the process of neurogenesis was conserved even in the adult mammalian CNS, while trying to perfect the technique of thymidine-H3 labelling as a marker for dividing cells. Much of the work was then carried out by Goldman (1999) who demonstrated and supported the fact of this ongoing process of neurogenesis in the adult human brain.

Further work done by Eriksson (1998) with the adult human hippocampus showed that neurogenesis occurred in human brains and that the human brain retains the potential for self-renewal throughout life.

Recent studies strongly support the fact that neurogenesis takes place specifically in the subventricular zone (SVZ) and the subgranular zone (SGZ) of the dentate gyrus in the hippocampus, and has been known to play a vital role in aging, pathologies and diverse cognitive functions (Gross, 2000; review by Ming & Song, 2005). Adult neurogenesis is influenced by various exogenous and endogenous factors. Physical exercise and enriched environment enhance adult neurogenesis. On the other hand, aging, stress or neurodegenerative diseases lead to a decline in adult neurogenesis. So far there is no promising treatment of such conditions available (Kuhn et al., 1996; Gould et al., 1997; Lie et al., 2004; Couillard-Despres et al., 2009).

It is therefore imperative to search for therapeutic agents that enhance neuronal differentiation, induce axonal growth and act neuroprotective to prevent and cure neurological disorders such as, e.g., trauma and peripheral nervous system disorders.

The officinal use of Hops (*Humulus lupulus* L.) as drug in folk medicine started probably with Mesue († 1015) although Hops is known because of its sedative character for centuries. Hops is a rich source of polyphenolics. Beside the α- and β-acids which are responsible for the worth preparation in brewing industry, especially prenylchalcones and prenylflavanones are an important group of compounds. Prenylflavonoids are distinguished from flavonoids by having a prenyl, geranyl or lavandulyl sidechain in common. So are prenylchalcones defined as having a prenyl, geranyl or lavandulyl side chain. The hop-chalcones can be transformed into flavanones or vice versa by ring closure or opening on treatment with acids or bases, also in living organisms. The most important chalcone so far is Xanthohumol. Xanthohumol is especially known because of its tumor-preventive or even cytotoxic effects in anti-cancer assays. Xanthohumol has been suggested to be used for treating various diseases, including cancer, dyslipidaemia, diabetes, atherosclerosis and neurodegenerative diseases (U.S. Pat. No. 7,736,677; US 2007/0281045; US 2009/0258094; WO 2007/067812; WO 2007/149503; WO 2008/095189). One important prenylflavanone is 8-Prenylnaringenin, the most potent phytoestrogen known to date (Milligan, S. R., Kalita J. C., et al. 1999 Journal of Clinical Endocrinology and Metabolism 84(6): 2249-2252). Prenylflavonoids from hops have furthermore been described to show anti-proliferative activity or induce quinone reductase in certain cancer cell lines (Miranda C L, et al. *Food Chem Toxicol.* 1999. 37(4):271-85; Miranda C. L., et al. *Cancer Lett.* 2000. 149(1-2):21-9; Dietz B. M., et al. *Chem Res Toxicol.* 2005. 18(8):1296-305; Diller, R. A., H. M. Riepl, et al. *Chemistry & Biodiversity* 2005 2(10): 1331-1337; Diller, R. A., H. M. Riepl, et al. *Planta Medica* 2007 73(8): 755-761).

Prenylflavonoids from hops have also been reported to inhibit the oxidation of low-density lipoprotein (LDL) which is considered to be involved in the development of atherosclerosis and cardiovascular disease (Miranda C L, et al. *J Agric Food Chem.* 2000. 48(9):3876-84; Rodriguez R J, et al. *Food Chem Toxicol.* 2001. 39(5):437-45; Stevens J F, et al. *Chem Res Toxicol.* 2003.16(10):1277-86). However, the anti-oxidative effect reported in these references does not allow to draw any conclusion as to the possible efficacy of these compounds in the treatment of neurological diseases.

Certain Isoflavonoids from *Flemingia macrophylla*, including osajin, have further been described to show neuroprotective activity (Shiao Y J, et al. *Planta Med.* 2005. 71(9):835-40). Flavonoids, not prenylflavonoids, from other plant sources have been reported to increase the neurogenesis in adult mammalian brain (Valente et al., 2009; Liu et al., 2009; Yao et al., 2010; Lee S et al., *Neurochem Res.* 2010. 35(11):1725-32).

Flavonoids and related compounds are also described in: Diopan V, et al. *J Pharm Biomed Anal.* 2008. 48(1):127-33; Li M, et al. *Chembiochem.* 2011. 12(3):449-56; Lim J S, et al. *Biochem Biophys Res Commun.* 2010. 402(1):42-7; Blasina M F, et al. *Phytother Res.* 2009. 23(9):1263-9; Jeon S J, et al. *Neurosci Res.* 2011. 69(3):214-22; Liu R T, et al. *Neurosci Lett.* 2010. 481(3):139-43; Sagara Y, et al. *J Neurochem.* 2004. 90(5):1144-55; Reznichenko L, et al. *J Neurochem.* 2005. 93(5):1157-67; Jang S W, et al. *Proc Natl Acad Sci USA.* 2010. 107(6):2687-92; U.S. Pat. No. 7,585, 892; US 2002/0040052; US 2005/0004046; EP-A-1415657; WO 00/12496; WO 03/031430; WO 2004/007475; WO 2008/147483; WO 2009/130253; and WO 2010/128038.

Nevertheless, there is an ongoing demand for further as well as improved means for treating or preventing neurological disorders.

The present invention solves the problem of providing therapeutic agents having an improved efficacy in the medical intervention of neurological disorders as compared to structurally related, known therapeutic agents such as xanthohumol or osajin. Surprisingly it was found that only chromane-like substances derived from prenylated chalcones or flavanones, also called pyranoflavonoids, show this enhanced effect.

Accordingly, the present invention provides a compound of the following formula (I), (II) or (III), or a pharmaceutically acceptable salt or solvate thereof, for use in the treatment or prevention of a neurological disorder.

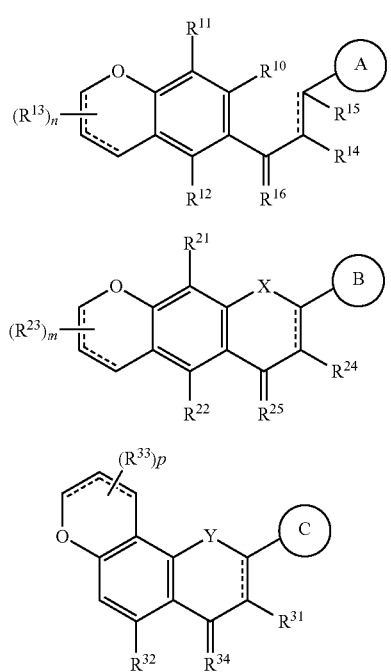

In formula (I), A is aryl or heteroaryl, wherein said aryl or said heteroaryl may be substituted with one or more groups independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O ($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH ($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N ($C_{1-6}$ alkyl)($C_{1-6}$ alkyl), halogen, —CF$_3$, or —CN.

$R^{10}$ is —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), hydrogen, or $C_{1-6}$ alkyl.

$R^{11}$ and $R^{12}$ are each independently selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O ($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH ($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N ($C_{1-6}$ alkyl)($C_{1-6}$ alkyl), halogen, —CF$_3$, or —CN.

Each $R^{13}$ is independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl) ($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN.

$R^{14}$ and $R^{15}$ are each independently selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O ($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH ($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N ($C_{1-6}$ alkyl)($C_{1-6}$ alkyl), halogen, —CF$_3$, or —CN.

$R^{16}$ is O, S or N(—OH).

n is 0, 1, 2 or 3.

Each ═══ in formula (I) is independently a single bond or a double bond, provided that at least one of the two adjacent bonds ═══ is a single bond.

In formula (II), B is aryl or heteroaryl, wherein said aryl or said heteroaryl may be substituted with one or more groups independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —$NH_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—$NH_2$, —CO—NH—($C_{1-6}$ alkyl), —CO—N($C_{1-6}$ alkyl)($C_{1-6}$ alkyl), —O—CO—$NH_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—$NH_2$, —N($C_{1-6}$ alkyl)-CO—$NH_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —$CF_3$, or —CN.

X is selected from O, S, N(H), N($C_{1-6}$ alkyl), or C(=N—OH).

$R^{21}$ and $R^{22}$ are each independently selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —$NH_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—$NH_2$, —CO—NH—($C_{1-6}$ alkyl), —CO—N($C_{1-6}$ alkyl)($C_{1-6}$ alkyl), —O—CO—$NH_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—$NH_2$, —N($C_{1-6}$ alkyl)-CO—$NH_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —$CF_3$, or —CN.

Each $R^{23}$ is independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —$NH_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—$NH_2$, —CO—NH—($C_{1-6}$ alkyl), —CO—N($C_{1-6}$ alkyl)($C_{1-5}$ alkyl), —O—CO—$NH_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—$NH_2$, —N($C_{1-6}$ alkyl)-CO—$NH_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —$CF_3$, or —CN.

$R^{24}$ is selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —$NH_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—$NH_2$, —CO—NH—($C_{1-6}$ alkyl), —CO—N($C_{1-6}$ alkyl)($C_{1-6}$ alkyl), —O—CO—$NH_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—$NH_2$, —N($C_{1-6}$ alkyl)-CO—$NH_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —$CF_3$, or —CN.

$R^{25}$ is O, S or N(—OH).

m is 0, 1, 2 or 3.

Each ═══ in formula (II) is independently a single bond or a double bond, provided that at least one of the two adjacent bonds ═══ is a single bond.

In formula (III), C is aryl or heteroaryl, wherein said aryl or said heteroaryl may be substituted with one or more groups independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —$NH_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—$NH_2$, —CO—NH—($C_{1-6}$ alkyl), —CO—N($C_{1-6}$ alkyl)($C_{1-6}$ alkyl), —O—CO—$NH_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—$NH_2$, —N($C_{1-6}$ alkyl)-CO—$NH_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —$CF_3$, or —CN.

Y is selected from O, S, N(H), N($C_{1-6}$ alkyl), or C(=N—OH).

$R^{31}$ is selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —$NH_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—$NH_2$, —CO—NH—($C_{1-6}$ alkyl), —CO—N($C_{1-6}$ alkyl)($C_{1-6}$ alkyl), —O—CO—$NH_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—$NH_2$, —N($C_{1-6}$ alkyl)-CO—$NH_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —$CF_3$, or —CN.

$R^{32}$ is selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —$NH_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—$NH_2$, —CO—NH—($C_{1-6}$ alkyl), —CO—N($C_{1-6}$ alkyl)($C_{1-6}$ alkyl), —O—CO—$NH_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—$NH_2$, —N($C_{1-6}$ alkyl)-CO—$NH_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —$CF_3$, or —CN.

Each $R^{33}$ is independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —$NH_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—$NH_2$, —CO—NH—($C_{1-6}$ alkyl), —CO—N($C_{1-6}$ alkyl)($C_{1-6}$ alkyl), —O—CO—$NH_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—$NH_2$, —N($C_{1-6}$ alkyl)-CO—$NH_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —$CF_3$, or —CN.

$R^{34}$ is O, S or N(—OH).

p is 0, 1, 2 or 3.

Each ==== in formula (III) is independently a single bond or a double bond, provided that at least one of the two adjacent bonds ==== is a single bond.

The present invention also relates to a pharmaceutical composition comprising a compound as described and defined herein, in particular a compound of formula (I), (II) or (III) or a pharmaceutically acceptable salt or solvate thereof, in combination with a pharmaceutically acceptable excipient for use in the treatment or prevention of a neurological disorder such as, e.g., stroke, an injury of the CNS or PNS, dementia, Alzheimer's disease and/or Alzheimer's dementia, or a psychiatric disorder.

Moreover, the invention is directed to a compound of formula (I), (II) or (III) or a pharmaceutically acceptable salt or solvate thereof, or a pharmaceutical composition comprising any of the aforementioned compounds and a pharmaceutically acceptable excipient, for use in promoting neuronal differentiation and/or neurite outgrowth.

The invention also encompasses a compound of formula (I), (II) or (III) or a pharmaceutically acceptable salt or solvate thereof, or a pharmaceutical composition comprising any of the aforementioned compounds and a pharmaceutically acceptable excipient, for use in the treatment or prevention of a neurological disorder by promoting neuronal differentiation and/or neurite outgrowth. In particular, the invention is directed to said compound or said pharmaceutical composition for use in the treatment or prevention of a neurological disorder by promoting neuronal sprouting.

Furthermore, the present invention relates to a method of treating or preventing a neurological disorder and/or a neurotraumatic event (such as, e.g., stroke, an injury of the CNS or PNS, dementia, Alzheimer's disease and/or Alzheimer's dementia, or a psychiatric disorder), the method comprising the administration of a compound of formula (I), (II) or (III) or a pharmaceutically acceptable salt or solvate thereof, or a pharmaceutical composition comprising any of the aforementioned compounds and a pharmaceutically acceptable excipient, to a subject (e.g., a human) in need of such treatment or prevention.

The invention also encompasses a method of promoting neuroprotection, promoting neuronal differentiation, and/or promoting neurite outgrowth in a subject (e.g., a human) in need of such treatment, the method comprising the administration of a compound of formula (I), (II) or (III) or a pharmaceutically acceptable salt or solvate thereof, or a pharmaceutical composition comprising any of the aforementioned compounds and a pharmaceutically acceptable excipient, to the subject.

Likewise, the invention includes a method of treating or preventing a neurological disorder and/or a neurotraumatic event by promoting neuronal differentiation and/or neurite outgrowth (in particular, by promoting neuronal sprouting), the method comprising the administration of a compound of formula (I), (II) or (III) or a pharmaceutically acceptable salt or solvate thereof, or a pharmaceutical composition comprising any of the aforementioned compounds and a pharmaceutically acceptable excipient, to a subject (e.g., a human) in need of such treatment or prevention.

In accordance with the present invention, it has been found that the chromane-like cyclic prenylflavonoids of the invention, in particular the compounds of formula (I), (II) or (III), are effective neuroprotective agents, promoting neuronal differentiation and neurite outgrowth, as has been demonstrated in Examples 17 to 20. In particular, it has surprisingly been found that the compounds of formula (I), (II) or (III) do not merely act as neuroprotective agents but promote neuronal sprouting. The compounds of the invention are thus useful in the treatment or prevention of a neurological disorder and/or a neurotraumatic event, in particular stroke, an injury of the central nervous system (CNS) or the peripheral nervous system (PNS), dementia, Alzheimer's disease and/or Alzheimer's dementia, or a psychiatric disorder.

The neurological disorder to be treated or prevented using a compound of the present invention, particularly a compound of formula (I), (II) or (III) as described and defined herein, may be, for example, Parkinson's disease, Alzheimer's disease and/or Alzheimer's dementia, amyotrophic lateral sclerosis (ALS) or any other motor neuron disorder, progressive supranuclear palsy, corticobasal degeneration, multiple system atrophy (i.e., multisystem-atrophy), spinocerebellar atrophy, Creutzfeld-Jacob disease, frontotemporal dementia (e.g., Pick's disease), dementia (e.g., HIV-related dementia, Lewy body dementia, vascular dementia, or multi-infarct dementia), Huntington's disease, Hallervorden Spatz disease, stroke, ischemia, an injury of the CNS or PNS (e.g., a spinal chord injury, a brain injury, a CNS trauma, or a peripheral nerves injury), hypoxia, epilepsy or seizures, concussion, multiple sclerosis, glaucoma, a tumorous disorder of the nervous system, a neural disorder caused by toxic insult, a neuro-ophthalmological disorder, a psychiatric disorder (e.g., depression, bipolar disorder, or schizophrenia), an age-related neurological loss or damage, retinitis pigmentosa, macular degeneration, a developmental disorder (e.g., Down's syndrome), or a neurological disorder caused by a developmental malformation, by a brain malformation or by a neural migration disorder.

It is particularly preferred that the neurological disorder to be treated or prevented using a compound of the invention is selected from stroke, an injury of the CNS or PNS (e.g., a spinal chord injury, a brain injury, a CNS trauma, or a peripheral nerves injury), dementia (e.g., HIV-related dementia, Lewy body dementia, vascular dementia, or multi-infarct dementia), Alzheimer's disease and/or Alzheimer's dementia, Parkinson's disease, depression, or a psychiatric disorder (e.g., depression, bipolar disorder, or schizophrenia), more preferably from stroke, an injury of the CNS or PNS (e.g., a spinal chord injury, a brain injury, a CNS trauma, or a peripheral nerves injury), dementia (e.g., HIV-related dementia, Lewy body dementia, vascular dementia, or multi-infarct dementia), Alzheimer's disease and/or Alzheimer's dementia, Parkinson's disease, or depression.

The compounds according to the present invention advantageously affect regeneration from damaged nerve fibers, as well as colateral sprouting from axons and the like, and dendritic plasticity, as also demonstrated in the examples. Accordingly, the compounds of the invention are furthermore useful in the treatment or amelioration of post-disease events, e.g., in rehabilitation.

It is also envisaged to use the compounds of the invention for treating or preventing epilepsy or seizures, including, without limitation, partial seizures (e.g., simple partial seizures, complex partial seizures, Jacksonian seizures, emporal lobe epilepsy, frontal lobe epilepsy, Rolandic epilepsy, or nocturnal epilepsy), generalized epilepsy (e.g., tonic-clonic seizures, absence seizures, atonic seizures, Lennox-Gastaut syndrome, or West syndrome), status epilepticus (e.g., epilepsia partialis continua or complex partial status epilepticus), or myoclonic epilepsy (e.g., juvenile myoclonic epilepsy; or progressive myoclonic epilepsy such as, e.g., dentatorubral-pallidoluysian atrophy, Unverricht-Lundborg disease, MERRF syndrome, or Lafora disease).

The efficacy of the compounds according to the invention, in particular the compounds of formula (I), (II) or (III), in promoting neuronal differentiation and also as neuroprotective agents has surprisingly been found to be considerably greater than that of, e.g., xanthohumol or osajin, as has been shown in Examples 17 and 20. The present invention thus provides compounds for the medical intervention of neurological disorders having an improved efficacy as compared to known therapeutic agents such as xanthohumol or osajin.

The compound of formula (I) will be described in more detail in the following.

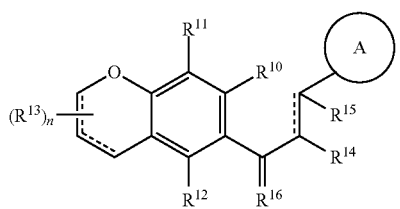

(I)

A is aryl or heteroaryl, wherein said aryl or said heteroaryl may be substituted with one or more groups (such as, e.g., one, two, three or four groups; preferably, one or two groups; more preferably, one group) independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN, preferably selected independently from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), halogen, —CF$_3$, or —CN, more preferably selected independently from $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, even more preferably selected independently from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, yet even more preferably selected independently from $C_{1-6}$ alkyl, —OH, —O($C_{1-6}$ alkyl), or halogen (e.g., —F, —Cl, —Br, or —I). Said aryl is preferably phenyl or naphthyl, more preferably said aryl is phenyl. Said heteroaryl is preferably 1,3-benzodioxolyl (e.g., 1,3-benzodioxol-5-yl or 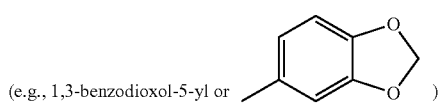 )

or a heteroaryl having 5 or 6 ring atoms, wherein 1, 2 or 3 of said ring atoms are heteroatoms independently selected from oxygen, sulfur or nitrogen, and the remaining ones of said ring atoms are carbon atoms. More preferably, said heteroaryl is selected from furanyl, thiophenyl (i.e., thienyl), pyrrolyl, imidazolyl, pyrazolyl, oxazolyl, isoxazolyl, furazanyl, thiazolyl, pyridinyl, pyrimidinyl, pyrazinyl, pyridazinyl, or 1,3-benzodioxolyl (e.g., 1,3-benzodioxol-5-yl). Even more preferably, said heteroaryl is selected from pyrrolyl, imidazolyl, pyridinyl, or pyrimidinyl. Most preferably, said heteroaryl is pyridinyl.

It is preferred that A is phenyl which may be substituted with one or more (e.g., one, two or three) groups independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN, preferably selected independently from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), halogen, —CF$_3$, or —CN, more preferably selected independently from $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, even more preferably selected independently from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, yet even more preferably selected independently from $C_{1-6}$ alkyl, —OH, —O($C_{1-6}$ alkyl), or halogen (e.g., —F, —Cl, —Br, or —I). More preferably, A is phenyl which may be substituted with one or two groups independently selected from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, preferably selected independently from $C_{1-6}$ alkyl, —OH, —O($C_{1-6}$ alkyl), or halogen. Even more preferably, A is phenyl which is unsubstituted or is substituted with one group (which is preferably in para-position) selected from $C_{1-6}$ alkyl, —OH, —O($C_{1-6}$ alkyl), or halogen. The present invention particularly relates to a compound of formula (I) or a pharmaceutically acceptable salt or solvate thereof, in which any one of the definitions of A, including any one of the preferred definitions of A described herein above, is combined with any of the definitions, including any of the preferred definitions, provided for each of the further groups and variables comprised in formula (I).

$R^{10}$ is —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), hydrogen, or $C_{1-6}$ alkyl. Preferably, $R^{10}$ is —OH, —O($C_{1-6}$ alkyl), —SH, or —S($C_{1-6}$ alkyl). More preferably, $R^{10}$ is —OH or —O($C_{1-6}$ alkyl). Even more preferably, $R^{10}$ is —OH or —OCH$_3$. Yet even more preferably, $R^{10}$ is —OCH$_3$. The present invention particularly relates to a compound of formula (I) or a pharmaceutically acceptable salt or solvate thereof, in which any one of the definitions of $R^{10}$, including any one of the preferred definitions of $R^{10}$ described herein above, is combined with any of the definitions, including any of the preferred definitions, provided for each of the further groups and variables comprised in formula (I).

$R^{11}$ and $R^{12}$ are each independently selected from hydrogen, $C_{1-6}$ alkyl, $C^{2-6}$ alkenyl, $C^{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN. Preferably, $R^{11}$ and $R^{12}$ are each independently selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), halogen, —CF$_3$, or —CN. More preferably, $R^{11}$ and $R^{12}$ are each independently selected from hydrogen, $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Even more preferably, $R^{11}$ and $R^{12}$ are each independently selected from hydrogen, $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Yet even more preferably, $R^{11}$ and $R^{12}$ are each independently selected from hydrogen, $C_{1-6}$ alkyl, —OH, —O($C_{1-6}$ alkyl), or halogen (e.g., —F, —Cl, —Br, or —I). The present invention particularly relates to a compound of formula (I) or a pharmaceutically acceptable salt or solvate thereof, in which any of the definitions of $R^{11}$ and $R^{12}$, including any of the preferred definitions of $R^{11}$ and $R^{12}$ described herein above, are combined with any of the definitions, including any of the preferred definitions, provided for each of the further groups and variables comprised in formula (I).

Each $R^{13}$ is independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN. Preferably, each $R^{13}$ is independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), halogen, —CF$_3$, or —CN. More preferably, each $R^{13}$ is independently selected from $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Even more preferably, each $R^{13}$ is independently selected from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Yet even more preferably, each $R^{13}$ is independently selected from $C_{1-6}$ alkyl (e.g., methyl), —OH, —O($C_{1-6}$ alkyl), or halogen (e.g., —F, —Cl, —Br, or —I). The present invention particularly relates to a compound of formula (I) or a pharmaceutically acceptable salt or solvate thereof, in which any one of the definitions of $R^{13}$, including any one of the preferred definitions of $R^{13}$ described herein above, is combined with any of the definitions, including any of the preferred definitions, provided for each of the further groups and variables comprised in formula (I).

$R^{14}$ and $R^{15}$ are each independently selected from hydrogen, $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN. Preferably, $R^{14}$ and $R^{15}$ are each independently selected from hydrogen, $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. More preferably, $R^{14}$ and $R^{15}$ are each independently selected from hydrogen, $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Even more preferably, $R^{14}$ and $R^{15}$ are each independently selected from hydrogen, $C_{1-6}$ alkyl, —OH, —O($C_{1-6}$ alkyl), or halogen (e.g., —F, —Cl, —Br, or —I). Yet even more preferably, $R^{14}$ and $R^{15}$ are each hydrogen. The present invention particularly relates to a compound of formula (I) or a pharmaceutically acceptable salt or solvate thereof, in which any one of the definitions of $R^{14}$ and $R^{15}$, including any one of the preferred definitions of $R^{14}$ and $R^{15}$ described herein above, is combined with any of the definitions, including any of the preferred definitions, provided for each of the further groups and variables comprised in formula (I).

$R^{16}$ is O, S or N(—OH). Preferably, $R^{16}$ is O. The present invention particularly relates to a compound of formula (I) or a pharmaceutically acceptable salt or solvate thereof, in which any one of the definitions of $R^{16}$, including the preferred definition of $R^{16}$ described herein above, is combined with any of the definitions, including any of the preferred definitions, provided for each of the further groups and variables comprised in formula (I).

n is 0, 1, 2 or 3. Preferably, n is 0, 1 or 2. In one embodiment, n is 0. In a further embodiment, n is 2 and it is preferred that each $R^{13}$ is independently selected from hydrogen, $C_{1-6}$ alkyl, —OH, —O($C_{1-6}$ alkyl), or halogen. The present invention particularly relates to a compound of formula (I) or a pharmaceutically acceptable salt or solvate thereof, in which any one of the definitions of n, including any one of the preferred definitions of n described herein above, is combined with any of the definitions, including any of the preferred definitions, provided for each of the further groups and variables comprised in formula (I).

Each ═══ in formula (I) is independently a single bond or a double bond, provided that at least one of the two adjacent bonds ═══ is a single bond. Accordingly, the two adjacent bonds ═══ in formula (I), i.e. the two bonds ═══ which are connected to the same carbon atom, are not both double bonds. In one embodiment, each ═══ in formula (I) is a single bond. In a further embodiment, one of the two adjacent bonds ═══ in formula (I) is a single bond and each one of the other bonds ═══ is a double bond. It is preferred that the bond between the carbon atoms carrying the substituents $R^{14}$ and $R^{15}$, respectively, is a double bond. The present invention particularly relates to a compound of formula (I) or a pharmaceutically acceptable salt or solvate thereof, in which any one of the definitions of ═══ described herein above is combined with any of the definitions, including any of the preferred definitions, provided for each of the further groups and variables comprised in formula (I).

In view of the effect of the compounds of formula (I) on the promotion of neuronal differentiation, as also shown in Example 17, the bond ═══ between the carbon atoms carrying the substituents $R^{14}$ and $R^{15}$ is preferably a double bond. On the other hand and without being bound by theory, if the bond ═══ between the carbon atoms carrying the substituents $R^{14}$ and $R^{15}$ is a single bond, then Michael addition reactions of said bond ═══ to cysteine residues of cytosolic proteins (like, e.g., Keap1) may be prevented, which may result in a reduced proneness of the compounds of formula (I) to be bound to such cytosolic proteins and, consequently, an improved bioavailability and/or reduced adverse effects of the corresponding compounds. Without being bound by theory, the presence of a single bond between the carbon atoms carrying the substituents $R^{14}$ and $R^{15}$ may furthermore reduce cyclization reactions and may thus provide for an improved stability of the corresponding compounds of formula (I).

It is to be understood that, if n is 0, the ring to which $R^{13}$ would be attached is unsubstituted (i.e., the ring is substituted with hydrogen in place of $R^{13}$). A skilled person will furthermore understand that each $R^{13}$, if present, is attached to a carbon atom of said ring (i.e., $R^{13}$ is not attached to an oxygen atom).

In a preferred embodiment, the compound of formula (I) is a compound of the following formula (Ia)

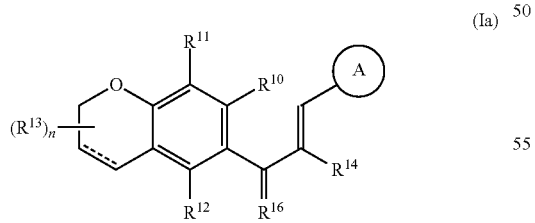

(Ia)

or a pharmaceutically acceptable salt or solvate thereof, wherein the groups and variables comprised in formula (Ia), i.e. A, $R^{10}$, $R^{11}$, $R^{12}$, $R^{13}$, $R^{14}$, $R^{16}$, n and ═══, have the meanings or preferred meanings described and defined herein above for the compound of formula (I).

Particularly preferred compounds of formula (I) are compound 1a (also referred to as "Enhancement in Neuronal Differentiation and neuroregeneration Factor 1" or "ENDF1"), compound 1b (also referred to as "ENDF3"), compound 1c (also referred to as "ENDF8"), compound 1d (also referred to as "ENDF9"), compound 1e (also referred to as "ENDF10") and compound 1f (also referred to as "ENDF11") shown below as well as pharmaceutically acceptable salts or solvates thereof:

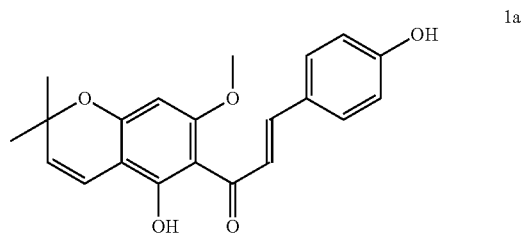

1a

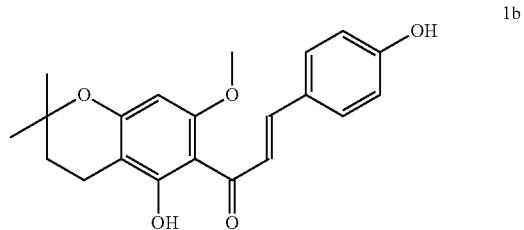

1b

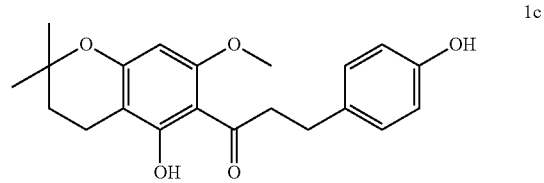

1c

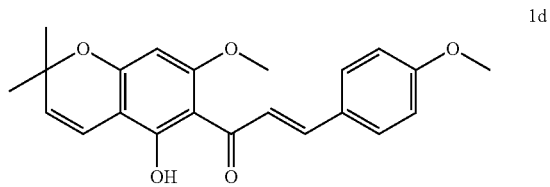

1d

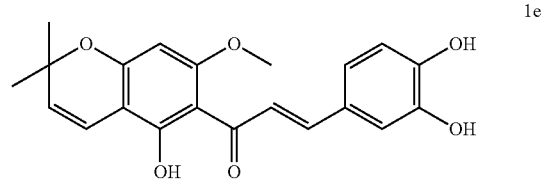

1e

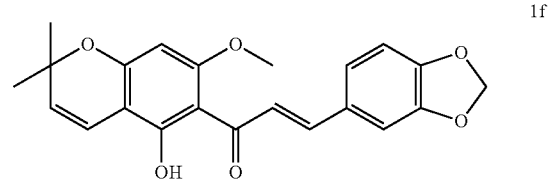

1f

Further exemplary compounds of formula (I) are the following compound 1g (also referred to as "ENDF7") as well as pharmaceutically acceptable salts or solvates thereof:

1g

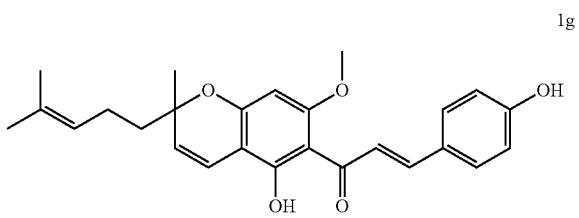 [SMILES: COc1cc2c(c(O)c1C(=O)/C=C/c1ccc(O)cc1)C=CC(C)(CCC=C(C)C)O2]

In the following, the compound of formula (II) will be described in more detail.

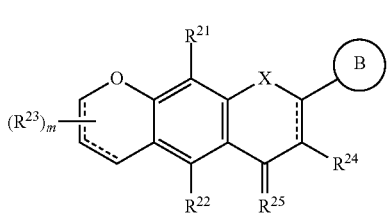

B is aryl or heteroaryl, wherein said aryl or said heteroaryl may be substituted with one or more groups (such as, e.g., one, two, three or four groups; preferably, one or two groups; more preferably, one group) independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN, preferably selected independently from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), halogen, —CF$_3$, or —CN, more preferably selected independently from $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, yet even more preferably selected independently from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, yet even more preferably selected independently from $C_{1-6}$ alkyl, —OH, —O($C_{1-6}$ alkyl), or halogen (e.g., —F, —Cl, —Br, or —I). Said aryl is preferably phenyl or naphthyl, more preferably said aryl is phenyl. Said heteroaryl is preferably 1,3-benzodioxolyl or a heteroaryl having 5 or 6 ring atoms, wherein 1, 2 or 3 of said ring atoms are heteroatoms independently selected from oxygen, sulfur or nitrogen, and the remaining ones of said ring atoms are carbon atoms. More preferably, said heteroaryl is selected from furanyl, thiophenyl (i.e., thienyl), pyrrolyl, imidazolyl, pyrazolyl, oxazolyl, isoxazolyl, furazanyl, thiazolyl, pyridinyl, pyrimidinyl, pyrazinyl, pyridazinyl, or 1,3-benzodioxolyl (e.g., 1,3-benzodioxo$_{1-5}$-yl). Even more preferably, said heteroaryl is selected from pyrrolyl, imidazolyl, pyridinyl, or pyrimidinyl. Most preferably, said heteroaryl is pyridinyl.

It is preferred that B is phenyl which may be substituted with one or more (e.g., one, two or three) groups independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN, preferably selected independently from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), halogen, —CF$_3$, or —CN, more preferably selected independently from $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, even more preferably selected independently from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, yet even more preferably selected independently from $C_{1-6}$ alkyl, —OH, —O($C_{1-6}$ alkyl), or halogen (e.g., —F, —Cl, —Br, or —I). More preferably, B is phenyl which may be substituted with one or two groups independently selected from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, preferably selected independently from $C_{1-6}$ alkyl, —OH, —O($C_{1-6}$ alkyl), or halogen. Even more preferably, B is phenyl which is unsubstituted or is substituted with one group (which is preferably in para-position) selected from $C_{1-6}$ alkyl, —OH, —O($C_{1-6}$ alkyl), or halogen. The present invention particularly relates to a compound of formula (II) or a pharmaceutically acceptable salt or solvate thereof, in which any one of the definitions of B, including any one of the preferred definitions of B described herein above, is combined with any of the definitions, including any of the preferred definitions, provided for each of the further groups and variables comprised in formula (II).

X is selected from O, S, N(H), N($C_{1-6}$ alkyl), or C(=N—OH). Preferably, X is O or S. More preferably, X is O. The present invention particularly relates to a compound of formula (II) or a pharmaceutically acceptable salt or solvate thereof, in which any one of the definitions of X, including any one of the preferred definitions of X described herein above, is combined with any of the definitions, including any of the preferred definitions, provided for each of the further groups and variables comprised in formula (II).

$R^{21}$ and $R^{22}$ are each independently selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN. Preferably, $R^{21}$ and $R^{22}$ are each independently selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), halogen, —CF$_3$, or —CN. More preferably, $R^{21}$ and $R^{22}$ are each independently selected from hydrogen, $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Even more preferably, $R^{21}$ and $R^{22}$ are each independently selected from hydrogen, $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Yet even more preferably, $R^{21}$ and $R^{22}$ are each independently selected from hydrogen, $C_{1-6}$ alkyl, —OH, —O($C_{1-6}$ alkyl), or halogen (e.g., —F, —Cl, —Br, or —I). The present invention particularly relates to a compound of formula (II) or a pharmaceutically acceptable salt or solvate thereof, in which any of the definitions of $R^{21}$ and $R^{22}$, including any of the preferred definitions of $R^{21}$ and $R^{22}$ described herein above, are combined with any of the definitions, including any of the preferred definitions, provided for each of the further groups and variables comprised in formula (II).

Each $R^{23}$ is independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN. Preferably, each $R^{23}$ is independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), halogen, —CF$_3$, or —CN. More preferably, each $R^{23}$ is independently selected from $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Even more preferably, each $R^{23}$ is independently selected from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Yet even more preferably, each $R^{23}$ is independently selected from $C_{1-6}$ alkyl (e.g., methyl), —OH, —O($C_{1-6}$ alkyl), or halogen (e.g., —F, —Cl, —Br, or —I). The present invention particularly relates to a compound of formula (II) or a pharmaceutically acceptable salt or solvate thereof, in which any one of the definitions of $R^{23}$, including any one of the preferred definitions of $R^{23}$ described herein above, is combined with any of the definitions, including any of the preferred definitions, provided for each of the further groups and variables comprised in formula (II).

$R^{24}$ is selected from hydrogen, $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN. Preferably, $R^{24}$ is selected from hydrogen, $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. More preferably, $R^{24}$ is hydrogen, $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Even more preferably, $R^{24}$ is hydrogen, $C_{1-6}$ alkyl, —OH, —O($C_{1-6}$ alkyl), or halogen (e.g., —F, —Cl, —Br, or —I). Yet even more preferably, $R^{24}$ is hydrogen. The present invention particularly relates to a compound of formula (II) or a pharmaceutically acceptable salt or solvate thereof, in which any one of the definitions of $R^{24}$, including any one of the preferred definitions of $R^{24}$ described herein above, is combined with any of the definitions, including any of the preferred definitions, provided for each of the further groups and variables comprised in formula (II).

$R^{25}$ is O, S or N(—OH). Preferably, $R^{25}$ is O. The present invention particularly relates to a compound of formula (II) or a pharmaceutically acceptable salt or solvate thereof, in which any one of the definitions of $R^{25}$, including the preferred definition of $R^{25}$ described herein above, is combined with any of the definitions, including any of the preferred definitions, provided for each of the further groups and variables comprised in formula (II).

m is 0, 1, 2 or 3. Preferably, m is 0, 1 or 2. In one embodiment, m is 0. In a further embodiment, m is 2 and it is preferred that each $R^{23}$ is independently selected from hydrogen, $C_{1-6}$ alkyl, —OH, —O($C_{1-6}$ alkyl), or halogen. The present invention particularly relates to a compound of formula (II) or a pharmaceutically acceptable salt or solvate thereof, in which any one of the definitions of m, including any one of the preferred definitions of m described herein above, is combined with any of the definitions, including any of the preferred definitions, provided for each of the further groups and variables comprised in formula (II).

Each ==== in formula (II) is independently a single bond or a double bond, provided that at least one of the two adjacent bonds ==== is a single bond. Accordingly, the two adjacent bonds ==== in formula (II), i.e. the two bonds ==== which are connected to the same carbon atom, are not both double bonds. In one embodiment, each ==== is a single bond. In a further embodiment, one of the two adjacent bonds ==== is a single bond and the other one is a double bond, while the third bond ==== (which is not adjacent to any of the other two bonds ==== ) is a double bond. The present invention particularly relates to a compound of formula (II) or a pharmaceutically acceptable salt or solvate thereof, in which any one of the definitions of ==== described herein above is combined with any of the definitions, including any of the preferred definitions, provided for each of the further groups and variables comprised in formula (II).

It is to be understood that, if m is 0, the ring to which $R^{23}$ would be attached is unsubstituted (i.e., the ring is substituted with hydrogen in place of $R^{23}$). A skilled person will furthermore understand that each $R^{23}$, if present, is attached to a carbon atom of said ring (i.e., $R^{23}$ is not attached to an oxygen atom).

In a preferred embodiment, the compound of formula (II) is a compound of the following formula (IIa)

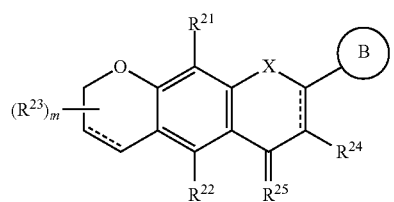

(IIa)

or a pharmaceutically acceptable salt or solvate thereof, wherein the groups and variables comprised in formula (IIa), i.e. B, $R^{21}$, $R^{22}$, $R^{23}$, $R^{24}$, $R^{25}$, m and ====, have the meanings or preferred meanings described and defined herein above for the compound of formula (II).

In a further preferred embodiment, the compound of formula (II) is a compound of the following formula (IIb)

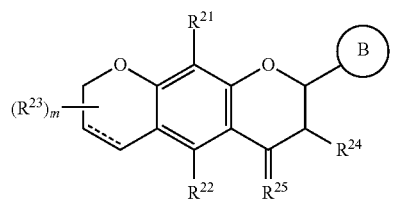

(IIb)

or a pharmaceutically acceptable salt or solvate thereof, wherein the groups and variables comprised in formula (IIb), i.e. B, $R^{21}$, $R^{22}$, $R^{23}$, $R^{24}$, $R^{25}$, m and ====, have the meanings or preferred meanings described and defined herein above for the compound of formula (II).

A particularly preferred compound of formula (II) is the compound 2a (also referred to as "ENDF5") shown below or a pharmaceutically acceptable salt or solvate thereof:

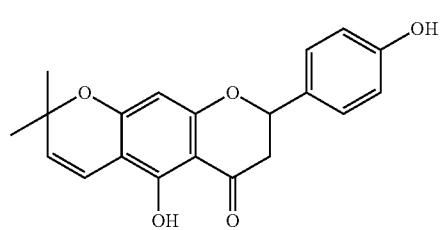

2a

The compound of formula (III) will be described in more detail in the following.

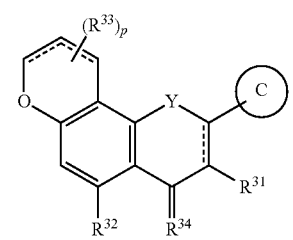

(III)

C is aryl or heteroaryl, wherein said aryl or said heteroaryl may be substituted with one or more groups (such as, e.g., one, two, three or four groups; preferably, one or two groups; more preferably, one group) independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN, preferably selected independently from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), halogen, —CF$_3$, or —CN, more preferably selected independently from $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, even more preferably selected independently from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, yet even more preferably selected independently from $C_{1-6}$ alkyl, —OH, —O($C_{1-6}$ alkyl), or halogen (e.g., —F, —Cl, —Br, or —I). Said aryl is preferably phenyl or naphthyl, more preferably said aryl is phenyl. Said heteroaryl is preferably 1,3-benzodioxolyl (e.g., 1,3-benzodiol-5-yl or 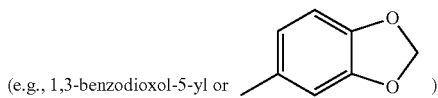 )

or a heteroaryl having 5 or 6 ring atoms, wherein 1, 2 or 3 of said ring atoms are heteroatoms independently selected from oxygen, sulfur or nitrogen, and the remaining ones of said ring atoms are carbon atoms. More preferably, said heteroaryl is selected from furanyl, thiophenyl (i.e., thienyl), pyrrolyl, imidazolyl, pyrazolyl, oxazolyl, isoxazolyl, furazanyl, thiazolyl, pyridinyl, pyrimidinyl, pyrazinyl, pyridazinyl, or 1,3-benzodioxolyl (e.g., 1,3-benzodioxol-5-yl). Even more preferably, said heteroaryl is selected from pyrrolyl, imidazolyl, pyridinyl, or pyrimidinyl. Most preferably, said heteroaryl is pyridinyl.

It is preferred that C is phenyl which may be substituted with one or more (e.g., one, two or three) groups independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN, preferably selected independently from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), halogen, —CF$_3$, or —CN, more preferably selected independently from $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, even more preferably selected independently from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, yet even more preferably selected independently from $C_{1-6}$ alkyl, —OH, —O($C_{1-6}$ alkyl), or halogen (e.g., —F, —Cl, —Br, or —I). More preferably, C is phenyl which may be substituted with one or two groups independently selected from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN, preferably selected independently from $C_{1-6}$ alkyl, —OH, —O($C_{1-6}$ alkyl), or halogen. Even more preferably, C is phenyl which is unsubstituted or is substituted with one group (which is preferably in para-position) selected from $C_{1-6}$ alkyl, —OH, —O($C_{1-6}$ alkyl), or halogen. The present invention particularly relates to a compound of formula (III) or a pharmaceutically acceptable salt or solvate thereof, in which any one of the definitions of C, including any one of the preferred definitions of C described herein above, is combined with any of the definitions, including any of the preferred definitions, provided for each of the further groups and variables comprised in formula (III).

Y is selected from O, S, N(H), N($C_{1-6}$ alkyl), or C(=N—OH). Preferably, Y is O or S. More preferably, Y is O. The present invention particularly relates to a compound of formula (III) or a pharmaceutically acceptable salt or solvate thereof, in which any one of the definitions of Y, including any one of the preferred definitions of Y described herein above, is combined with any of the definitions, including any of the preferred definitions, provided for each of the further groups and variables comprised in formula (III).

$R^{31}$ is selected from hydrogen, $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN. Preferably, $R^{31}$ is selected from hydrogen, $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. More preferably, $R^{31}$ is hydrogen, $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Even more preferably, $R^{31}$ is hydrogen, $C_{1-6}$ alkyl, —OH, —O($C_{1-6}$ alkyl), or halogen (e.g., —F, —Cl, —Br, or —I). Yet even more preferably, $R^{31}$ is hydrogen. The present invention particularly relates to a compound of formula (III) or a pharmaceutically acceptable salt or solvate thereof, in which any one of the definitions of $R^{31}$, including any one of the preferred definitions of $R^{31}$ described herein above, is combined with any of the definitions, including any of the preferred definitions, provided for each of the further groups and variables comprised in formula (III).

$R^{32}$ is selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN. Preferably, $R^{32}$ is selected from hydrogen, $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. More preferably, $R^{32}$ is selected from hydrogen, $C_{1-6}$ alkyl, —OH, —O($C_{1-6}$ alkyl), —SH, —S($C_{1-6}$ alkyl), —NH$_2$, —NH($C_{1-6}$ alkyl), or —N($C_{1-6}$ alkyl)($C_{1-6}$ alkyl). Even more preferably, $R^{32}$ is —OH, —O($C_{1-6}$ alkyl), —SH, or —S($C_{1-6}$ alkyl). Yet even more preferably, $R^{32}$ is —OH or —O($C_{1-6}$ alkyl). Yet even more preferably, $R^{32}$ is —OH or —OCH$_3$. The present invention particularly relates to a compound of formula (III)

or a pharmaceutically acceptable salt or solvate thereof, in which any one of the definitions of $R^{32}$, including any one of the preferred definitions of $R^{32}$ described herein above, is combined with any of the definitions, including any of the preferred definitions, provided for each of the further groups and variables comprised in formula (III).

Each $R^{33}$ is independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN. Preferably, each $R^{33}$ is independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), halogen, —CF$_3$, or —CN. More preferably, each $R^{33}$ is independently selected from $C_{1-6}$ alkyl, $C_{2-6}$ alkenyl (e.g., 3-methyl-2-buten-1-yl), $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Even more preferably, each $R^{33}$ is independently selected from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN. Yet even more preferably, each $R^{33}$ is independently selected from $C_{1-6}$ alkyl (e.g., methyl), —OH, —O($C_{1-6}$ alkyl), or halogen (e.g., —F, —Cl, —Br, or —I). The present invention particularly relates to a compound of formula (III) or a pharmaceutically acceptable salt or solvate thereof, in which any one of the definitions of $R^{33}$, including any one of the preferred definitions of $R^{33}$ described herein above, is combined with any of the definitions, including any of the preferred definitions, provided for each of the further groups and variables comprised in formula (III).

$R^{34}$ is O, S or N(—OH). Preferably, $R^{34}$ is O. The present invention particularly relates to a compound of formula (III) or a pharmaceutically acceptable salt or solvate thereof, in which any one of the definitions of $R^{34}$, including the preferred definition of $R^{34}$ described herein above, is combined with any of the definitions, including any of the preferred definitions, provided for each of the further groups and variables comprised in formula (III).

p is 0, 1, 2 or 3. Preferably, p is 0, 1 or 2. In one embodiment, p is 0. In a further embodiment, p is 2 and it is preferred that each $R^{33}$ is independently selected from hydrogen, $C_{1-6}$ alkyl, —OH, —O($C_{1-6}$ alkyl), or halogen. The present invention particularly relates to a compound of formula (III) or a pharmaceutically acceptable salt or solvate thereof, in which any one of the definitions of p, including any one of the preferred definitions of p described herein above, is combined with any of the definitions, including any of the preferred definitions, provided for each of the further groups and variables comprised in formula (III).

Each ═══ in formula (III) is independently a single bond or a double bond, provided that at least one of the two adjacent bonds ═══ is a single bond. Accordingly, the two adjacent bonds ═══ in formula (III), i.e. the two bonds ═══ which are connected to the same carbon atom, are not both double bonds. In one embodiment, each ═══ is a single bond. In a further embodiment, one of the two adjacent bonds ═══ is a single bond and the other one is a double bond, while the third bond ═══ (which is not adjacent to any of the other two bonds ═══) is a single bond. The present invention particularly relates to a compound of formula (III) or a pharmaceutically acceptable salt or solvate thereof, in which any one of the definitions of ═══ described herein above is combined with any of the definitions, including any of the preferred definitions, provided for each of the further groups and variables comprised in formula (III).

It is to be understood that, if p is 0, the ring to which $R^{33}$ would be attached is unsubstituted (i.e., the ring is substituted with hydrogen in place of $R^{33}$). A skilled person will furthermore understand that each $R^{33}$, if present, is attached to a carbon atom of said ring (i.e., $R^{33}$ is not attached to an oxygen atom).

In a preferred embodiment, the compound of formula (III) is a compound of the following formula (IIIa)

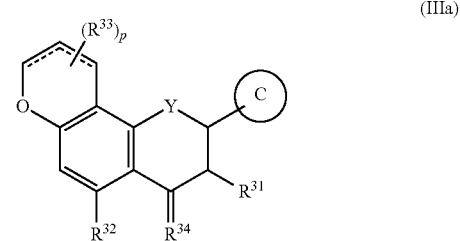

(IIIa)

or a pharmaceutically acceptable salt or solvate thereof, wherein the groups and variables comprised in formula (IIIa), i.e. C, $R^{31}$, $R^{32}$, $R^{33}$, $R^{34}$, p and ═══, have the meanings or preferred meanings described and defined herein above for the compound of formula (III).

In a further preferred embodiment, the compound of formula (III) is a compound of the following formula (IIIb)

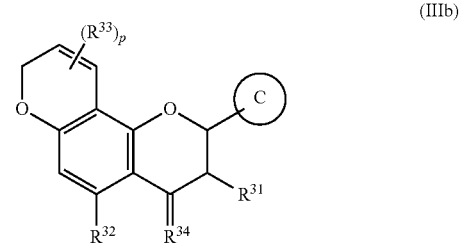

(IIIb)

or a pharmaceutically acceptable salt or solvate thereof, wherein the groups and variables comprised in formula (IIIb), i.e. C, $R^{31}$, $R^{32}$, $R^{33}$, $R^{34}$, p and ═══, have the meanings or preferred meanings described and defined herein above for the compound of formula (III).

Particularly preferred compounds of formula (III) are compound 3a (also referred to as "ENDF2") and compound 3b (also referred to as "ENDF6") shown below as well as pharmaceutically acceptable salts or solvates thereof:

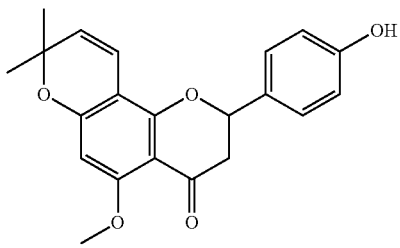

3a

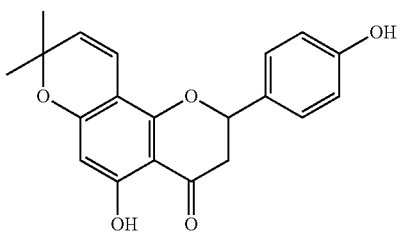

3b

In accordance with the present invention, the compounds of formula (I) or (II) are more preferred than the compounds of formula (III), while the compounds of formula (I) are even more preferred than the compounds of formula (II).

For a person skilled in the field of synthetic chemistry, various ways for the preparation of the compounds of the present invention, including the compounds of formula (I), (II) or (III), will be readily apparent. For example, the compounds of the invention can be prepared in accordance with or in analogy to the procedures described in the examples section, e.g., by cyclizing an appropriately substituted chalcone derivative (e.g., a prenylated chalcone such as xanthohumol).

As used herein, the term "alkyl" refers to a monovalent saturated aliphatic (i.e. non-aromatic) acyclic hydrocarbon group (i.e., a group consisting of carbon atoms and hydrogen atoms), which may be linear or branched and does not comprise any carbon-to-carbon double bond or any carbon-to-carbon triple bond. The term "$C_{1-6}$ alkyl" denotes an alkyl group having 1 to 6 carbon atoms (e.g., methyl, ethyl, propyl, butyl or pentyl). Preferred exemplary alkyl groups are methyl, ethyl, propyl, butyl, or pentyl; and particularly preferred exemplary alkyl groups are methyl, ethyl, propyl, or butyl. Accordingly, it is preferred that any alkyl groups (including $C_{1-6}$ alkyl groups) in the compounds of the invention, including particularly the compounds of formula (I), (II) or (III), have 1 to 5 carbon atoms, more preferably 1 to 4 carbon atoms.

As used herein, the term "alkylene" refers to a divalent saturated aliphatic acyclic hydrocarbon group which may be linear or branched and does not comprise any carbon-to-carbon double bond or any carbon-to-carbon triple bond. The term "$C_{1-6}$ alkylene" denotes an alkylene group having 1 to 6 carbon atoms. Preferred exemplary alkylene groups are methylene, ethylene, propylene, butylene, or pentylene; and particularly preferred exemplary alkylene groups are methylene, ethylene, propylene, or butylene. Accordingly, it is preferred that any alkylene groups (including $C_{1-6}$ alkylene groups) in the compounds of the invention, including particularly the compounds of formula (I), (II) or (III), have 1 to 5 carbon atoms, more preferably 1 to 4 carbon atoms.

As used herein, the term "alkenyl" refers to a monovalent unsaturated aliphatic acyclic hydrocarbon group, which may be linear or branched and comprises at least one carbon-to-carbon double bond while it does not comprise any carbon-to-carbon triple bond. "Alkenyl" may, for example, refer to 3-methyl-2-buten-1-yl (i.e., prenyl). The term "$C_{2-6}$ alkenyl" denotes an alkenyl group having 2 to 6 carbon atoms. Preferred exemplary alkenyl groups are ethenyl, propenyl, butenyl, or pentenyl; and particularly preferred exemplary alkenyl groups are ethenyl, propenyl, or butenyl. It is preferred that any alkenyl groups (including $C_{2-6}$ alkenyl groups) in the compounds of the invention, including particularly the compounds of formula (I), (II) or (III), have 2 to 5 carbon atoms, more preferably 2 to 4 carbon atoms.

As used herein, the term "alkynyl" refers to a monovalent unsaturated aliphatic acyclic hydrocarbon group, which may be linear or branched and comprises at least one carbon-to-carbon triple bond and optionally one or more carbon-to-carbon double bonds. The term "$C_{2-6}$ alkynyl" denotes an alkynyl group having 2 to 6 carbon atoms. Preferred exemplary alkynyl groups are ethynyl, propynyl, butynyl, or pentynyl; and particularly preferred exemplary alkynyl groups are ethynyl, propynyl, or butynyl. It is preferred that any alkynyl groups (including $C_{2-6}$ alkynyl groups) in the compounds of the invention, including particularly the compounds of formula (I), (II) or (III), have 2 to 5 carbon atoms, more preferably 2 to 4 carbon atoms.

As used herein, the term "aryl" refers to a monovalent aromatic hydrocarbon group, including bridged ring and/or fused ring systems, containing at least one aromatic ring. "Aryl" may, for example, refer to phenyl, naphthyl or anthracenyl.

As used herein, the term "heteroaryl" refers to an aromatic ring group, which may be a monocyclic ring group or a bridged ring and/or fused ring system (e.g., a bicyclic ring system), said aromatic ring group comprising one or more (such as, e.g., one, two, or three) ring heteroatoms independently selected from O, S, or N, wherein the aromatic ring group may, e.g., have 5 to 14 (particularly 5 or 6) ring atoms. Non-limiting examples of "heteroaryl" groups include furanyl, thiophenyl (i.e., thienyl), pyrrolyl, imidazolyl, pyrazolyl, oxazolyl, isoxazolyl, furazanyl, thiazolyl, pyridinyl, pyrimidinyl, pyrazinyl, pyridazinyl, and 1,3-benzodioxolyl (e.g., 1,3-benzodioxol-5-yl or 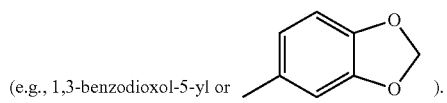 ).

As used herein, the term "halogen" refers to fluoro (—F), chloro (—Cl), bromo (—Br) or iodo (—I).

The scope of the invention embraces all pharmaceutically acceptable salt forms of the compounds of the present invention, in particular the compounds of formula (I), (II) or (III), which may be formed, e.g., by protonation of an atom carrying an electron lone pair which is susceptible to protonation, such as an amino group, with an inorganic or organic acid, or as a salt of a carboxylic acid group with a physiologically acceptable cation as they are well-known in the art. Exemplary base addition salts comprise, for example, alkali metal salts such as sodium or potassium salts; alkaline earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Moreover, the scope of the invention embraces solid forms of the compounds of the present invention, in particular the compounds of formula (I), (II) or (III), in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

Furthermore, the formulas in the present application are intended to cover all possible stereoisomers, including enantiomers and diastereomers, of the indicated compounds.

Thus, all stereoisomers of the compounds of the invention, in particular the compounds of formula (I), (II) or (III), are contemplated as part of the present invention, either in admixture or in pure or substantially pure form. The scope of the compounds according to the invention embraces all the possible stereoisomers and their mixtures. It very particularly embraces the racemic forms and the isolated optical isomers. For example, the present invention relates specifically to the (R)-enantiomer, the (S)-enantiomer and the corresponding racemic mixture of each of the compounds of formula (IIb), (IIIa) or (IIIb), including the compounds 2a, 3a and 3b, with respect to the carbon atom to which the ring group B or C is attached. The racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization.

The scope of the invention also embraces pharmaceutically acceptable prodrugs of the compounds that can be used in the present invention, in particular the compounds of formula (I), (II) or (III). Such prodrugs are derivatives which have chemically or metabolically cleavable groups and become, by solvolysis or under physiological conditions, the compounds used in the present invention which are pharmaceutically active in vivo. Prodrugs of compounds that can be used in the present invention may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound employed in the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester, N,N-diethylglycolamidoester or α-acetoxyethylester. When a compound employed in the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)-(tert-Bu), —OC(=O)—C$_{15}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$. When a compound employed in the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

The compounds described herein may be administered as compounds per se in their use as pharmacophores or pharmaceutical compositions or may be formulated as medicaments. Within the scope of the present invention are pharmaceutical compositions comprising as an active ingredient a compound of formula (I), (II) or (III) as defined herein above. The pharmaceutical compositions may optionally comprise one or more pharmaceutically acceptable excipients, such as carriers, diluents, fillers, disintegrants, lubricating agents, binders, colorants, pigments, stabilizers, preservatives, or antioxidants. The compounds of the present invention, including the compounds of formula (I), (II) or (III), may also be used in combination with another pharmaceutically active agent.

The pharmaceutical compositions can be formulated by techniques known to the person skilled in the art, such as the techniques published in Remington's Pharmaceutical Sciences, 20th Edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds according to the invention, in particular the compounds of formula (I), (II) or (III), or the above described pharmaceutical compositions comprising one ore more compounds of formula (I), (II) or (III) may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e. g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal. It is particularly envisaged that the compounds or pharmaceutical compositions of the invention are administered orally.

If said compounds or pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, a maltodextrine or any other polysaccharide, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia, and also cyclodextrines such as, e.g., α, β, or γ-cyclodextrin or their derivatives. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Accordingly, the present invention also relates to a complex, particularly a non-covalent complex, of a compound of formula (I), (II) or (III) with one or more pharmaceutically acceptable additives or excipients. Exemplary additives or excipients include, without being limited thereto, cyclodextrins (including, e.g., α, β, and γ-cyclodextrins and derivatives thereof), ethylene glycol, propylene glycol, poly(ethylene glycol) (including, e.g., poly(ethylene glycol) having a molecular weight in the range of about 200 to about 5,000 Da), tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, carboxyalkyl thioethers, hydroxypropylcellulose, hydroxypropyl methylcellulose, polyvinylpyrrolidone, vinyl acetate copolymers, vinyl pyrrolidone, sodium lauryl sulfate, dioctyl sodium sulfosuccinate, or any combination thereof. Said cyclodextrins may, for example, be selected from hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, or any combination thereof.

Alternatively, said compounds or pharmaceutical compositions can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

It is particularly preferred that the pharmaceutical compositions or compounds of the invention, including the compounds of formula (I) or (II), are to be administered by a systemic route, an oral route, or an intracerebral route (for example, but being not limited thereto, by osmotic minipumps or ports).

It is furthermore envisaged that the compounds according to the invention, including the compounds of formula (I), (II) or (III), are conjugated with an amino acid, a peptide, a diamine or a polyamine. It may thereby be possible to increase the ability of the compounds of the invention to cross the blood-brain barrier and, thus, to enhance their bioavailability (Drin G et al., AAPS PharmSci. 2002; 4(4): E26; Hervé F et al., AAPS J. 2008 September; 10(3):455-472). Conjugation can be performed by methods known in the art. For example, a compound of the invention having a carboxylic acid group may be activated (using, e.g., a carbodiimide) and reacted with an amino group of an amino acid, a peptide, a diamine or a polyamine. Exemplary amino acids which may be used for conjugation include, without being limited thereto, glycine, alanine, phenylalanine, or valine. Peptides which may be used for conjugation include, without being limited thereto, cell-penetrating peptides such as, e.g., protegrins or protegrin-derived peptides (e.g., SynB, including particularly SynB1 or SynB3), penetratin (including particularly L-penetratin or D-penetratin), transportan, trans-activating transcriptional activator from HIV-1 (Tat), model amphipathic peptide (MAP), sequence signal-based peptide (SBP), or fusion sequence-based peptide (FBP). The peptides, including the above described cell-penetrating peptides, to be used for conjugation may, e.g., have about 2 to about 50 amino acid residues, preferably about 10 to about 30 amino acid residues. Exemplary diamines include, without being limited thereto, hexamethylenediamine or putrescine. Polyamines to be used for conjugation include, for example, spermidine or spermine. Other compounds known in the art to be useful for increasing permeability through the blood-brain barrier, such as, e.g., L-carnitine, may also be used for conjugation with a compound of the invention. Accordingly, the present invention relates to a conjugate of a compound of formula (I), (II) or (III) with an amino acid, a peptide, a diamine or a polyamine for use in the treatment or prevention of a neurological disorder. The invention likewise relates to a pharmaceutical composition comprising a conjugate of a compound of the invention, particularly a compound of formula (I), (II) or (III), with an amino acid, a peptide, a diamine or a polyamine, the composition further comprising a pharmaceutically acceptable excipient, for use in the treatment or prevention of a neurological disorder.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds according to the invention, in particular the compounds of formula (I), (II) or (III), for administration to a human (of approximately 70 kg body weight) may be 0.05 to 2000 mg, preferably 0.1 mg to 1000 mg, of the active ingredient per unit dose. The unit dose may be administered, for example, 1 to 4 times per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The subject or patient, such as the subject in need of treatment or prevention, may be a eukaryote, an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e.g. gorilla, chimpanzee, orang-utan, gibbon), or a human. The meaning of the terms "eukaryote", "animal", "mammal", etc. is well known in the art and can, for example, be deduced from Wehner and Gehring (1995; Thieme Verlag). In the context of this invention, it is particularly envisaged that animals are to be treated which are economically, agronomically or scientifically important. Scientifically important organisms include, but are not limited to, mice, rats, and rabbits. Non-limiting examples of agronomically important animals are sheep, cattle and pig, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig); even more preferably, the subject/patient is a human.

The term "treatment of a disorder or disease" as used herein is well known in the art. "Treatment of a disorder or disease" implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

"Treatment of a disorder or disease" may, for example, lead to a halt in the progression of the disorder or disease (e.g., no deterioration of symptoms) or a delay in the progression of the disorder or disease (in case the halt in progression is of a transient nature only). "Treatment of a disorder or disease" may also lead to a partial response (e.g., amelioration of symptoms) or complete response (e.g., disappearance of symptoms) of the subject/patient suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above).

Treatment of a disorder or disease may, inter alia, comprise curative treatment (preferably leading to a complete response and eventually to healing of the disorder or disease) and palliative treatment (including symptomatic relief).

Also the term "prevention of a disorder or disease" as used herein is well known in the art. For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Figure 1B:
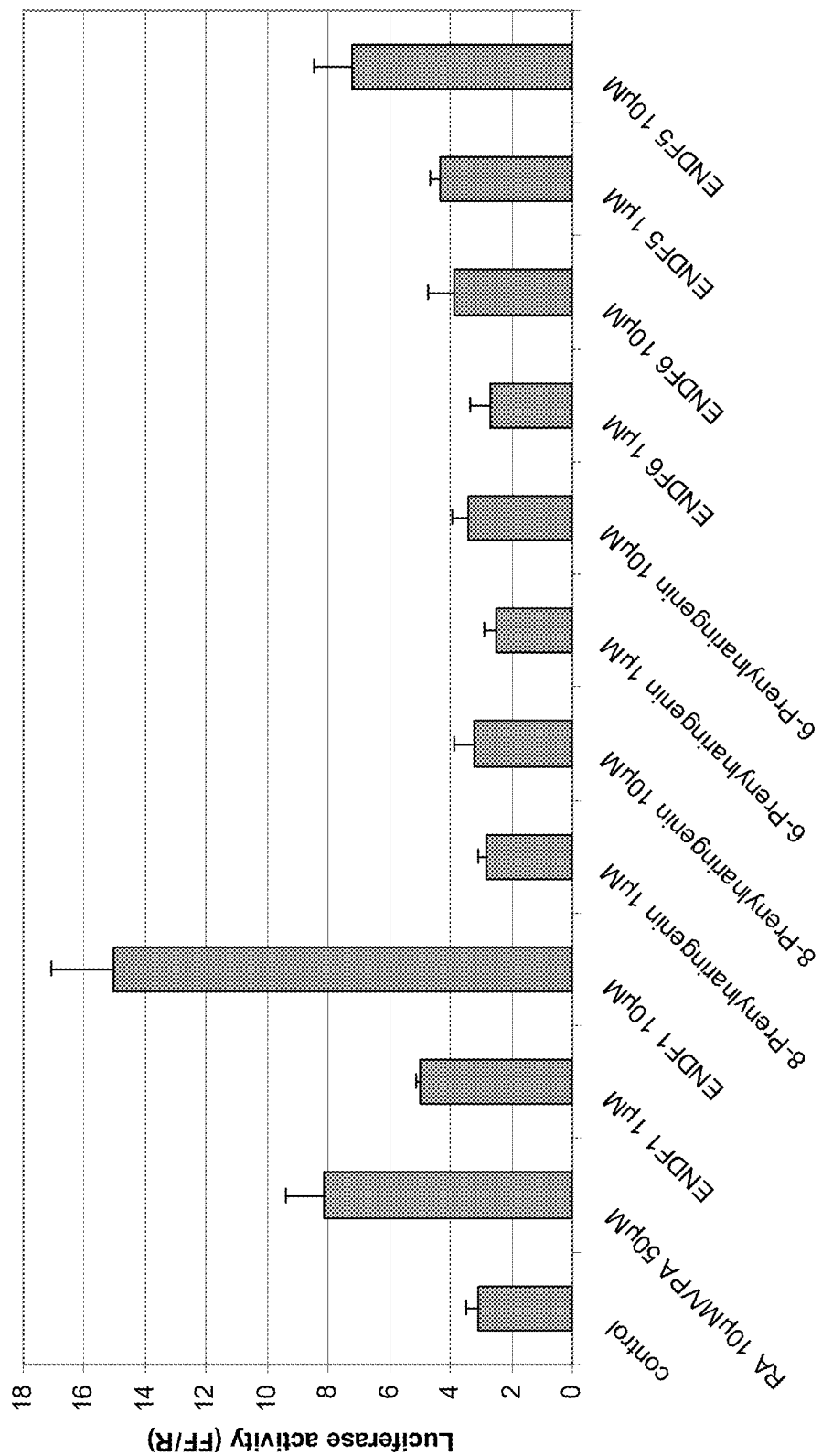
Figure 1C:
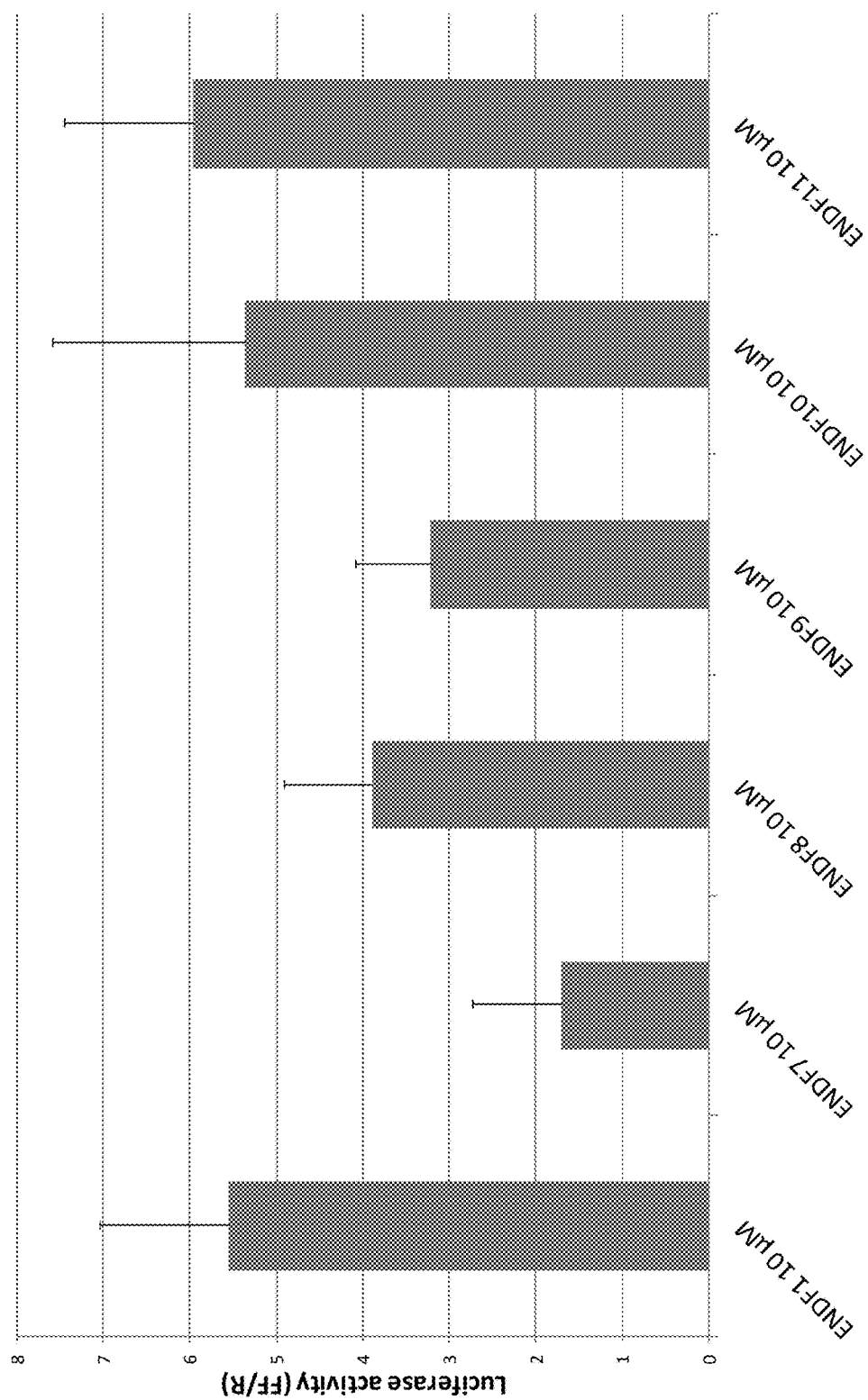
Figure 1D:
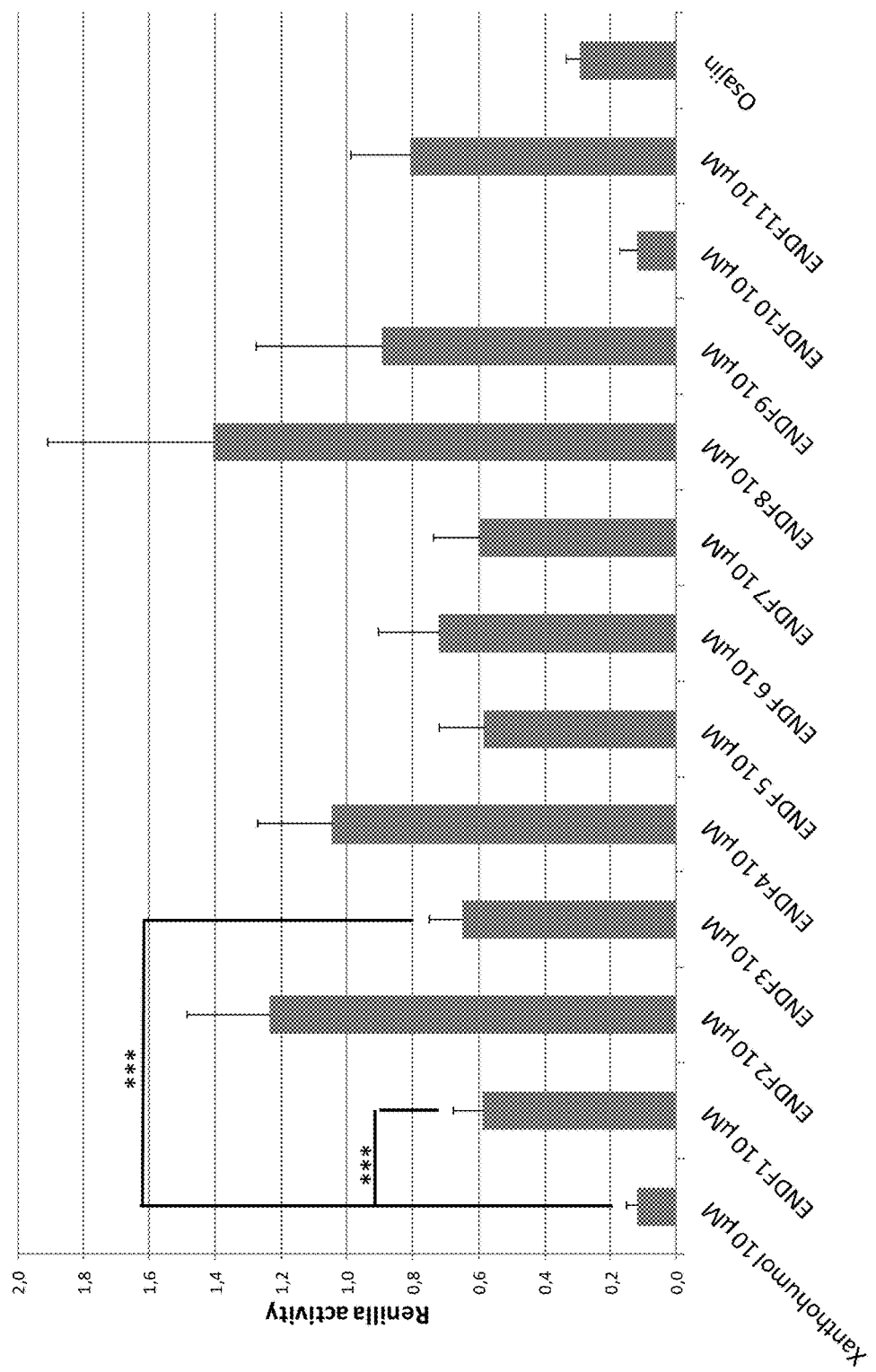

The invention is also described by the following illustrative figures. The appended figures show:

FIGS. 1A-D: The compounds 1a ("ENDF1"), 1b ("ENDF3"), 1c ("ENDF8"), 1e ("ENDF10") and 1f ("ENDF11") according to the invention significantly and strongly induce the activity of the neuronal precursor and neuronal differentiation specific DCX promoter. DCX promoter-luciferase transfected mouse embryonic day 16 forebrain (MEF) cells were stimulated for three days with the different substances, as described in Example 17. FF and R luciferase activities were measured and FF/R values were related to the value obtained by stimulation with the control medium. For normalized renilla activities, the R values of the substances tested were related to the R value obtained by stimulation with control medium. Supposing a constant number of transfected cells, the normalized renilla activities provide an approximate measure of the test substances' effect on cell survival and, thus, their relative cytotoxicity. The effects of 10 µM of, inter alia, compound 1a ("ENDF1") or compound 1b ("ENDF3") on DCX promoter induction were significantly higher than those exerted by the reference compounds xanthohumol ($p<0.001$), ENDF4 ($p<0.001$, 0.01), tocopherol ($p<0.001$, 0.01), osajin ($p<0.001$), chromanol ($p<0.001$, 0.01), and isoxanthohumol ($p<0.001$). Compound 3a ("ENDF2") also yielded good results ($p<0.01$, 0.05), as did compounds 1d ("ENDF9"), 1g ("ENDF7"), 2a ("ENDF5") and 3b ("ENDF6"). The normalized renilla activity values, as shown in FIG. 1D, point to a favorably low cytotoxicity of the compounds according to the invention as, e.g., the normalized renilla activity of compounds 1a (ENDF1) and 1b (ENDF3) was significantly higher than that exerted by the reference compounds xanthohumol and osajin. Experiments were performed in triplicates or tetraplicates and p-values of 0.05-0.001 were considered to be significant. Data are presented as mean+/−SD. Statistical analysis was performed using one-way ANOVA-Tukey post hoc.

Figure 2A:
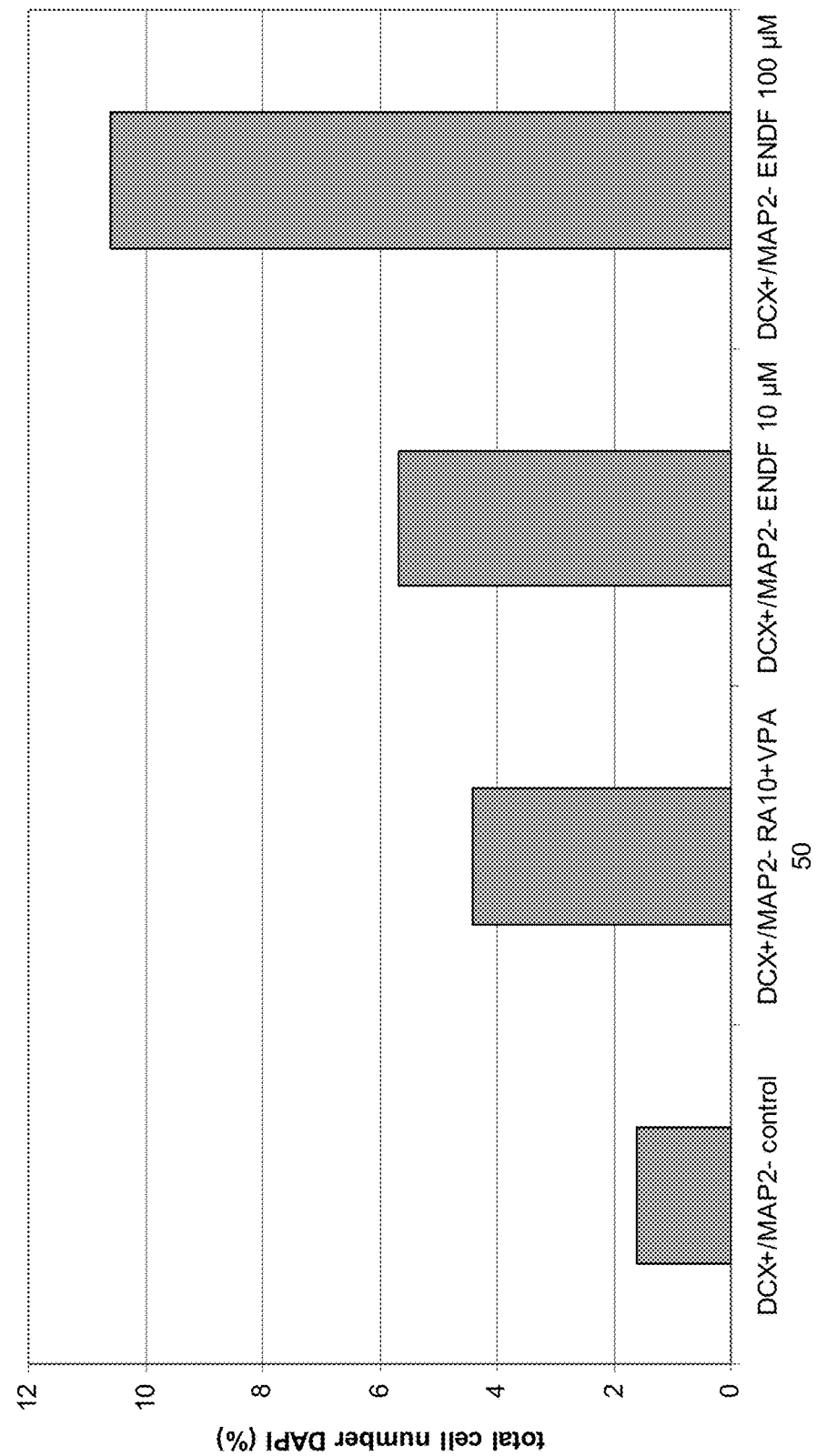
Figure 2B:
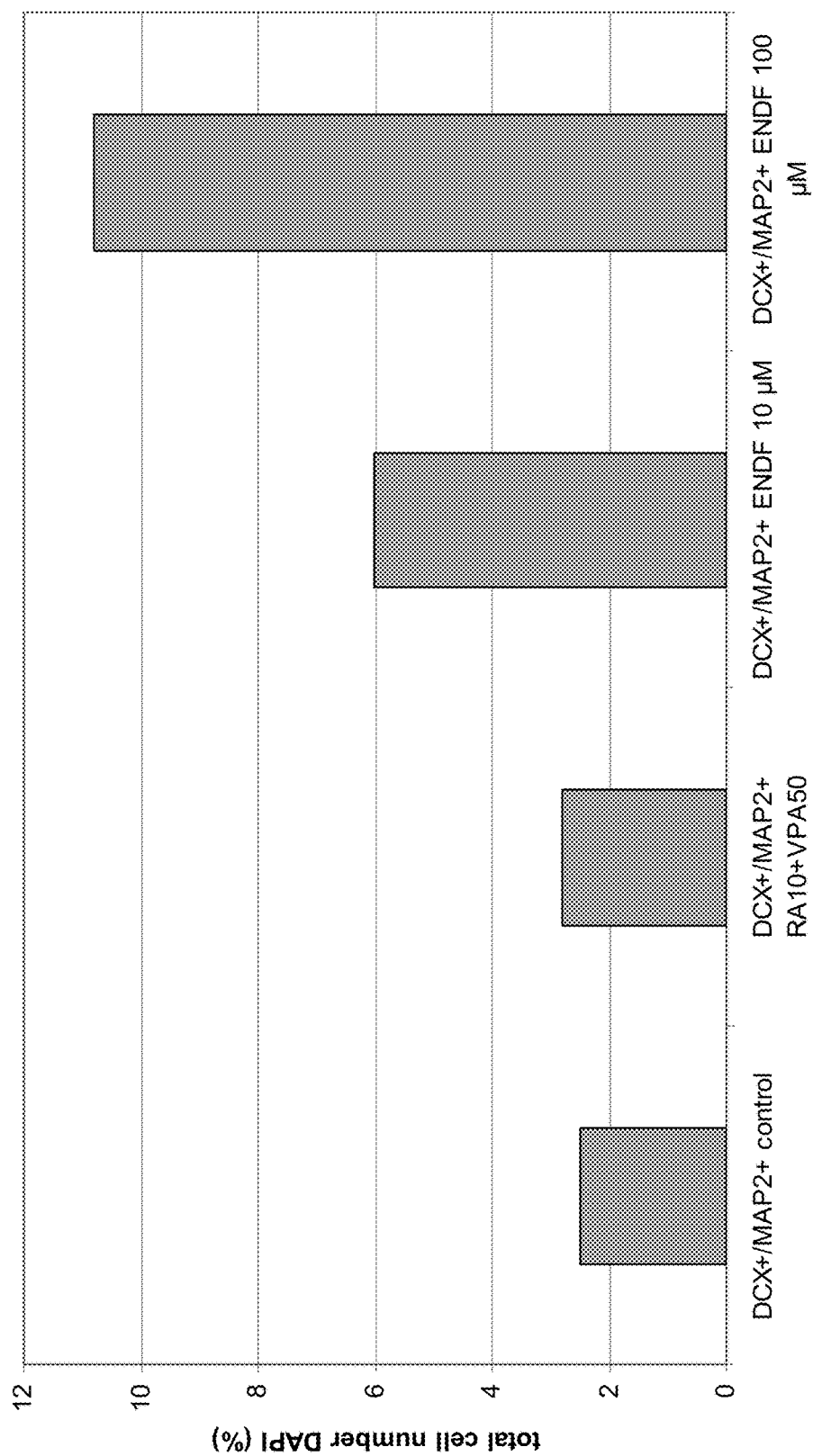
Figure 2C:
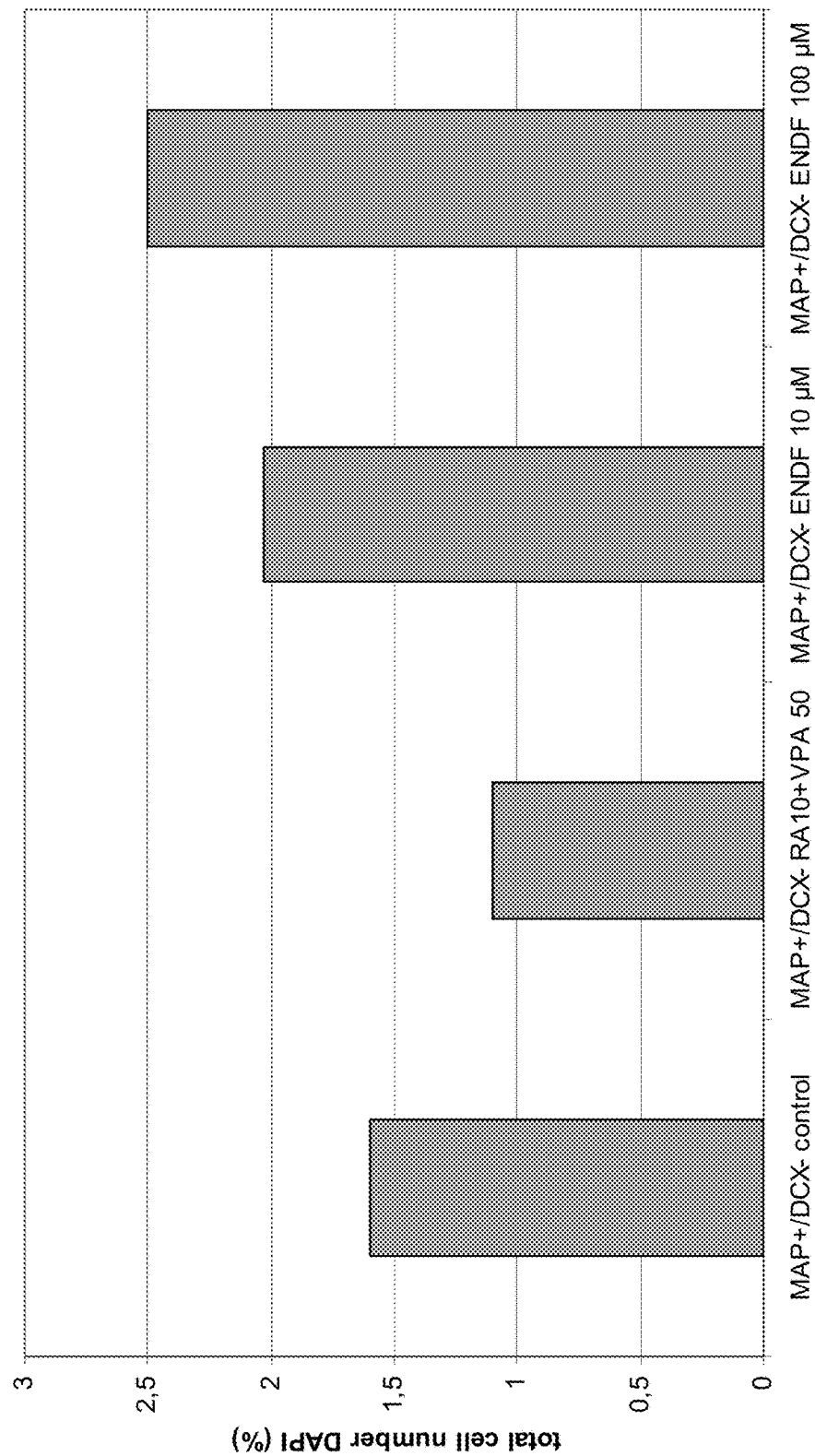

FIGS. 2A-C: Compound 1a (ENDF1; denoted as "ENDF" in the figure) at 10 and 100 µM enhances neuronal differentiation. As described in Example 18, MEF cells were incubated for 7 days in DMEM-KO medium in presence of control medium, RA and VPA, and in 10 µM or 100 µM of compound 1a. Cells were fixed and immunostained for MAP2ab, DCX and DAPI. The percentage of cells expressing MAP2ab and/or DCX was determined. FIG. 2A shows the percentage of DCX positive cells, FIG. 2B indicates the percentage of DCX/Map2ab double positive cells, and FIG. 2C shows the percentage of Map2ab positive cells. Note the elevated number of DCX positive and of MAP2ab positive cells in the cultures treated with compound 1a.

Figure 3A:
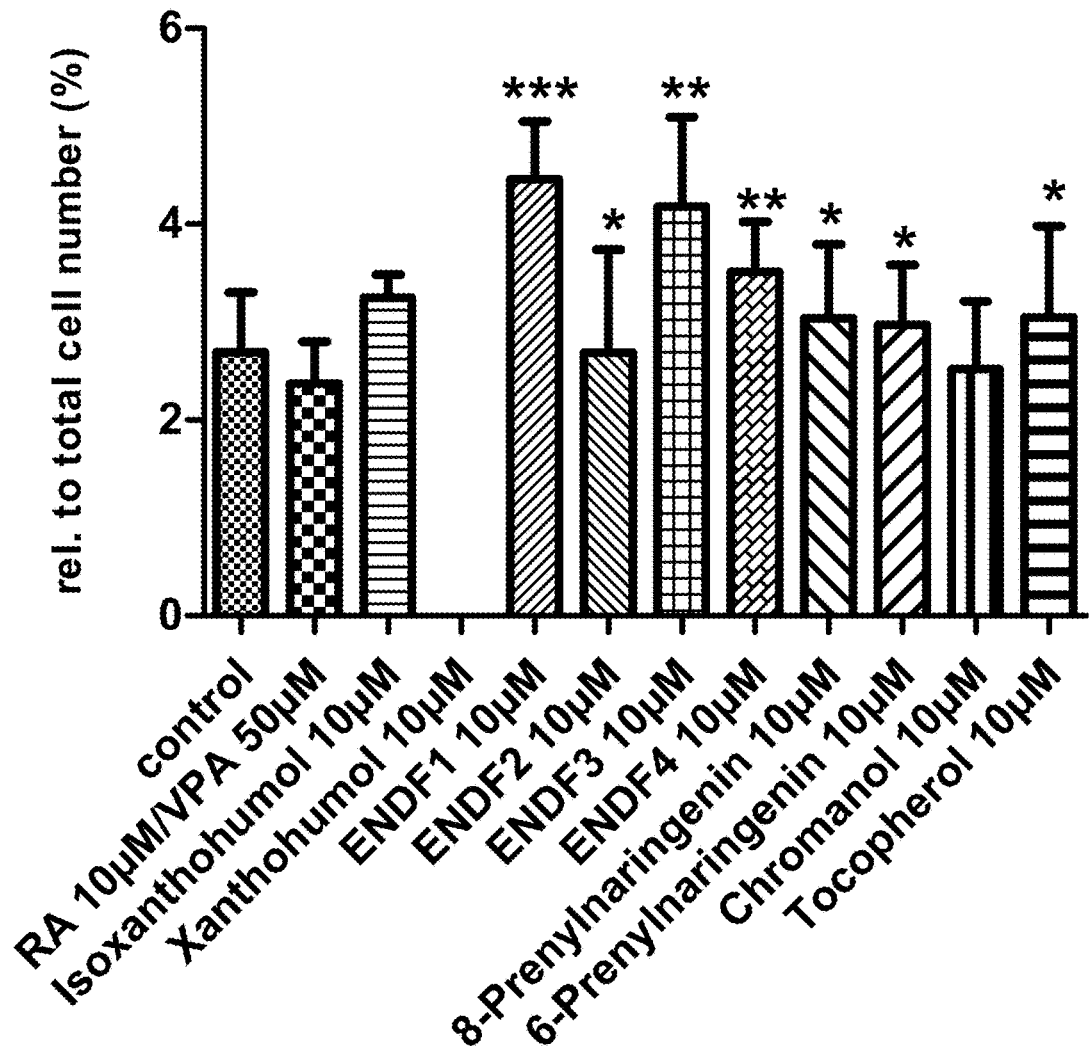
Figure 3B:
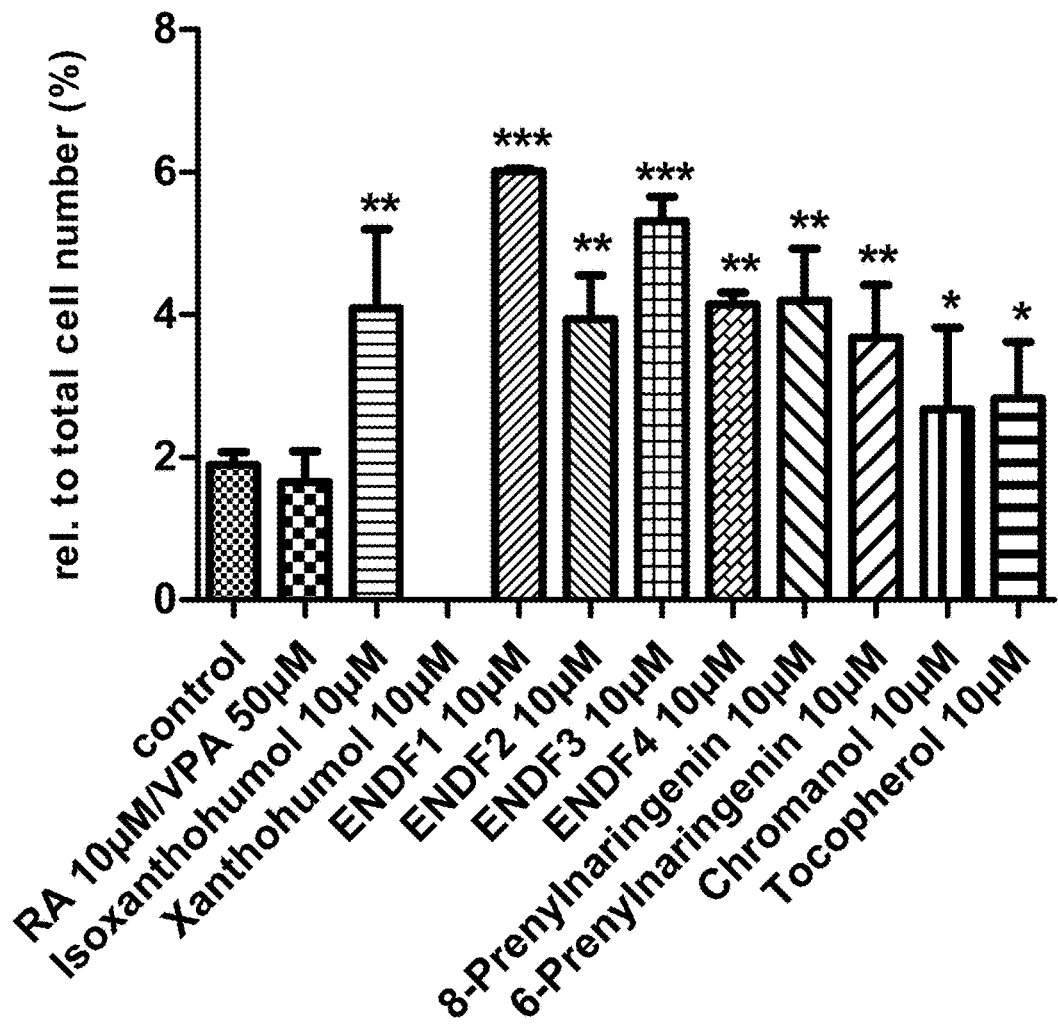

FIGS. 3A-B: Compounds of the invention enhance neuronal differentiation. As described in Example 18, MEF cells were incubated for 7 days in NB+1% FCS medium in the presence of control medium, Retinoic Acid plus Valproic Acid ("RA/VPA"), the compounds according to the invention 1a ("ENDF1"), 1b ("ENDF3") or 3a ("ENDF2"), or the reference compounds xanthohumol, isoxanthohumol, ENDF4, 6-prenylnaringenin, 8-prenylnaringenin, chromanol or tocopherol. Cells were fixed and immunostained for DCX, Map2ab and DAPI. The percentage of cells expressing DCX and Map2ab was determined. FIG. 3A shows the relative number of DCX positive cells, and FIG. 3B shows the relative number of DCX/Map2ab double positive cells. The most vigorous result shows compound 1a ($p<0.001$), while compound 1b ($p<0.01$) and ENDF4 ($p<0.01$) also strongly enhance the number of DCX positive cells (FIG. 3A). The effect of compound 3a ($p<0.05$) is similar to that of 8-prenylnaringenin ($p<0.05$), 6-prenylnaringenin ($p<0.05$) and tocopherol ($p<0.05$) whereas ENDF4 increased slightly more the number of DCX and Map2ab double positive cells (FIG. 3B). The highest number of DCX and Map2ab double positive cells show compounds 1a ($p<0.001$) and 1b ($p<0.001$). Good results demonstrate also compound 3a as well as isoxanthohumol, ENDF4, 6-prenylnaringenin and 8-prenylnaringenin with a significance of $p<0.01$. Chromanol and tocopherol marginally increase the number of double positive cells ($p<0.05$). In the figure, *refers to $p<0.001$, means $p<0.01$, and *refers to $p<0.05$.

Figure 4A:
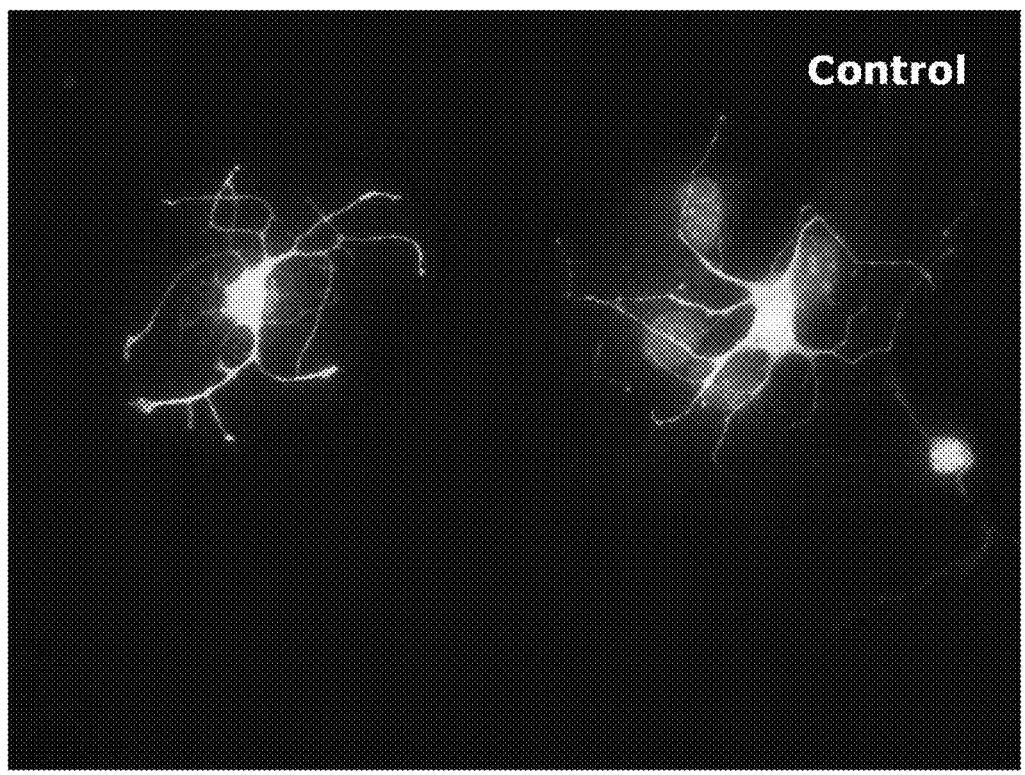
Figure 4B:
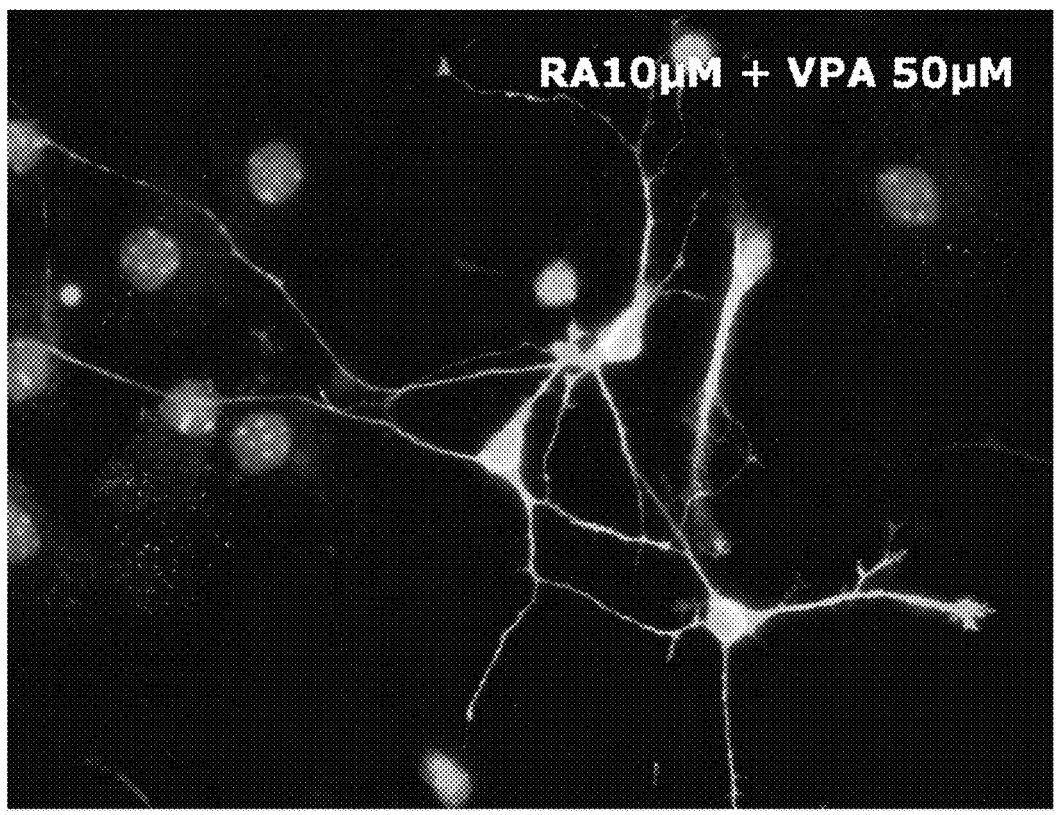
Figure 4C:
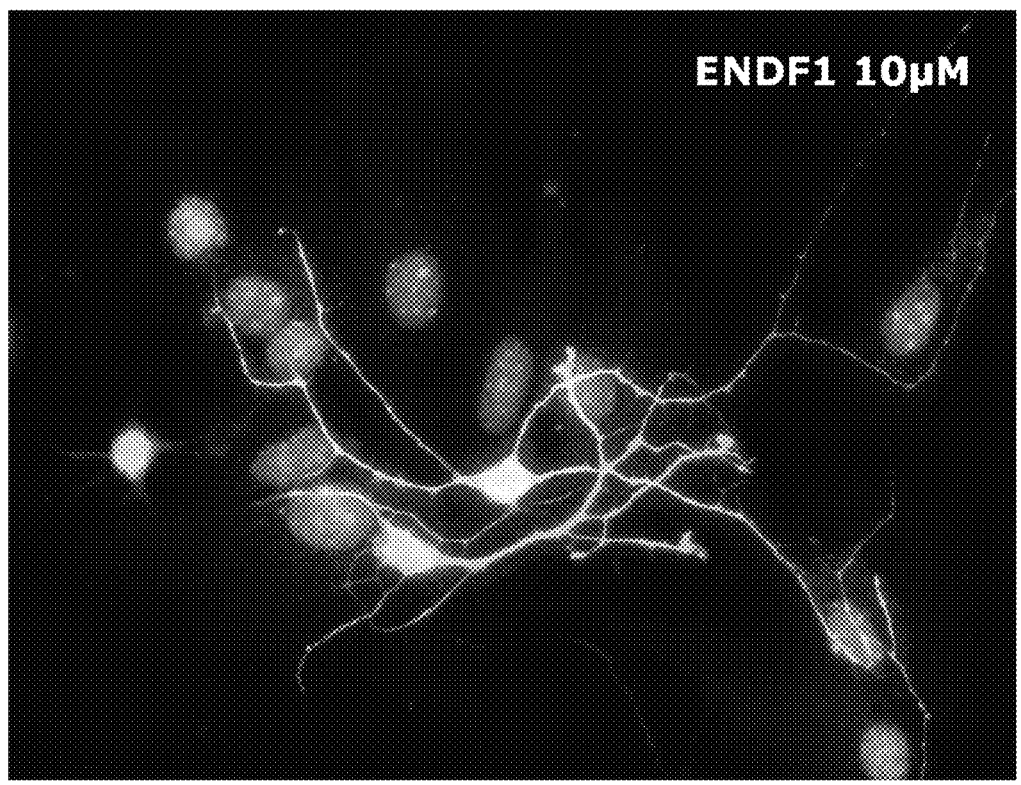
Figure 4D:
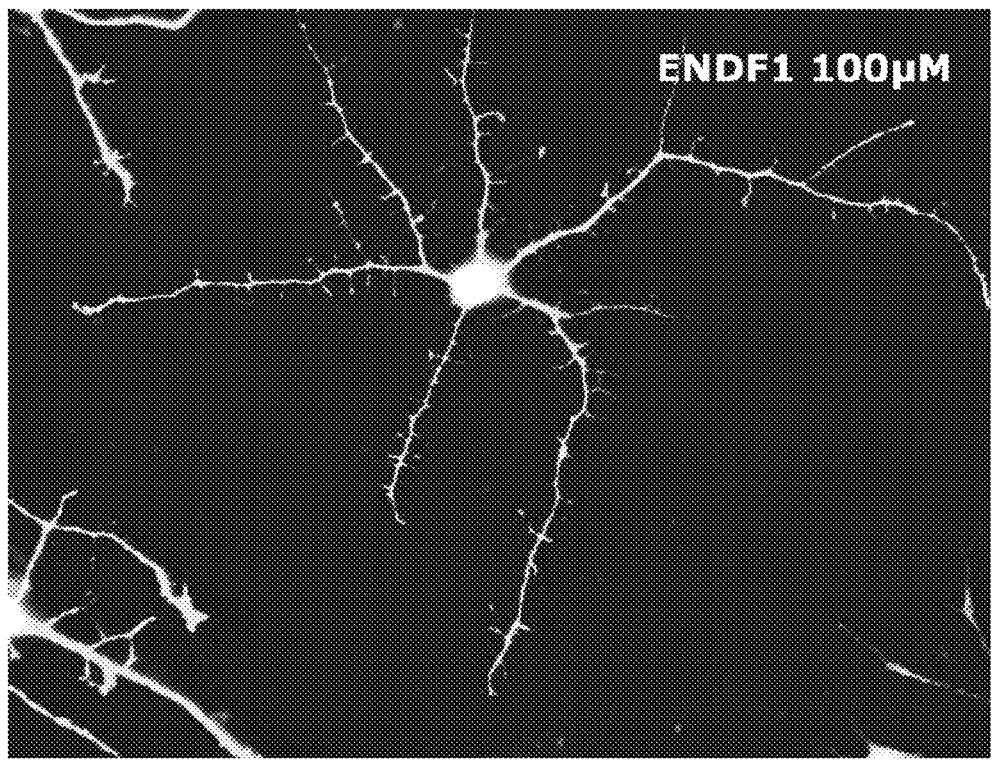
Figure 4E:
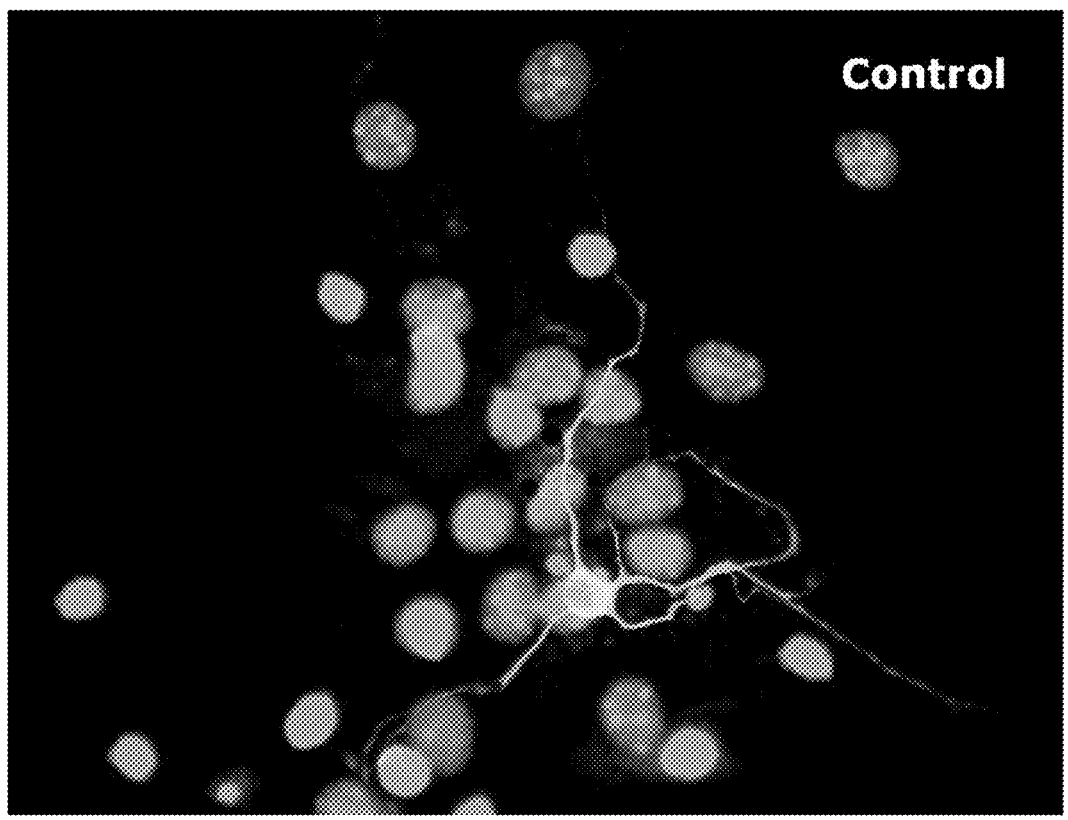
Figure 4F:
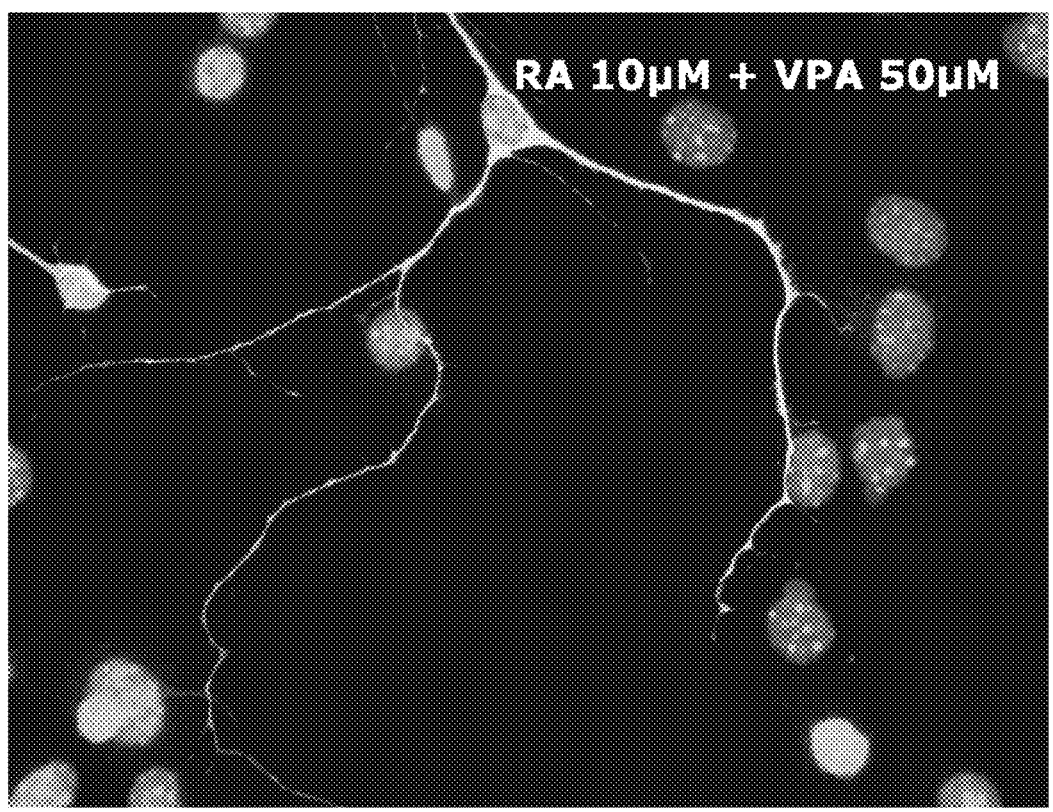
Figure 4G:
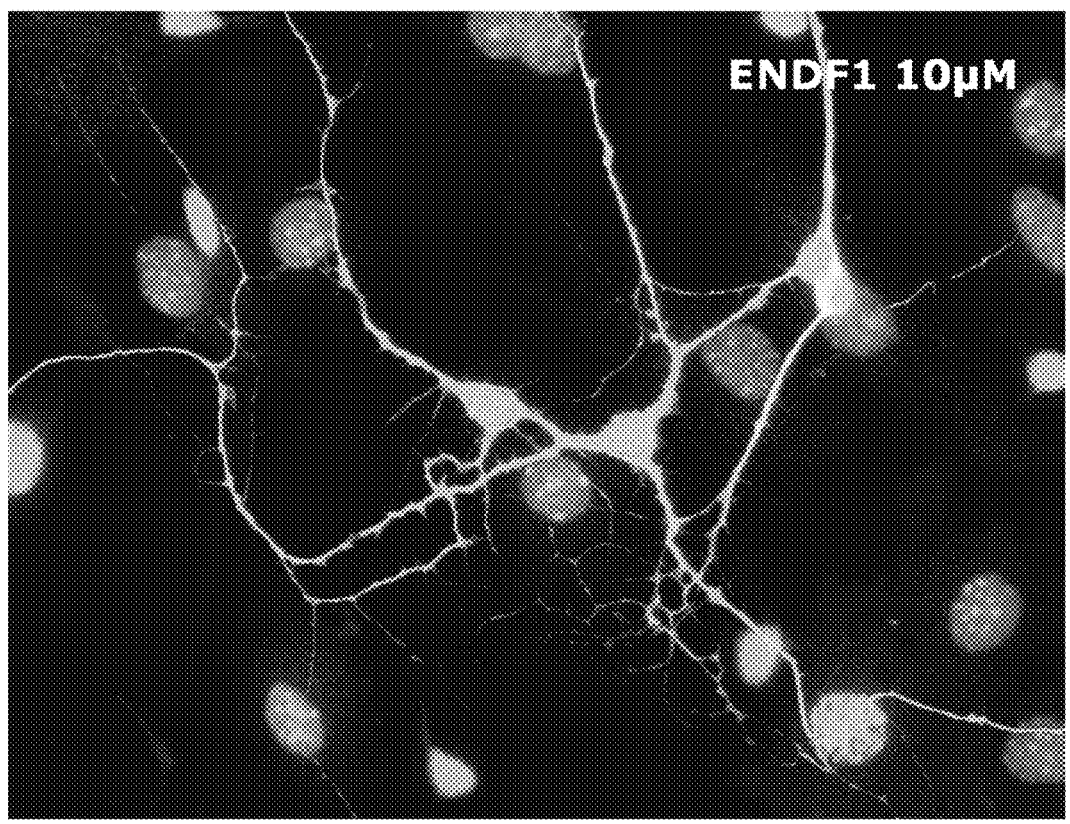
Figure 4H:
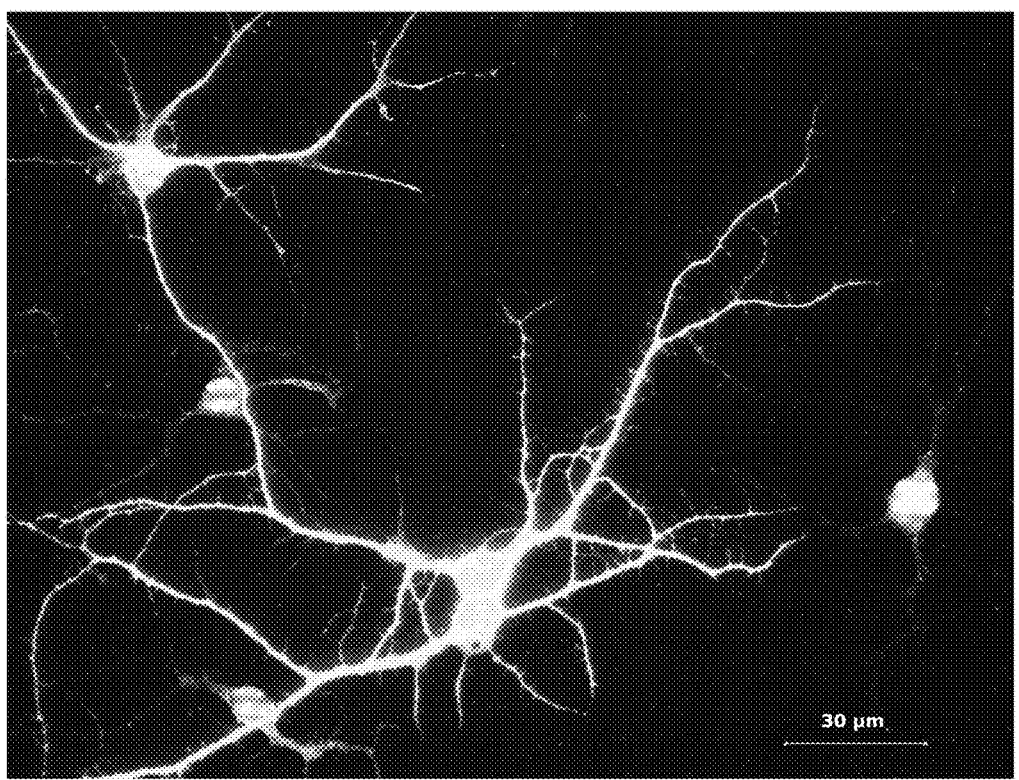
Figure 4I:
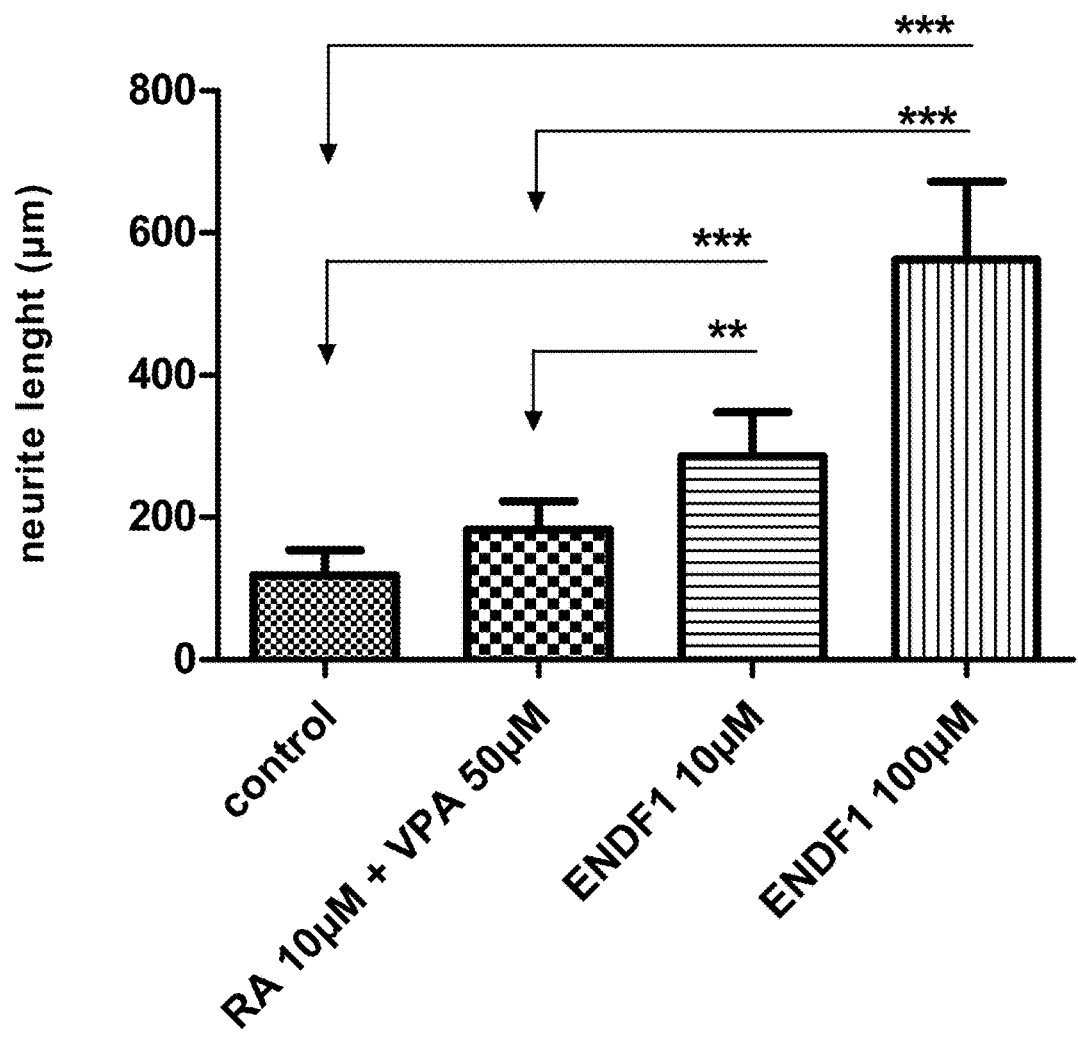
Figure 4J:
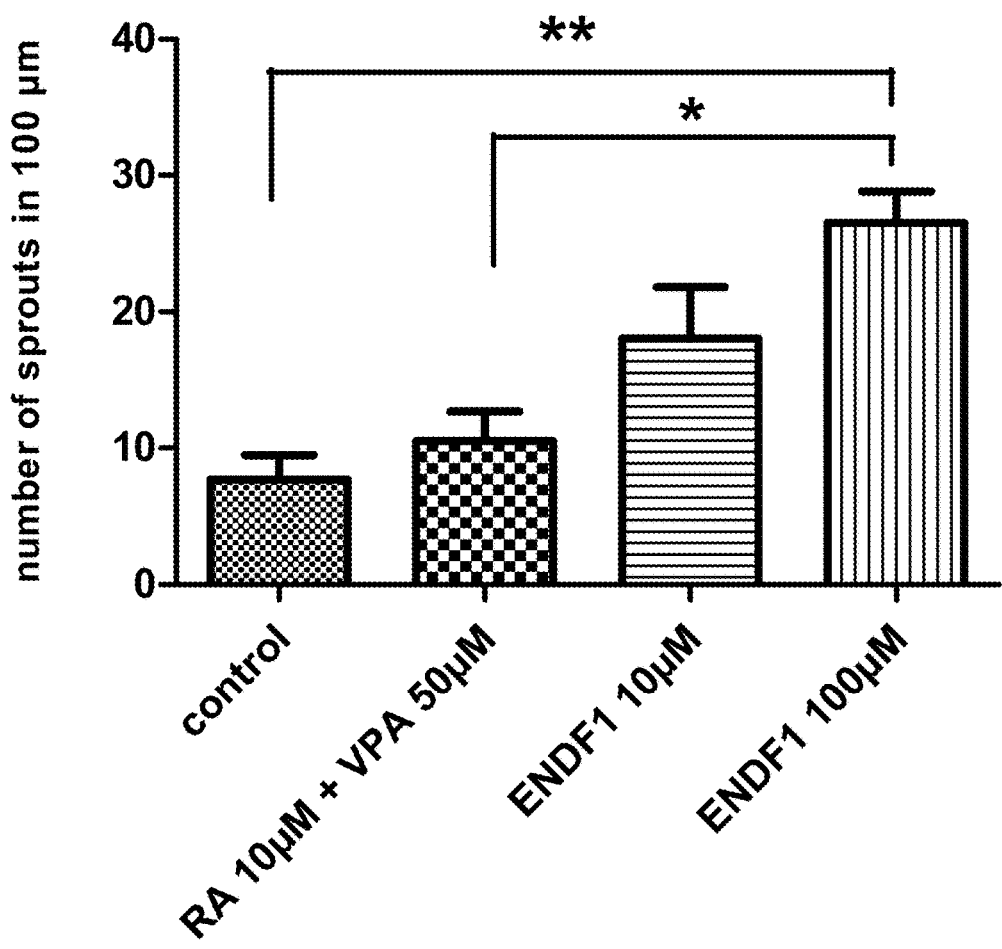

FIGS. 4A-J: Compound 1a (ENDF1) enhances neurite growth and sprouting in MEF cultures. MEF cells were treated for 3 days (FIGS. 4A to 4D) or 7 days (FIGS. 4E to 4H) with control medium DMEM-KO, RA/VPA or with compound 1a (ENDF1), fixed and stained for DCX and Map2ab. Note the extended neurite length and branching in the compound 1a stimulated culture. The scale in FIGS. 4A to 4H is 30 µm. A comparison of neurite growth (FIG. 4I) and sprouting (FIG. 4J) is furthermore shown. MEF cells were treated for 7 days with control medium, RA/VPA or with 10 µM or 100 µM of compound 1a (ENDF1), fixed and stained for DCX and Map2ab, and the length of DCX positive neurite profiles was measured using Volocity 5.4.1 measurement program. Note the significant increase in neurite length in compound 1a 10 µM ($p<0.001$) and compound 1a 100 µM ($p<0.001$) stimulated MEF cells compared to control and RA+VPA (FIG. 4I). In FIG. 4J, branches/sprouts per 100 µm are shown. Note the high density of branches/sprouts in compound 1a treated cultures and the significant difference between compound 1a 100 µM ($p<0.01$) and RA+VPA ($p<0.05$), as well as control ($p<0.01$). Experiments were performed in duplicates and p-values of 0.05-0.01 were considered to be significant. Statistical analysis was performed using one-way ANOVA-Tukey post hoc.

Figure 5A:
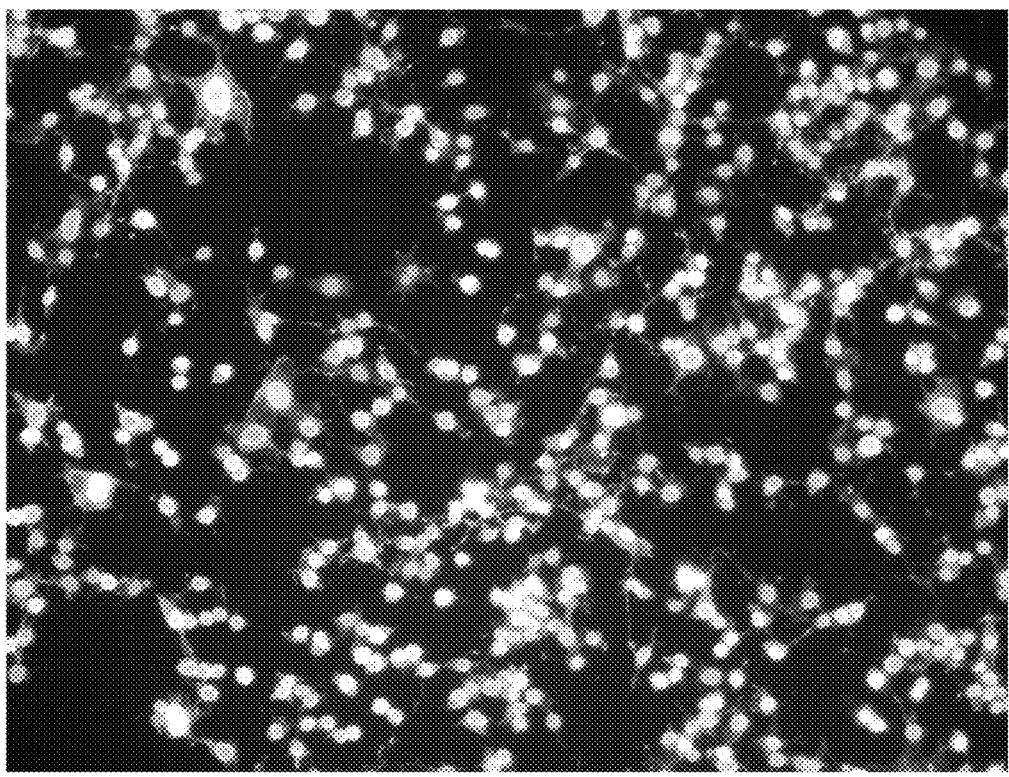
Figure 5B:
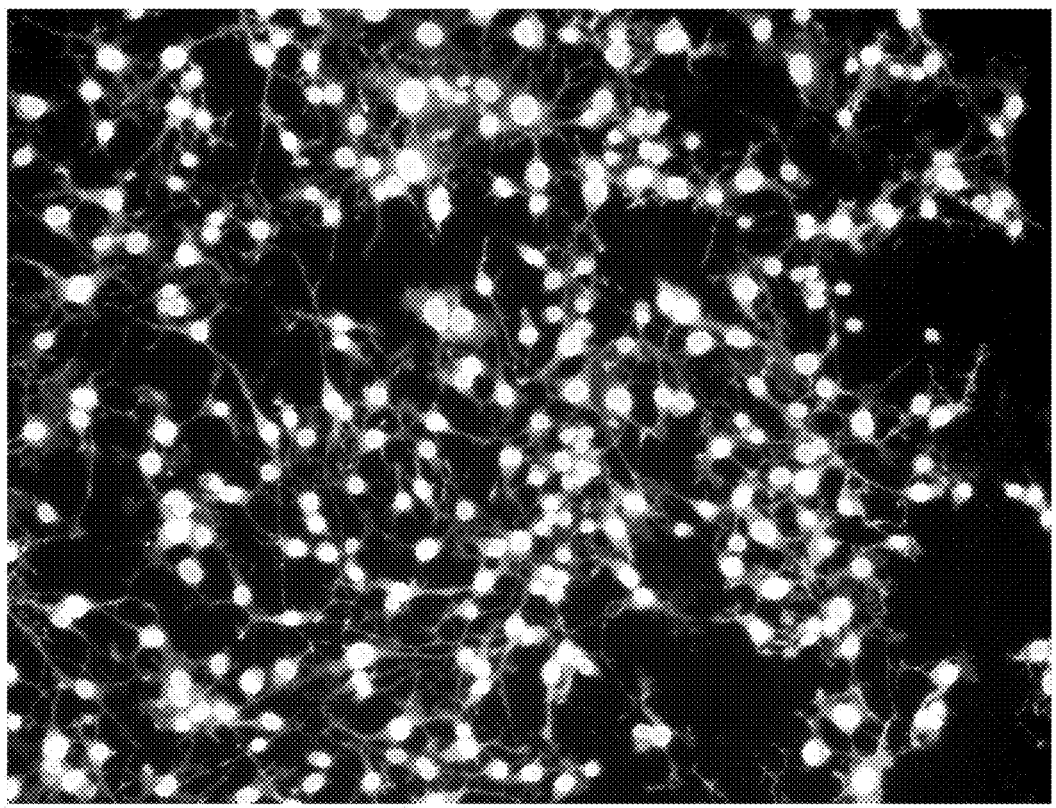
Figure 5C:
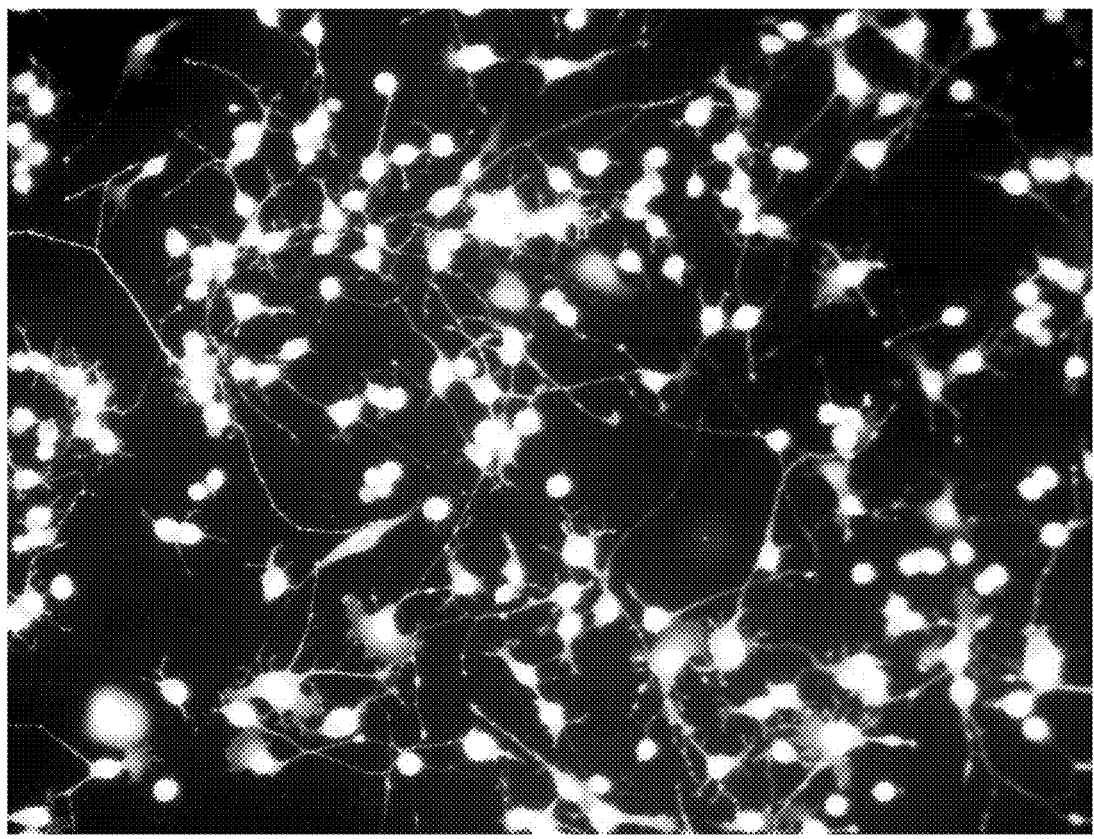
Figure 5D:
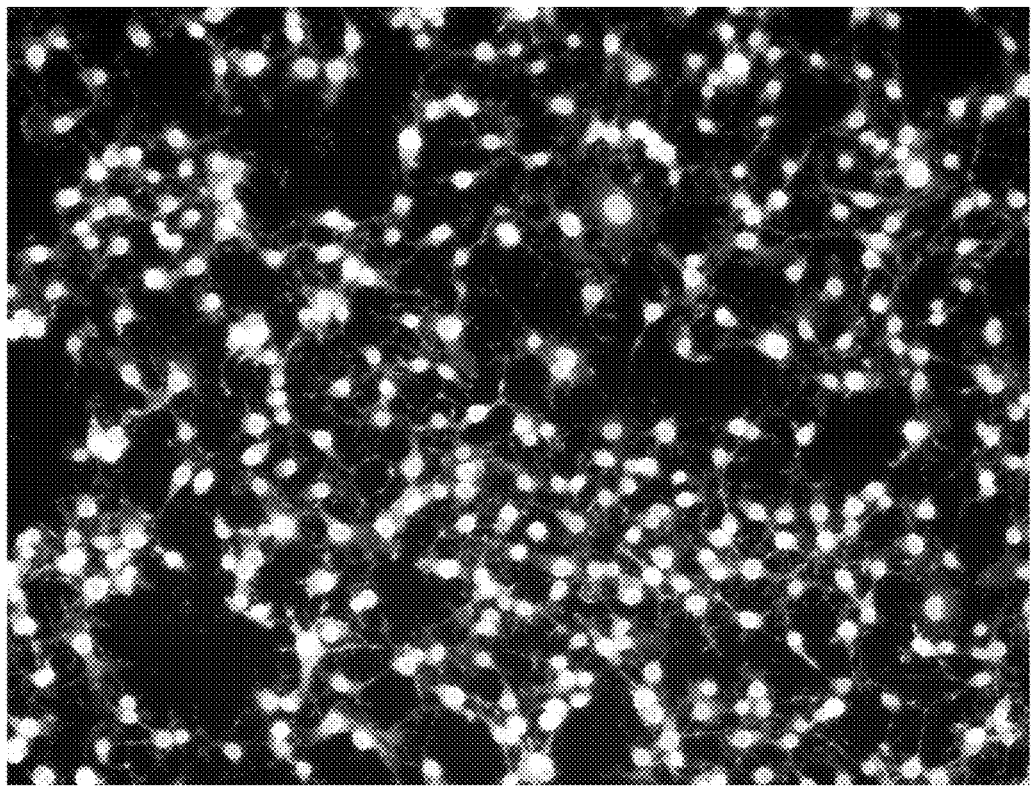
Figure 5E:
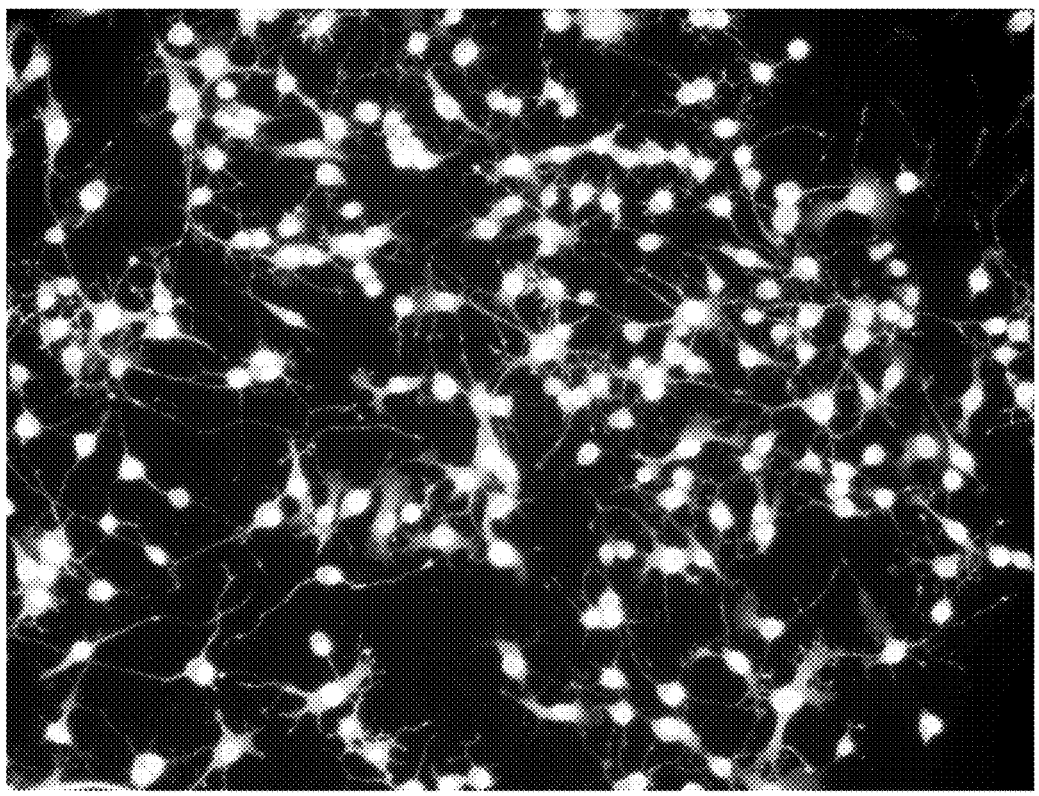
Figure 5F:
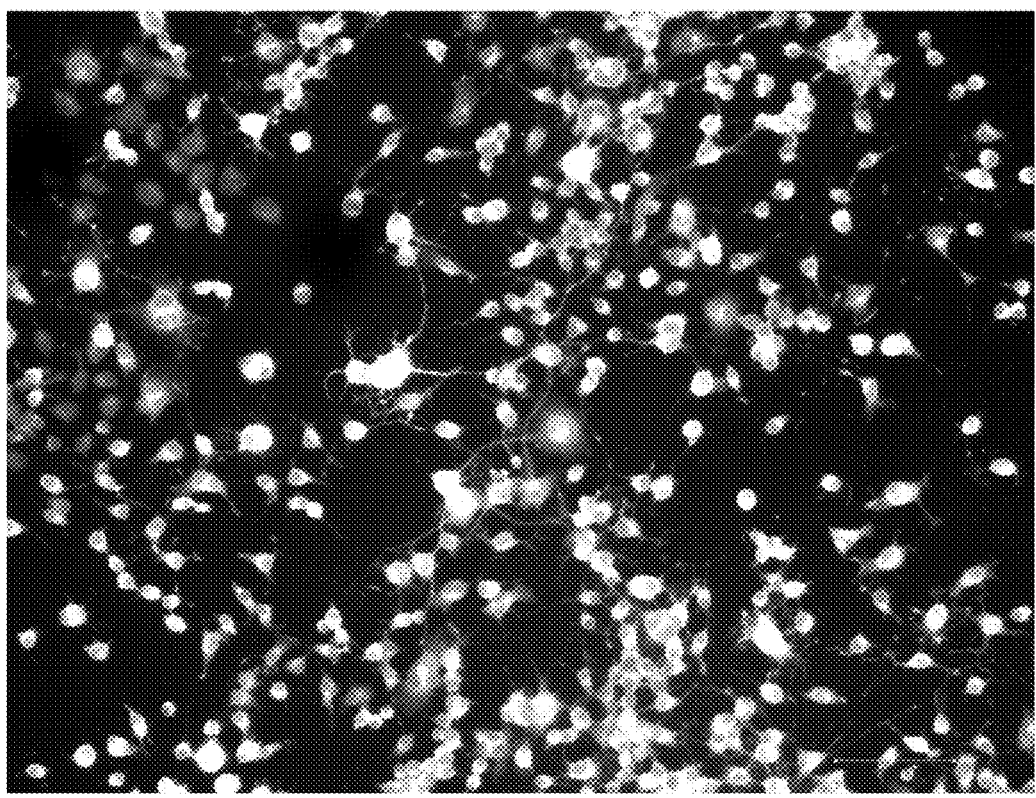
Figure 5G:
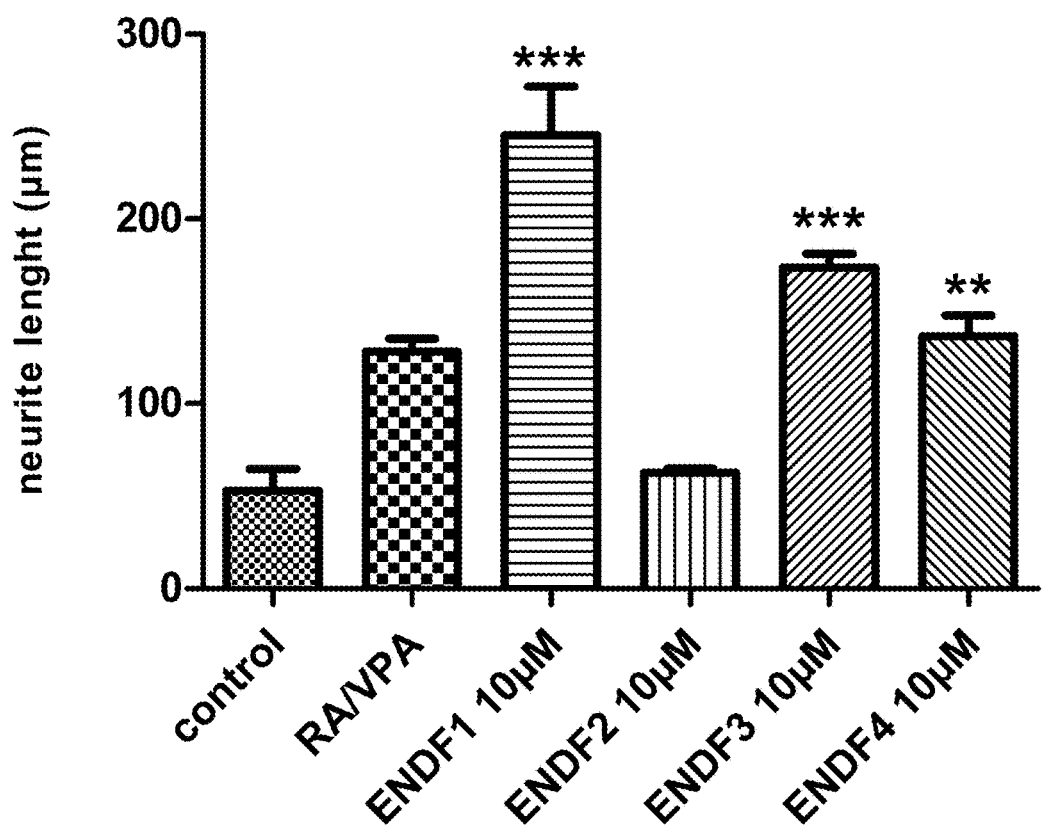

FIGS. 5A-G: The compounds of the invention enhance neurite outgrowth in Neuro-2a cells. Neuro-2a cells were treated for 2 days with control medium (FIG. 5A), RA/VPA (FIG. 5B), or with 10 µM compound 1a (ENDF1) (FIG. 5C), compound 3a (ENDF2) (FIG. 5D), compound 1b (ENDF3) (FIG. 5E) or ENDF4 (FIG. 5F), fixed and stained for GAP-43. Note that compounds 1a and 1b (ENDF1 and ENDF3) treated cultures show longer growth of neurites as well as more elaborated branches compared to control or RA/VPA treated cultures. Scale: 100 µm. Statistical analysis shows a high significance with compounds 1a and 1b ($p<0.001$) as well as ENDF4 ($p<0.01$) compared to control (FIG. 5G).

Figure 6A:
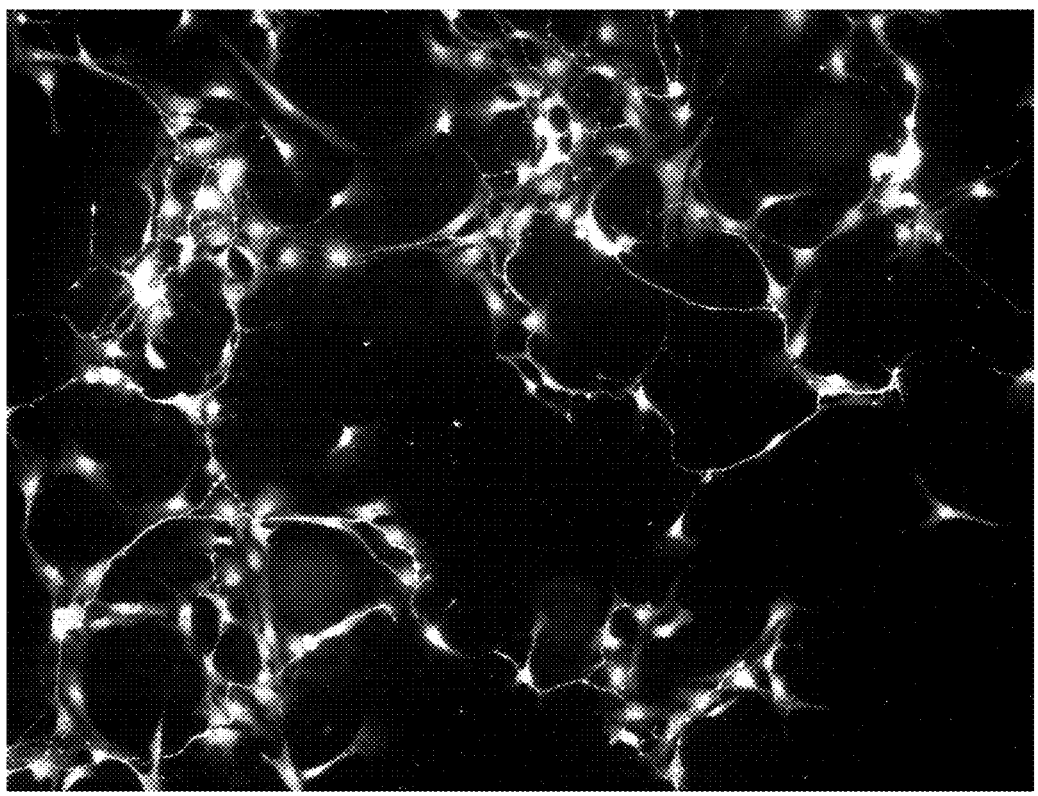
Figure 6B:
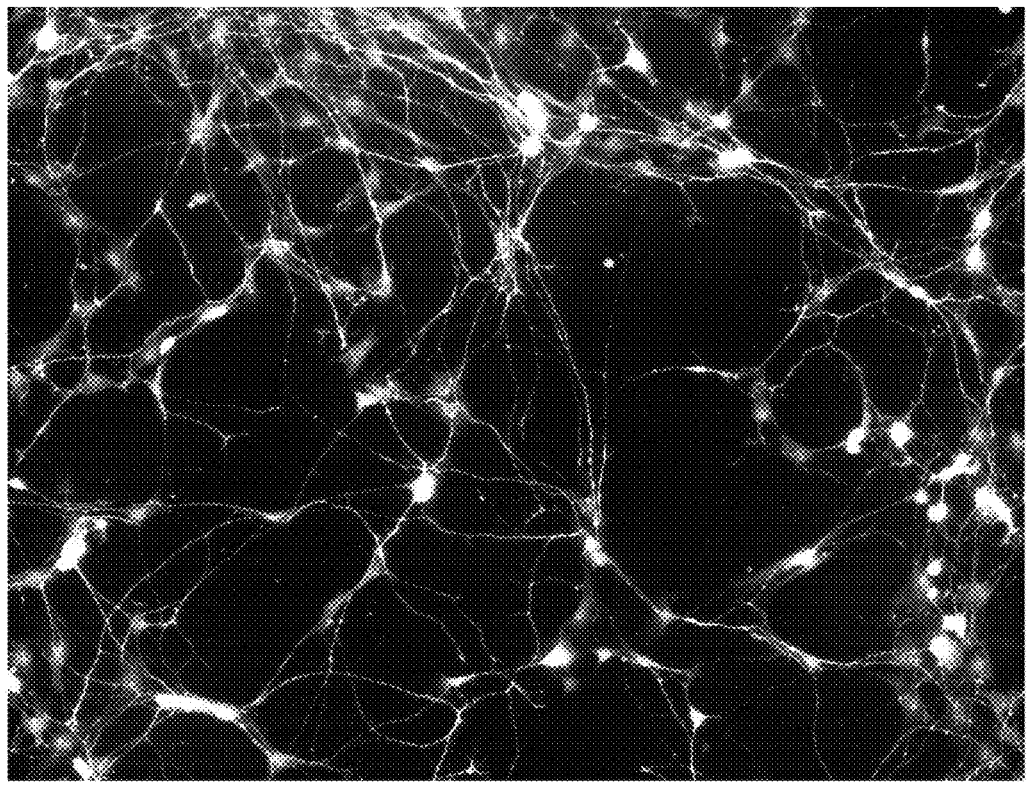
Figure 6C:
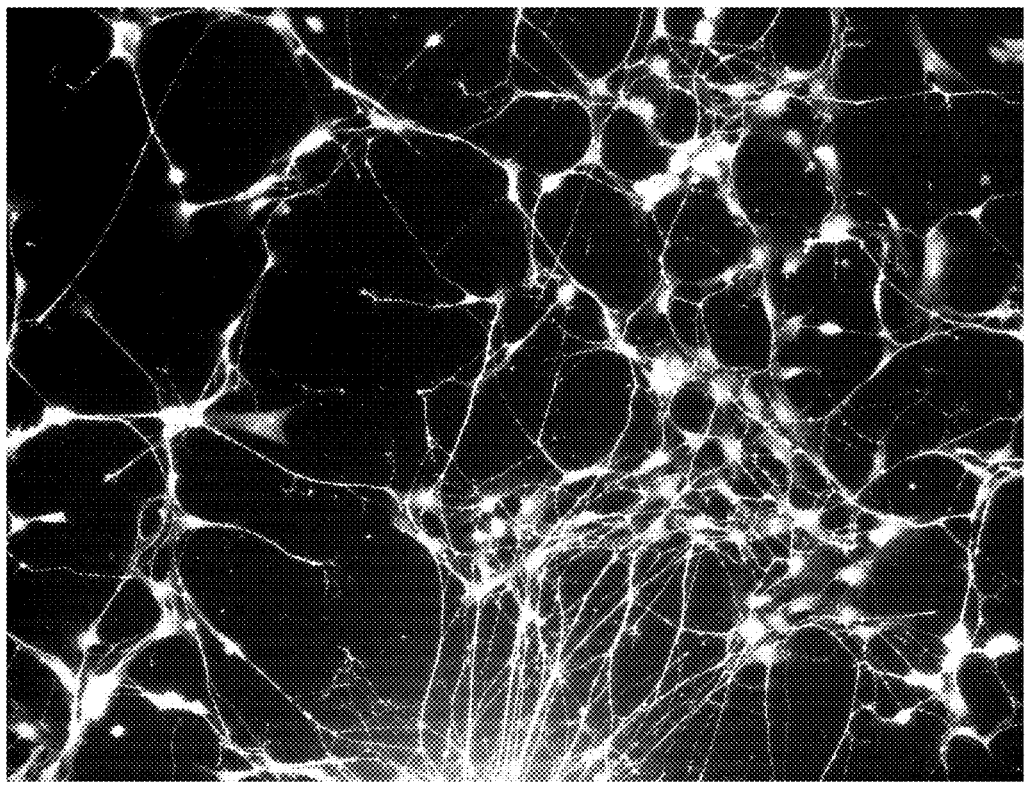
Figure 6D:
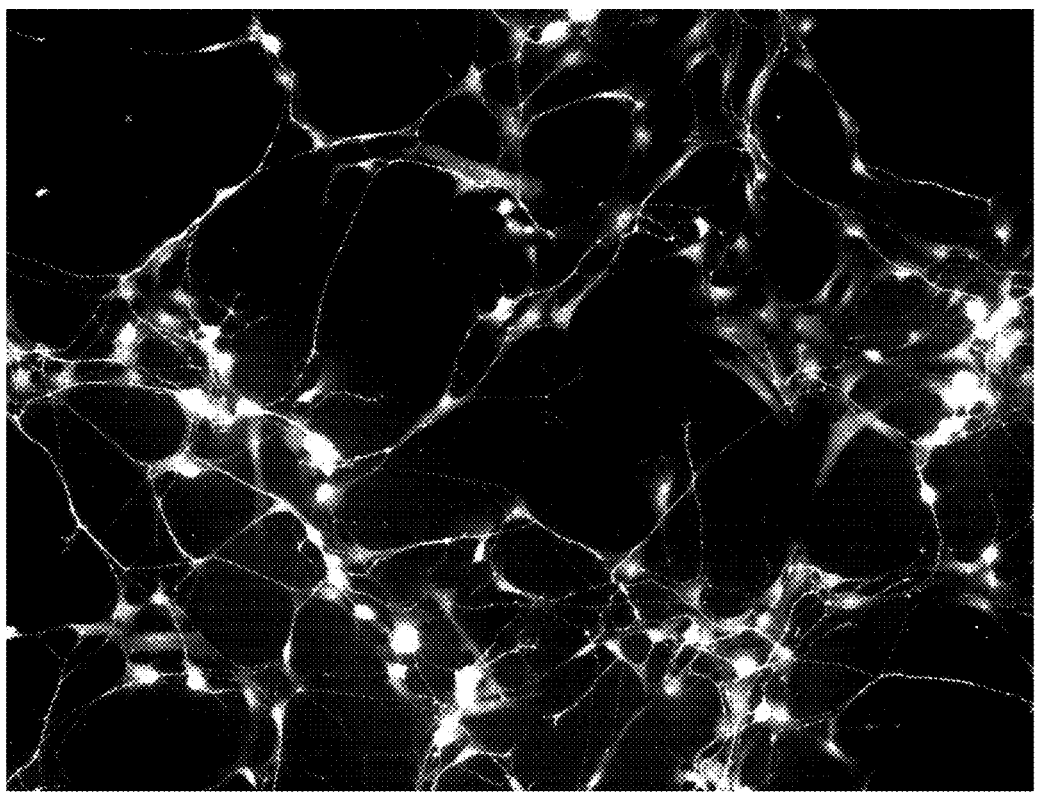
Figure 6E:
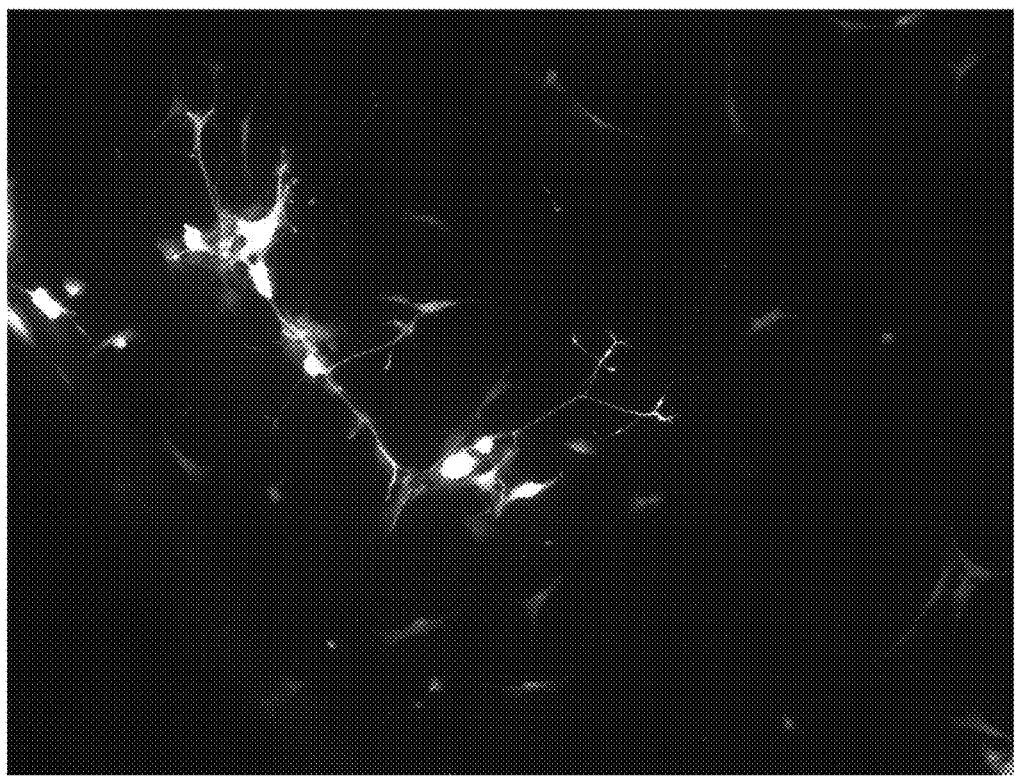
Figure 6F:
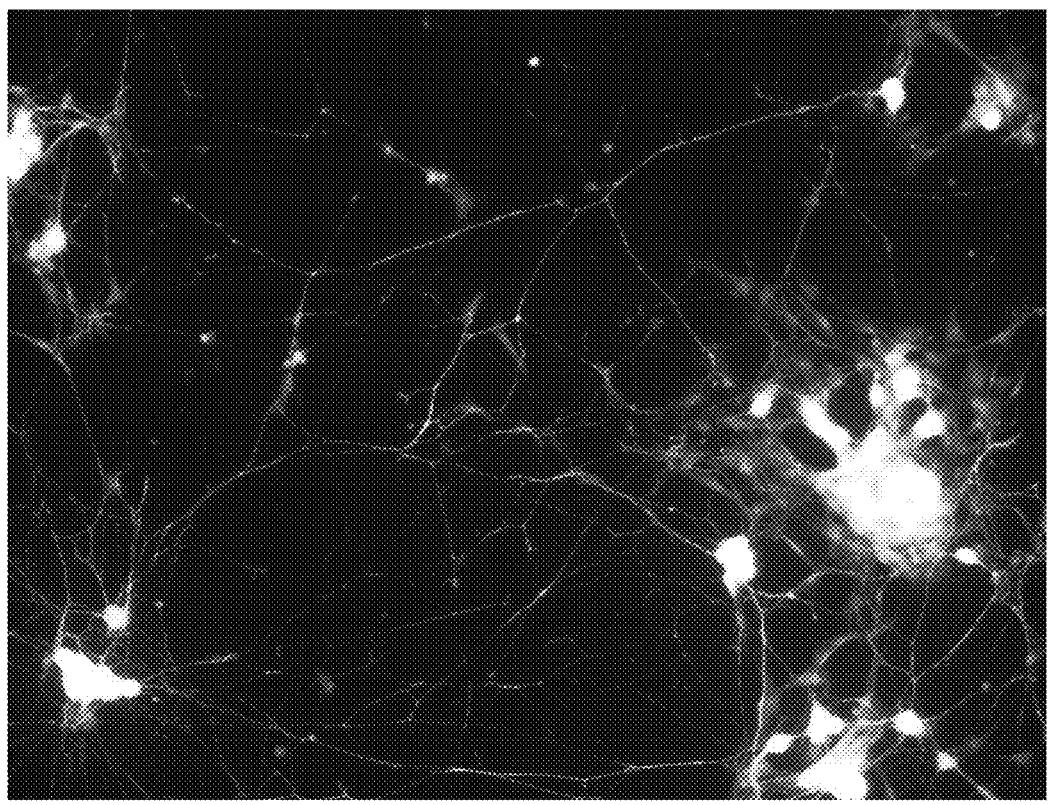
Figure 6G:
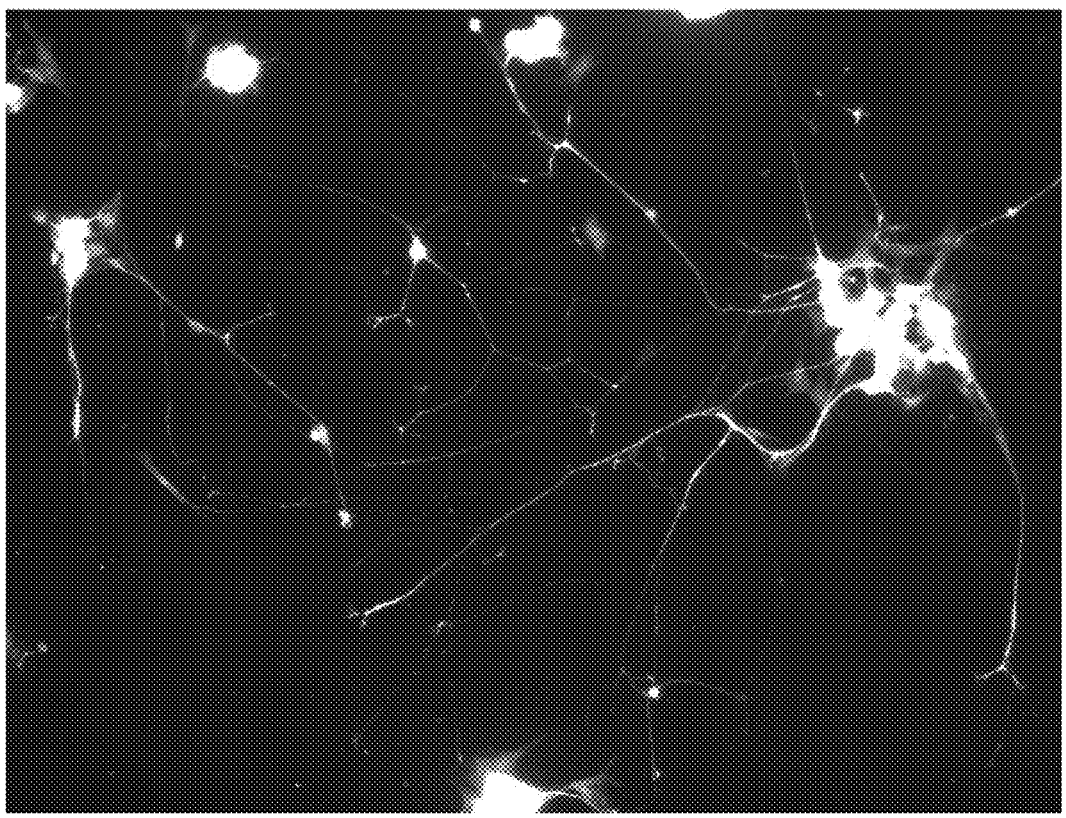
Figure 6H:
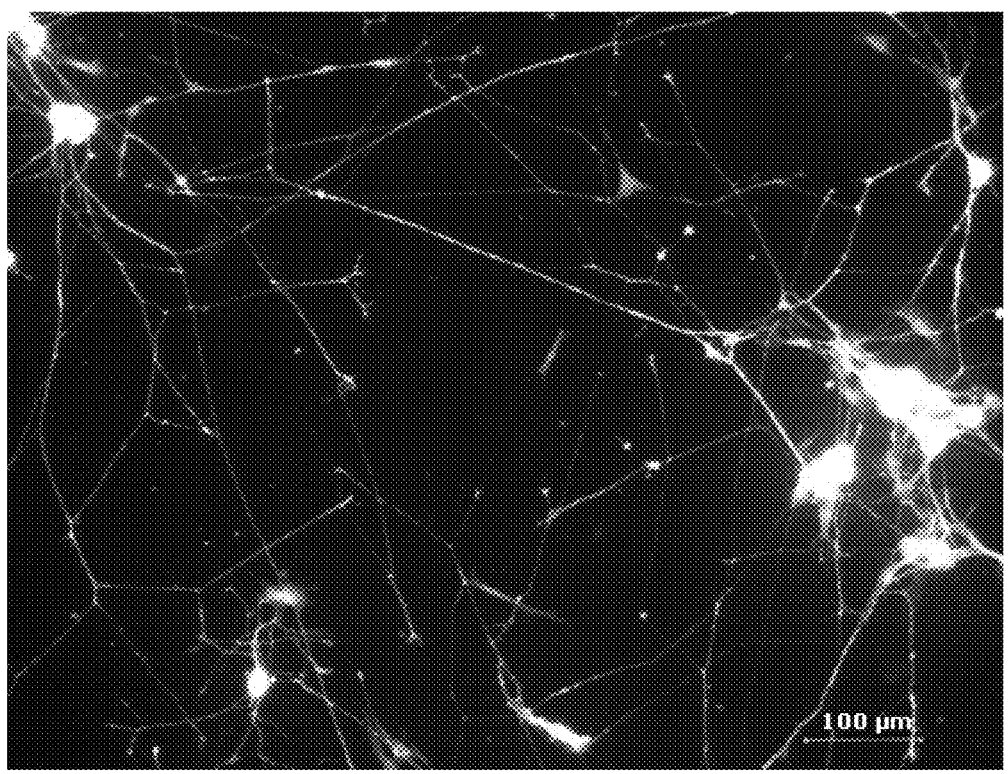
Figure 6I:
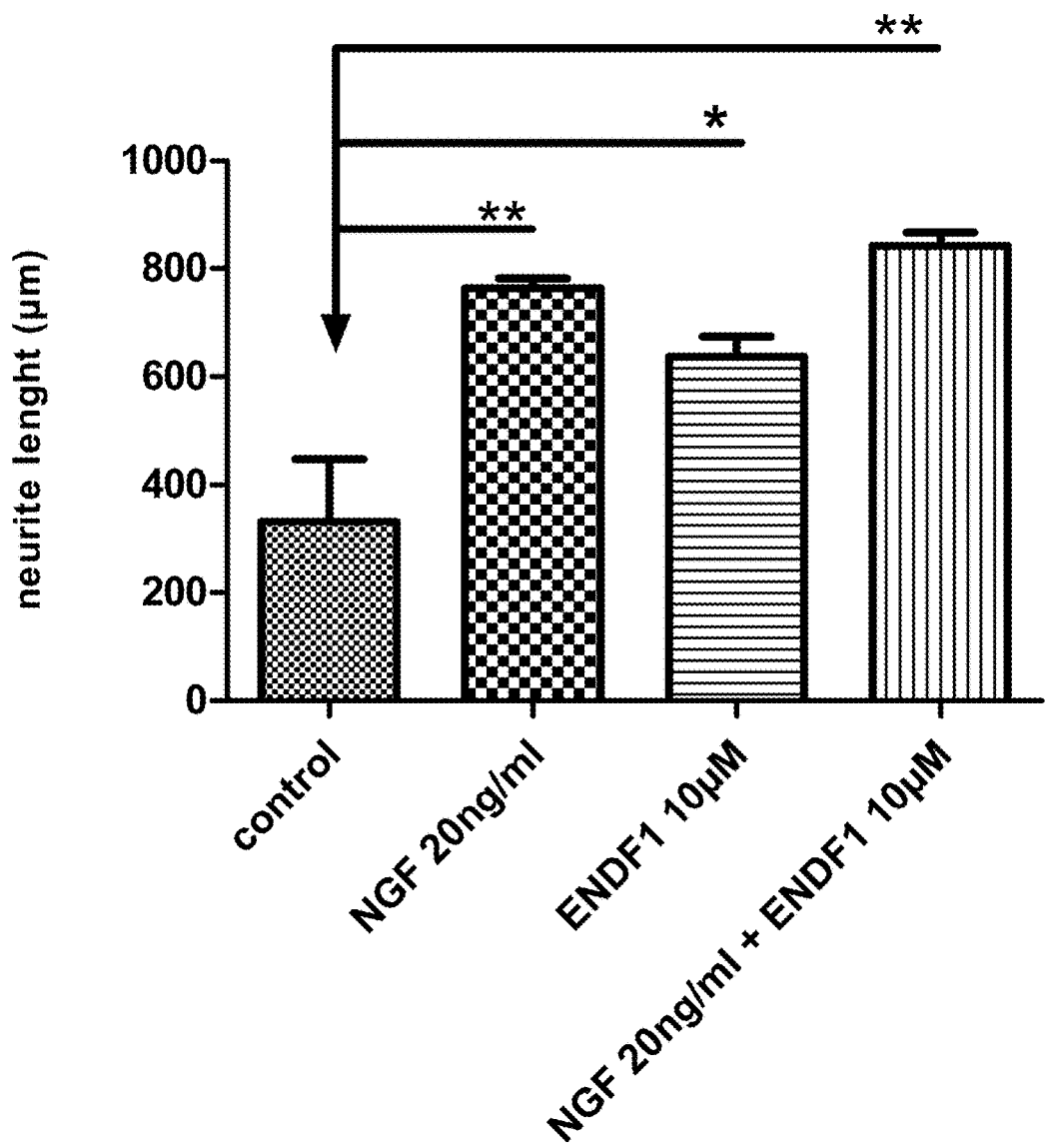

FIGS. 6A-I: Compound 1a (ENDF1) promotes neurite extension in DRG cultures. Dorsal root ganglia E8 (FIGS. 6A to 6D) and E15 (FIGS. 6E to 6H) neurons were treated for 12 to 24 hours with control medium (FIGS. 6A and 6E), 20 ng/ml NGF (FIGS. 6B and 6F), 10 µM compound 1a (ENDF1) (FIGS. 6C and 6G) or 10 µM compound 1a (ENDF1) plus 20 ng/ml NGF (FIGS. 6D and 6H), fixed and stained for GAP-43. NGF ($p<0.01$), compound 1a ($p<0.05$) and NGF plus compound 1a ($p<0.01$) strongly promote neurite extension as compared to the control (FIG. 6I). Compound 1a (ENDF1) promotes neurite extension to a similar degree as NGF. Scale: 100 µm.

Figure 7A:
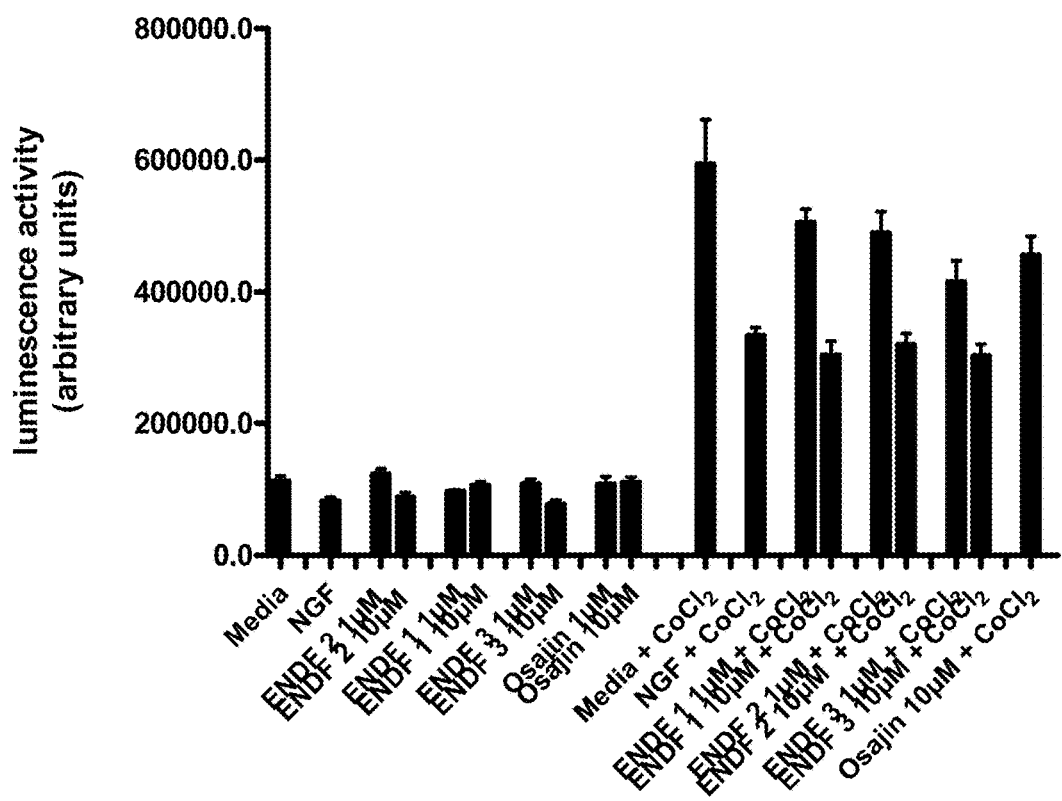
Figure 7B:
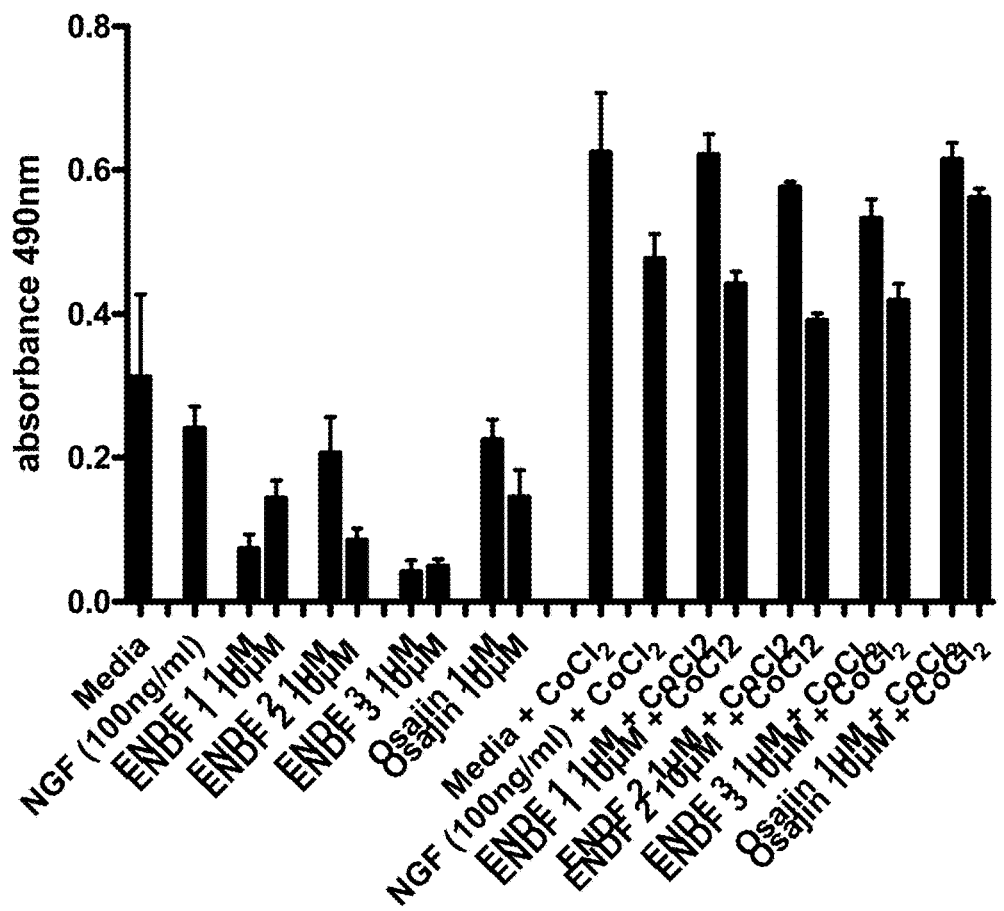

FIGS. 7A-B: ENDFs are neuroprotective. PC12 cells were stimulated for 24 hours with different substances, as described in Example 20, and Caspase 3/7 activation as well as LDH release was measured. As determined in the Caspase 3/7 assay (FIG. 7A) and the LDH release assay (FIG. 7B), the cells were partially protected from $CoCl_2$ 300 μM induced cell death by NGF, compound 1a (ENDF1), compound 1b (ENDF3) and compound 3a (ENDF2).

The invention will now be described by reference to the following examples which are merely illustrative and are not to be construed as a limitation of the scope of the present invention.

EXAMPLES

General Experimental Procedures

Microwave irradiation was carried out with CEM Discover S class single-mode synthesis system interfaced with a laptop PC running CEM synergy software monitoring the reaction. The temperature was checked by an external infrared sensor in the bottom of the cavity. Once the target temperature is reached, the microwave system automatically starts to count down the hold time. For reactions CEM vials 10 ml with snap-on caps were used. The pressure was monitored by a sensor outside the snap-on caps. The upper pressure limit was set to 18 bar. Temperature/pressure recording were attached to CEM synergy reaction files.

Column chromatography for compound purification was performed with silica gel 60 (0.06-0.2 mm) Roth (Karlsruhe) in glass-columns.

The purity of the isolated or synthesized flavonoids was estimated at 95+ % by HPLC-UV.

NMR spectra of unlabeled compounds were recorded on Bruker DBX 400 instrument. Chemical shifts are reported (δ) in ppm and coupling constants (J) in Hz.

The Shimadzu HPLC-System consisted of system controller CBM-20A, two Pumps LC-20AD, Autosampler SIL-20AC with 2 ml sample loop, Oven CTO-20AC and PDA SPD-M20A.

(±)-α-Tocopherol (96%), 2,2,5,7,8-pentamethyl-6-chromanol (97%), 3-methyl-2-butenal (SAFC), 2;3-dichloro-5,6-dicyanobenzoquinone, formic acid, ethylenediamine-N,N'-diacetic acid (Fluka) were obtained from Sigma-Aldrich (Steinheim). Osajin was purchased from Chromadex (Irvine).

Example 1: Isolation of Compounds 1a, 1b and 3a from a Xanthohumol-Rich Hop Extract A xanthohumol-rich (85%) hop extract, i.e. Xanthoflav® (DE 102 40 065 A1), supplied in different batches from Hallertauer Hopfenveredelungsgesellschaft m.b.H. was used as source material to get the following minor compounds.

The extract was dissolved in diethyl ether. The solution was washed with water. The organic layer was concentrated in vacuo. The residue was then extracted 24 hours in soxhlet apparatus with heptane. The residue was crystallized from MeOH/$H_2O$ (2/1) to decrease the xanthohumol content.

The purified extract with low xanthohumol concentration was separated by preparative RP-HPLC. The fractions were lyophilized to get the products as solids.

Separation was achieved on a Phenomenex Luna 5 C18 (2); 100 Å; 250×15 mm with a solvent gradient, starting on injection, from 43% to 91% B (acetonitrile) in A (1% aqueous formic acid) over 34 min, then to 95% B over 1 min, followed by 95% B for 2.5 min at 9.57 ml/min. The compounds were detected at 370 nm and 290 nm. The column oven temperature was 30° C. The column outlet was connected to a 16-way valve (Knauer, Berlin, K-16). The first 2 minutes the column effluent was diverted to waste. Then fractions were collected:

| | |
|---|---|
| 2.00-7.01 min | fraction 2 |
| 7.02-7.41 min | fraction 3 |
| 7.42-8.41 min | fraction 4 |
| 8.42-8.84 min | fraction 5 |
| 8.85-9.64 min | fraction 6 |
| 9.65-10.04 min | fraction 7 |
| 10.05-11.71 min | fraction 8 |
| 11.72-12.24 min | fraction 9 |
| 12.25-15.61 min | fraction 10 |
| 15.62-16.21 min | fraction 11 |
| 16.22-16.90 min | fraction 12 |
| 16.91-19.16 min | fraction 13 |
| 19.17-20.32 min | fraction 14 |
| 20.33-36.00 min | fraction 15 |

Compounds 1a (ENDF 1) and 1b (ENDF 3) are found in fraction 15. Compound 3a (ENDF 2) is found in fraction 10.

Example 2: Synthesis of (E)-1-(5-hydroxy-7-methoxy-2,2-dimethyl-2H-chromen-6-yl)-3-(4-hydroxyphenyl)prop-2-en-1-one (Compound 1a; ENDF 1)

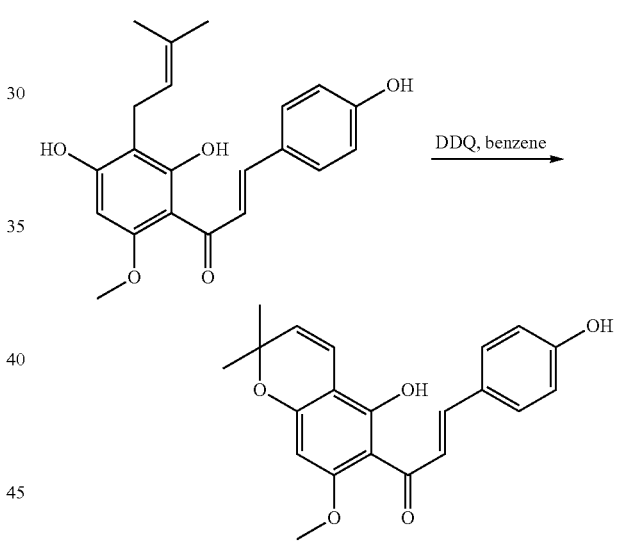

A solution of xanthohumol (200 mg, 0.56 mmol, 1 eq) and 2,3-Dichloro-5,6-dicyanobenzoquinone (Jain, Gupta, et al. Tetrahedron 1978, 34(24), 3563-3567) (128 mg, 0.56 mmol, 1 eq) in 1 ml benzene (dry) with 2 drops of dioxan was radiated in microwave at 120° C. for 3 min. Dicyanobenzoquinone (DDQ) was separated by filtration and the filtrate was concentrated in vacuo. The residue was purified by silica gel column chromatography (ethyl acetate/hexane: 2/3) to give 109.2 mg (55.4%) of a yellow solid, M=352 g/mol ($C_{21}H_{20}O_5$).

$^1$H-NMR ($CDCl_3$):

δ(ppm): 1.44 (s, 6H, 2×$CH_3$), 3.89 (s, 3H, $OCH_3$), 5.44 (d, J=11.03 Hz, 1H, H-5'), 5.9 (s, 1H, H-5"), 6.63 (d, J=11.03 Hz, 1H, H-4"), 6.84 (d, J=8.58 Hz, 2H, H-3 & H-5), 7.46 (d, J=8.58 Hz, 2H, H-2 & H-6), 7.7 (s, 2H, H-β & H-α), 14.60 (s, 1H, —OH)

$^{13}$C-NMR ($CDCl_3$):

192.8 (CO), 162.6 (C-2'), 162.5 (C-4'), 160.3 (C-6'), 157.7 (C-4), 142.4 (C-β), 130.3 (C-2 & C-6), 128.5 (C-1), 125.4

(C-5"), 125.3 (C-α), 116.1 (C-3 & C-5), 106.2 (C-1'), 103.1 (C-3'), 91.6 (C-5'), 78.3 (C-6"), 55.9 (OCH$_3$), 28.4 (C-7"& C-8")

Example 3: Synthesis of 5-hydroxy-2-(4-hydroxy-phenyl)-8,8-dimethyl-2,3,9,10-tetrahydro-8H-pyrano[2,3-f]chromen-4-one (Compound 3a; ENDF 2)

The compound 3a (ENDF2) was prepared in accordance with the method of Example 1 but using isoxanthohumol instead of xanthohumol. Purification gave 86.4 mg (43.4%) of a yellow solid, M=352 g/mol ($C_{21}H_{20}O_5$).

$^1$H-NMR (Acetone-d$_6$):
δ(ppm): 1.45 (s, 6H, 2×CH$_3$), 2.65 (d, 1H, J=13.65, H-3), 2.99 (t, 1H, H-3), 3.83 (s, 3H$_2$OCH$_3$), 5.44 (d, 1H, J=12.63 Hz, H-5"), 5.58 (d, 1H, J=10.11 Hz, H-2), 6.11 (s, 1H, H-6), 6.55 (d, 1H, J=9.86 Hz, H-4"), 6.91 (d, 2H, J=8.34 Hz, H-3' & H-5'), 7.42 (d, 2H, J=8.08 Hz H-2' & H-6')

$^{13}$C-NMR (Acetone-d$_6$):
188.25 (CO), 163.0 (C-9), 160.28 (C-7), 159.67 (C-5), 158.46 (C-4'), 131.2 (C-1'), 128.78 (C-2' & C-6'), 127.18 (C-5"), 116.7 (C3' & C5'), 116.1 (C-4"), 106.5 (C), 103.4 (C-8), 94.39 (C-6), 79.81 (C-3), 78.42 (C-6'), 56.20 (—OCH$_3$), 46.08 (C-2), 28.5 (—CH$_3$), 28.2 (—CH$_3$)

Example 4: Synthesis of (E)-1-(5-hydroxy-7-methoxy-2,2-dimethylchroman-6-yl)-3-(4-hydroxy-phenyl)prop-2-en-1-one (Compound 1b; ENDF 3)

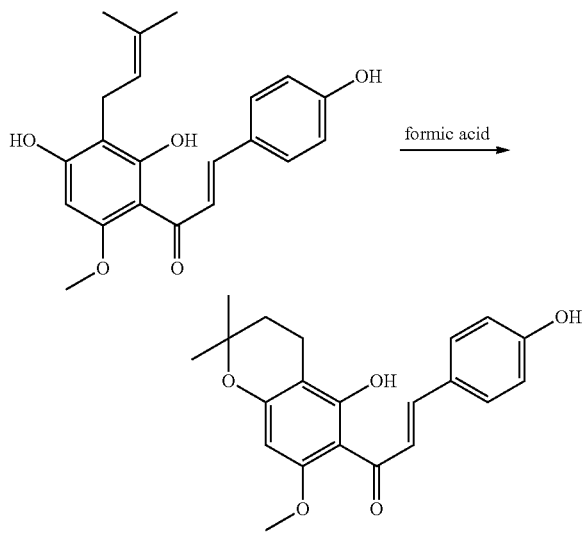

A solution of xanthohumol (200 mg, 0.56 mmol) in formic acid (2 ml) was radiated in a 10 ml microwave vial with snap-on-cap at 50° C. with pressurized air cooling for 5 min. The resulting mixture was given to ice-water. The precipitate was filtrated, washed with cold water and was purified by silica gel chromatography (ethyl acetate/hexane: 1/3) to give 75 mg (37.5%) yellow solid, M=354 g/mol ($C_{21}H_{22}O_5$).

$^1$H-NMR (CDCl$_3$):
δ(ppm): 1.35 (s, 6H, 2×CH$_3$), 1.79 (t, J=7.32 Hz, 2H, H-5"), 2.62 (t, J=6.12 Hz, 2H, H-4"), 3.86 (s, 3H, OCH$_3$), 5.88 (s, 1H, H-5'), 6.86 (d, J=8.56 Hz, 2H, H-3 & H-5), 7.47 (d, J=7.36 Hz, 2H, H-2 & H-6), 7.85 (dd, J=15.9 Hz, 2H, H-α & H-β), 14.80 (s, 1H, —OH)

$^{13}$C-NMR (CDCl$_3$):
192.39 (CO), 165.14 (C-2'), 160.53 (C-4'), 160.49 (C-4), 157.49 (C-6'), 141.91 (C-β), 129.93 (C-2 & C-6), 128.01 (C-1), 124.97 (C-α), 115.60 (C-3 & C-5), 105.26 (C-1'), 101.75 (C-5'), 91.62 (C-3'), 75.90 (C-6"), 55.35 (OCH$_3$), 31.83 (C-5") 26.38 (C-7" & C-8"), 15.76 (C-4")

Example 5: Synthesis of 1-(5-hydroxy-7-methoxy-2,2-dimethyl-2H-chromen-6-yl)-ethanone (ENDF 4)

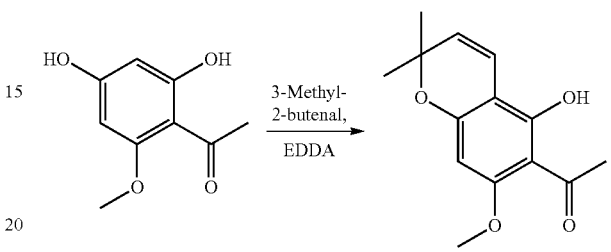

A solution of 2'4'-Dihydroxy-6'-methoxyacetophenone (100 mg, 0.55 mmol), 3-methyl-2-butenal (180.6 mg, 0.64 mmol) and ethylenediamine-N,N'-diacetic acid (EDDA) (9.89 mg, 0.05 mmol) in xylene (5 ml) was radiated in a 10 ml microwave vial with snap-on cap at 170° C. for 60 min. The reaction mixture was given to water and was extracted with ethyl acetate, washed with brine and dried over sodium sulfate. The solution was concentrated in vacuo. The residue was purified by silica gel chromatography (ethyl acetate/hexane: 4/1) to give 74.0 mg (53.5%) of a yellow solid, M=248. g/mol ($C_{14}H_{16}O_4$) (Lee, Xia. *Synthesis-Stuttgart* 2007, (20), 3240-3246).

$^1$H-NMR (acetone):
δ(ppm): 1.29 (s, 6H, 2×CH$_3$), 2.42 (s, 3H, COCH$_3$), 3.79 (s, 3H, OCH$_3$) 5.42 (d, J=9.84, 1H, Hz H-4'), 5.85 (s, 1H, H-5), 6.45 (d, J=9.88 Hz, 1H, H-5')

$^{13}$C-NMR (CDCl$_3$):
204.01 (CO), 164.21 (C-4), 162.55 (C-5), 161.21 (C-2), 126.42 (C-4'), 116.40 (C-5'), 106.21 (C-3), 103.14 (C-1), 92.14 (C-2'), 78.81 (?), 56.35 (CH$_3$), 33.09 (OCH$_3$), 28.54 (2×CH$_3$)

Example 6: Synthesis of 1-(5-hydroxy-7-methoxy-2-methyl-2-(4-methylpent-3-enyl)-2H-chromen-6-yl)ethanone This compound can be prepared in accordance with the method described in Example 5 using 3,7-dimethyl-2,6-octadienal instead of 3-methyl-2-butenal.

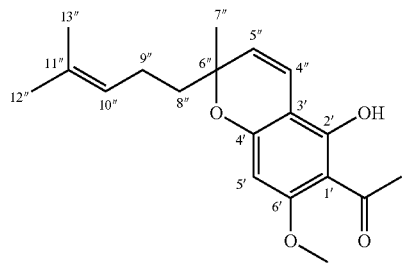 [SMILES: COc1cc2c(c(O)c1C(C)=O)C=CC(C)(CCC=C(C)C)O2]

$^1$H-NMR (d$_6$-acetone)
δ (ppm)=1.39 (s, 3H, 7"-H), 1.55 (s, 3H, 12"-H), 1.63 (s, 3H, 13"-H), 1.65-1.77 (m, 2H, 8"-H), 2.05-2.13 (m, 2H, 9"-H), 2.55 (s, 3H, CH₃), 3.92 (s, 3H, OCH₃), 5.03-5.11 (m, 1H, 10"-H), 5.51 (d, 1H, J=10.07 Hz, 5"-H), 5.99 (s, 1H, 5'-H), 6.63 (d, 1H, J=10.07 Hz, 4"-H), 14.24 (s, 1H, OH).

$^{13}$C-NMR (d$_6$-acetone)

δ (ppm)=17.62 (C-12"), 23.32 (C-9"), 25.58 (C-13"), 27.37 (C-8"), 33.13 (CH₃), 42.25 (C-7"), 56.32 (OCH₃), 81.30 (C-10"), 91.91 (C-5'), 102.91 (C-3'), 106.10 (C-1'), 116.90 (C-4"), 124.77 (C-10"), 125.26 (C-5"), 132.08 (C-11"), 161.54 (C-4'), 162.46 (C-2'), 164.22 (C-6'), 203.88 (C=O).

Example 7: Synthesis of 7-hydroxy-2-(4-hydroxyphenyl)-5-methoxy-8-(3-methyl-but-2-enyl)-chroman-4-one (Isoxanthohumol)

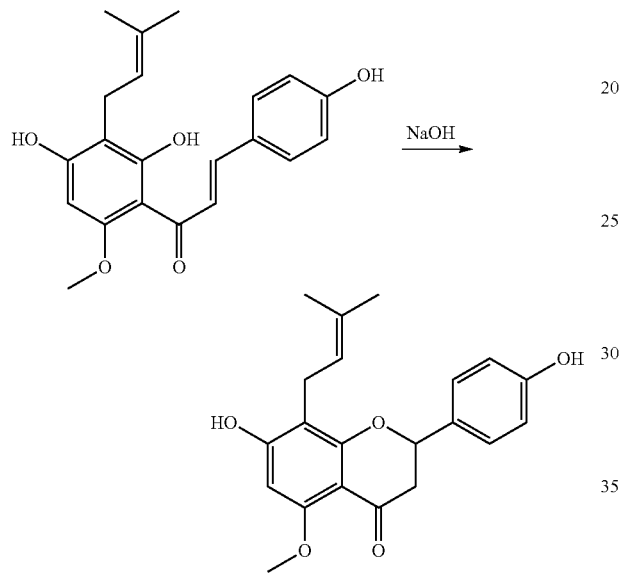

500 ml of 1% aqueous NaOH solution were cooled to 0° C. and xanthohumol (500 mg) was added. The solution was stirred for 2 h. H₂SO₄ was added to the mixture and the yellow precipitate was filtered off. After washing with cold water and crystallization from methanol the product is a light yellow solid (Wilhelm, Wessjohann. Tetrahedron 2006, 62(29), 6961-6966).

Example 8: Synthesis of 5-hydroxy-2-(4-hydroxyphenyl)-8,8-dimethyl-2,3-dihydro-8H-pyrano[3,2-g]chromen-4-one (Compound 2a; ENDF 5)

The compound was prepared in accordance with the method of Example 5 but using naringenin instead of 2'4'-Dihydroxy-6'-methoxyacetophenone. Purification gave a yellow solid, M=338 g/mol (C₂₀H₁₈O₅).

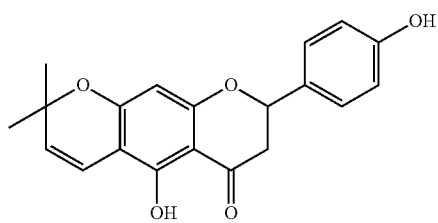 [SMILES: CC1(C)C=Cc2c(cc3c(c2O)C(=O)CC(c2ccc(O)cc2)O3)O1]

$^1$H-NMR (acetone):

δ(ppm): 1.41 (s, 6H, H-7" & H-8"), 2.75 (dd, 1H, J=16.94 Hz, H-3a), 3.19 (dd, 1H, J=13.2, H-3b) 5.47 (dd, 1H, J=13.05 Hz H-2), 5.88 (s, 1H, H-8), 6.57 (d, 1H, J=10.07 Hz, H-4"), 6.89 (d, 2H, J=8.24 Hz, H-3' & H-5'), 7.38 (d, 2H, J=8.7 Hz, H-2' & H-6')

$^{13}$C-NMR (CDCl₃):

197.70 (CO), 164.21 (C-4), 163.62 162.53 159.13 158.69 (C-8a/7/5/4')), (C-2), 130.53 (C-1'), 129.02 (C-2' & C-6'), 127.27 (C-5"), 116.14 (C-3'), 115.57 (C-5"), 103.45 (C-8), 96.52 (C-6), 79.98 (C-2), 78.91 (C-6"), 43.38 (C-3), 28.4 (2×CH₃)

Example 9: Synthesis of 5-hydroxy-2-(4-hydroxyphenyl)-8,8-dimethyl-2,3-dihydro-8H-pyrano[2,3-f]chromen-4-one (Compound 3b; ENDF 6)

This compound can be prepared in accordance with the method described in Example 5, using naringenin instead of 2'4'-dihydroxy-6'-methoxyacetophenone and purifying the title compound.

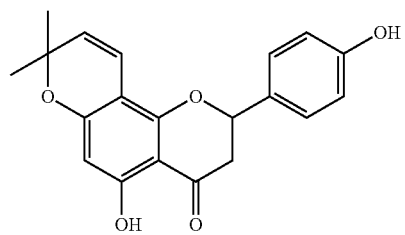 [SMILES: CC1(C)C=Cc2c(cc(O)c3c2OC(c2ccc(O)cc2)CC3=O)O1]

$^1$H-NMR (d$_6$-acetone):

δ (ppm)=1.39 (s, 3H, H-7"), 1.42 (s, 3H, H-8"), 2.77 (dd, 1H, J=17.4 Hz, H-3a), 3.20 (dd, 1H, J=16.94 Hz, H-3b), 5.50 (dd, 1H, J=13.05=Hz, H-2), 5.58 (d, 1H, J=10.07, H-5"), 5.87 (s, 1H, H-6), 6.49 (d, 1H, J=10.07 Hz, H-4"), 6.90 (dd, 2H, J=8.7 Hz, H-3' & H-5'), 7.41 (d, 2H, J=8.7 Hz, H-2' & H-6'), 8.59 (s, 1H, OH-4'), 12.24 (s, 1H, OH-5)

$^{13}$13-NMR (d$_6$-acetone):

δ (ppm)=197.61 (C-4), 164.61 (C-5), 162.65 (C-7), 158.69 (C-4'), 158.02 (C-8a), 130.50 (C-1'), 128.92 (C-2' & C-6'), 127.33 (C-5"), 116.19 (C-3' & C-5'), 116.17 (C-4"), 103.51 (C-4a), 102.50 (C-8), 97.50 (C-6), 80.03 (C-2), 78.78 (C-6"), 43.22 (C-3), 28.56 (C-7"), 28.29 (C-8")

Example 10: Synthesis of (2E)-1-(5-Hydroxy-7-methoxy-2-methyl-2-(4-methylpent-3-enyl)-2H-chromen-6-yl)-3-(4-(methoxymethoxy)phenyl)prop-2-en-1-one 1.5 ml of an aqueous solution of potassium hydroxide (50%) was poured to a solution of 1.00 mmol 1-(5-hydroxy-7-methoxy-2-methyl-2-(4-methylpent-3-enyl)-2H-chromen-6-yl)ethanone (Example 6) and 1.20 mmol 4-(methoxymethoxy)benzaldehye in 13 ml methanol. The reaction mixture was heated to boiling point for 3 hours. After cooling to room temperature the reaction mixture was poured into 20 ml water, acidified with HCl (10%) and extracted three times with 15 ml ethyl acetate. The combined organic fractions were dried over sodium sulfate and concentrated in vacuo. The residue was purified by silica gel chromatography (n-hexane/ethyl acetate 2/1).

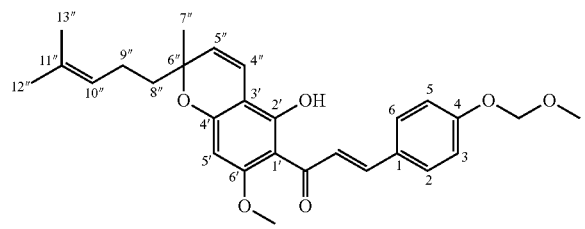 [SMILES: COCOc1ccc(/C=C/C(=O)c2c(OC)cc3c(c2O)C=CC(C)(CCC=C(C)C)O3)cc1]

The yellow product was directly deprotected in accordance with the method described in Example 14 below in order to give the title compound.

Example 11: Synthesis of (2E)-3-(3,4-bis(methoxymethoxy)phenyl)-1-(5-hydroxy-7-methoxy-2,2-dimethyl-2H-chromen-6-yl)prop-2-en-1-one This compound can be prepared in accordance with the method described in Example 10 using ENDF4 and 3,4-bis(methoxymethoxy)benzaldehyde.

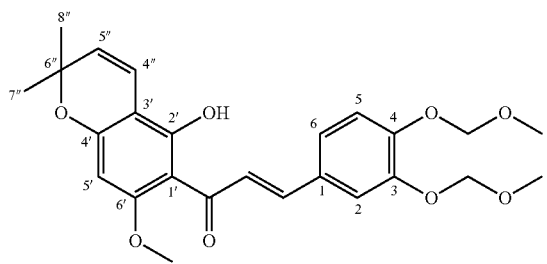

The yellow product was directly deprotected in accordance with the method described in Example 14 below in order to give the title compound.

Example 12: Synthesis of (2E)-3-(benzo[d][1,3]dioxol-6-yl)-1-(5-hydroxy-7-methoxy-2,2-dimethyl-2H-chromen-6-yl)prop-2-en-1-one (Compound 1f; ENDF 11)

This compound can be prepared in accordance with the method described in Example 10 using ENDF4 and benzo[1,3]dioxole-5-carbaldehyde.

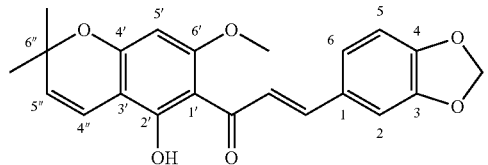 [SMILES: COc1cc2c(c(O)c1C(=O)/C=C/c1ccc3c(c1)OCO3)C=CC(C)(C)O2]

$^1$H-NMR (d$_6$-acetone)
δ (ppm)=1.43 (s, 6H, 7"-H & 8"-H), 4.00 (s, 3H, OCH$_3$), 5.56 (d, 1H, J=10.26 Hz, 5"-H), 6.02 (s, 1H, 5'-H), 6.08 (s, 2H, O—CH$_2$—O), 6.61 (d, 1H, J=10.26 Hz, 4"-H) 6.91 (d, 1H, J=8.30 Hz, 5-H), 7.23 (d, 1H, J=1.47 Hz, 2-H), 7.27 (dd, 2H, J=8.30 Hz, 6-H), 7.70 (d, 1H, J=15.63 Hz, β-H), 7.85 (d, 1H, J=15.63 Hz, α-H), 14.68 (s, 1H, OH).

$^{13}$C-NMR (d$_6$-acetone)
δ (ppm)=28.51 (C-7"& C-8"), 56.60 (OCH$_3$), 78.66 (C-6"), 92.45 (C-5"), 102.68 (O—CH$_2$—O), 103.37 (C-3'), 106.54 (C-1'), 107.38 (C-6), 109.35 (C-5), 116.46 (C-4"), 126.01 (C-6), 126.27 (C-α), 126.40 (C-5"), 130.80 (C-1), 143.29 (C-β), 149.45 (C-4), 150.74 (C-3), 161.26 (C-4'), 163.20 (C-2"), 163.81 (C-6"), 193.37 (C=O).

Example 13: Synthesis of (2E)-1-(5-hydroxy-7-methoxy-2,2-dimethyl-2H-chromen-6-yl)-3-(4-hydroxyphenyl)prop-2-en-1-one (Compound 1d; ENDF 9)

This compound can be prepared in accordance with the method described in Example 10 using ENDF4 and 4-methoxybenzaldehyde.

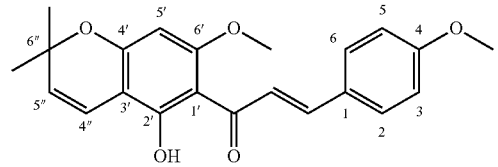

$^1$H-NMR (d$_6$-acetone)
δ (ppm)=1.43 (s, 6H, 7"-H & 8"-H), 3.86 (s, 3H, OCH$_3$), 4.00 (s, 3H, OCH$_3$), 5.56 (d, 1H, J=10.26 Hz, 5"-H), 6.02 (s, 1H, 5'-H), 6.61 (d, 1H, J=10.26 Hz, 4"-H), 7.00 (d, 2H, J=8.79 Hz, 3-H & 5-H), 7.69 (d, 2H, J=8.79 Hz, 2-H & 6-H), 7.77 (d, 1H, J=15.63 Hz, β-H), 7.89 (d, 1H, J=15.63 Hz, α-H), 14.75 (s, 1H, OH).

$^{13}$C-NMR (d$_6$-acetone)
δ (ppm)=28.51 (C-7"& C-8"), 55.76 (OCH$_3$), 56.56 (C-4), 78.85 (C-6"), 92.45 (C-5'), 103.40 (C-3'), 106.53 (C-1'), 115.31 (C-3 & C-5), 116.48 (C-4"), 125.75 (C-α), 126.39 (C-5"), 128.93 (C-1), 131.16 (C-2 & C-6), 143.35 (C-β), 161.20 (C-4), 162.64 (C-6'), 163.26 (C-4'), 163.78 (C-2'), 193.43 (C=O).

Example 14: Synthesis of (2E)-1-(5-hydroxy-7-methoxy-2-methyl-2-(4-methylpent-3-enyl)-2H-chromen-6-yl)-3-(4-hydroxyphenyl)prop-2-en-1-one (Compound 1g; ENDF 7)

Five drops of aqueous HCl (3M) were poured to 10 ml of a methanolic solution of (2E)-1-(5-Hydroxy-7-methoxy-2-methyl-2-(4-methylpent-3-enyl)-2H-chromen-6-yl)-3-(4-(methoxymethoxy) phenyl)prop-2-en-1-one (Example 10) and was heated to 50° C. for 60 minutes. After cooling the reaction mixture was poured into 15 ml water and extracted three times with 15 ml ethyl acetate. The combined organic fractions were dried over sodium sulfate and concentrated in vacuo.

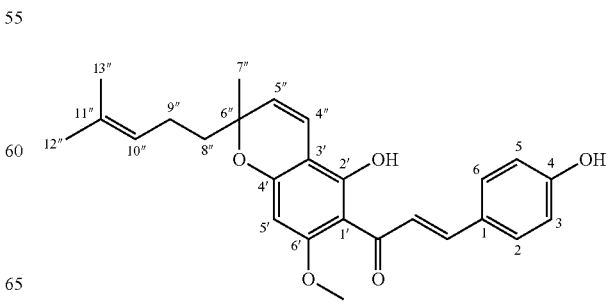

¹H-NMR (d₆-acetone)

δ (ppm)=1.41 (s, 3H, 7"-H), 1.60 (s, 3H, 12"-H), 1.63 (s, 3H, 13"-H), 1.65-1.79 (m, 2H, 8"-H), 2.10-2.14 (m, 1H, 9"-H), 4.00 (s, 3H, OCH₃), 5.12 (t, 1H, J=6.84 Hz, 10"-H), 5.53 (d, 1H, J=10.26 Hz, 5"-H), 6.04 (s, 1H, 5'-H), 6.67 (d, 1H, J=9.77 Hz, 4"-H), 6.91 (d, 2H, J=8.79 Hz, 3-H & 5-H), 7.61 (d, 2H, J=8.30 Hz, 2-H & 6-H), 8.94 (s, 1H, 4-OH), 14.82 (s, 1H, 2'-OH).

¹³C-NMR (d₆-acetone)

δ (ppm)=17.62 (C-12"), 23.34 (C-8"), 25.76 (C-13"), 27.39 (C-7"), 42.26 (C-9"), 56.54 (OCH₃), 81.33 (C-10"), 92.23 (C-5'), 103.22 (C-3'), 106.43 (C-1'), 116.78 (C-3 & C-5), 117.07 (C-4"), 124.79 (C-10"), 125.00 (C-5"), 125.14 (C-α), 127.95 (C-1), 131.34 (C-2 & C-6), 132.06 (C-11"), 143.75 (C-β), 160.71 (C-4), 161.47 (C-4'), 163.24 (C-2'), 163.79 (C-6'), 193.36 (C=O).

Example 15: Synthesis of (2E)-1-(5-Hydroxy-7-methoxy-2,2-dimethyl-2H-chromen-6-yl)-3-(3,4-dihydroxyphenyl)prop-2-en-1-one (Compound 1e; ENDF10)

This compound can be prepared in accordance with the method described in Example 14 using (2E)-3-(3,4-bis(methoxymethoxy)phenyl)-1-(5-hydroxy-7-methoxy-2,2-dimethyl-2H-chromen-6-yl)prop-2-en-1-one (Example 11) instead of the compound of Example 10.

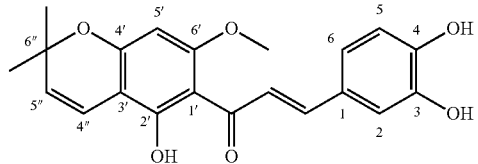

¹H-NMR (d₆-acetone)

δ (ppm)=1.42 (s, 6H, 7"-H & 8"-H), 3.99 (s, 3H, OCH₃), 5.55 (d, 1H, J=10.26 Hz, '5"-H), 6.02 (s, 1H, 5'-H), 6.61 (d, 1H, J=10.26 Hz, 4"-H), 6.88 (1H, d, J=7.82 Hz, 5-H), 7.11 (dd, 1H, J=8.30 Hz, 6-H), 7.24 (d, 1H, J=1.95 Hz, 2-H), 7.69 (d, 1H, J=15.63 Hz, β-H), 7.81 (d, 1H, J=15.63 Hz, α-H), 14.81 (s, 1H, OH).

C-¹³C-NMR (d₆-acetone)

δ (ppm)=28.51 (C-7"& C-8"), 56.55 (OCH₃), 78.81 (C-6"), 92.44 (C-5'), 103.42 (C-3'), 106.53 (C-1'), 115.33 (C-5), 116.50 (C-4"), 123.20 (C-6), 125.70 (C-α), 126.36 (C-5"), 128.60 (C-1), 144.18 (C-β), 146.35 (C-4), 149.00 (C-3), 161.08 (C-4'), 163.27 (C-2'), 163.74 (C-6'), 193.41 (CO).

Example 16: Synthesis of 1-(5-hydroxy-7-methoxy-2,2-dimethylchroman-6-yl)-3-(4-hydroxyphenyl)propan-1-one (Compound 1c; ENDF8)

122.0 mg (E)-1-(5-hydroxy-7-methoxy-2,2-dimethyl-chroman-6-yl)-3-(4-hydroxyphenyl)prop-2-en-1-one (ENDF3) were diluted in 7 ml methanol. After addition of 15 mg Pd/C, hydrogen was passed through the reaction mixture. The residue was purified by silica gel chromatography (n-hexane/ethyl acetate 1/1) to give the product.

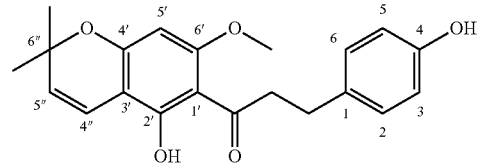

¹H-NMR (d6-acetone)

δ (ppm)=1.31 (s, 6H, 7"-H & 8"-H), 1.80 (t, 2H, J=6.84 Hz, 5"-H), 2.54 (t, 2H, J=6.84 Hz, 4"-H), 2.86 (t, 2H, J=8.30 Hz, former β), 3.25 (t, 2H, J=7.82 Hz, former α), 3.86 (s, 3H, OCH₃), 5.90 (s, 1H, 5'-H), 6.75 (d, 2H, J=8.79 Hz, 3-H & 5-H), 7.08 (d, 2H, J=8.30 Hz, 2-H & 6-H), 14.42 (s, 1H, OH).

¹³C-NMR (d6-aceton)

δ (ppm)=16.68 (C-4"), 26.85 (C-7"& C-8"), 30.75 (former β), 32.61 (C-5"), 46.94 (former α), 56.05 (OCH₃), 76.64 (C-6"), 92.39 (C-3'), 102.31 (C-5'), 105.45 (C-1'), 115.99 (C-3 & C-5), 130.15 (C-2 & C-6), 133.33 (C-1), 156.42 (C-4), 161.66 (C-4'), 161.99 (C-6'), 165.57 (C-2'), 205.46 (CO).

Biological Assays

In the following examples, primary cells derived from developing mouse brain, primary chicken embryonic day 8 and day 16 dorsal root ganglion neurons, the mouse Neuro-2a neuroblastoma cell line and the rat phaeochromocytoma PC12 cell line were used to test the activity of chromane-like cyclic prenylflavonoids and other substances to enhance neuronal differentiation, survival and neuroregeneration.

The following substances were tested:

Compound 1a (ENDF1): (E)-1-(5-hydroxy-7-methoxy-2,2-dimethyl-2H-chromen-6-yl)-3-(4-hydroxyphenyl)prop-2-en-1-one.

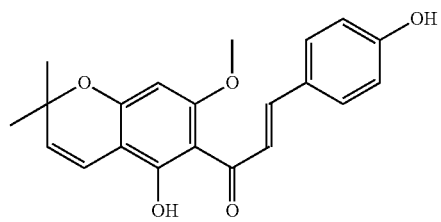 [SMILES: COc1cc2c(c(O)c1C(=O)/C=C/c1ccc(O)cc1)C=CC(C)(C)O2]

Compound 1b (ENDF3): (E)-1-(5-hydroxy-7-methoxy-2,2-dimethylchroman-6-yl-3-(4-hydroxyphenyl)prop-2-en-1 one.

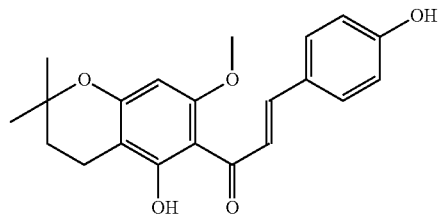 [SMILES: COc1cc2c(c(O)c1C(=O)/C=C/c1ccc(O)cc1)CCC(C)(C)O2]

Compound 1c (ENDF8): 1-(5-hydroxy-7-methoxy-2,2-dimethylchroman-6-yl)-3-(4-hydroxyphenyl)propan-1-one.

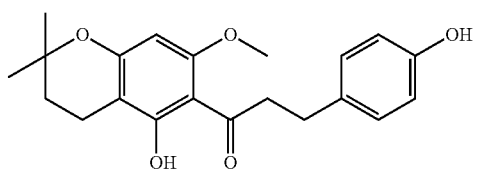 [SMILES: COc1cc2c(c(O)c1C(=O)CCc1ccc(O)cc1)CCC(C)(C)O2]

Compound 1d (ENDF9): (2E)-1-(5-hydroxy-7-methoxy-2,2-dimethyl-2H-chromen-6-yl)-3-(4-hydroxyphenyl)prop-2-en-1-one.

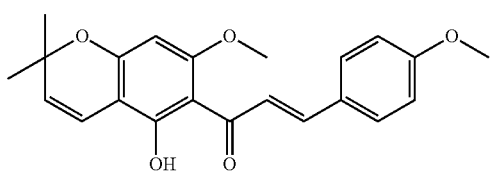

Compound 1e (ENDF10): (2E)-1-(5-Hydroxy-7-methoxy-2,2-dimethyl-2H-chromen-6-yl)-3-(3,4-dihydroxyphenyl)prop-2-en-1-one.

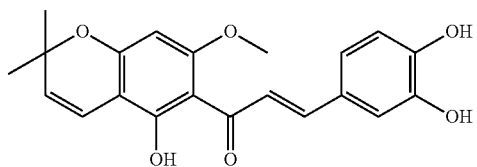 [SMILES: COc1cc2c(c(O)c1C(=O)/C=C/c1ccc(O)c(O)c1)C=CC(C)(C)O2]

Compound 1f (ENDF11): (2E)-3-(benzo[d][1,3]dioxol-6-yl)-1-(5-hydroxy-7-methoxy-2,2-dimethyl-2H-chromen-6-yl)prop-2-en-1-one.

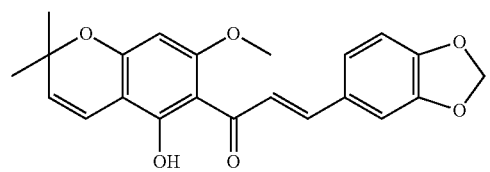 [SMILES: COc1cc2c(c(O)c1C(=O)/C=C/c1ccc3c(c1)OCO3)C=CC(C)(C)O2]

Compound 1g (ENDF7): (2E)-1-(5-hydroxy-7-methoxy-2-methyl-2-(4-methylpent-3-enyl)-2H-chromen-6-yl)-3-(4-hydroxyphenyl)prop-2-en-1-one.

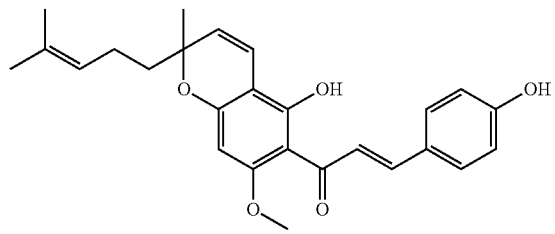 [SMILES: COc1cc2c(c(O)c1C(=O)/C=C/c1ccc(O)cc1)C=CC(C)(CCC=C(C)C)O2]

Compound 2a (ENDF5): 5-Hydroxy-2-(4-hydroxy-phenyl)-8,8-dimethyl-2,3-dihydro-8H-pyrano[3,2-g]chromen-4-one.

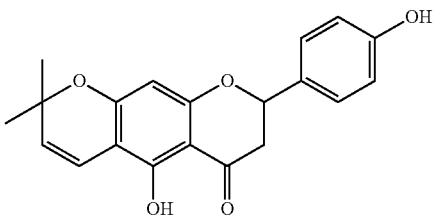 [SMILES: CC1(C)C=Cc2c(cc3c(c2O)C(=O)CC(c2ccc(O)cc2)O3)O1]

Compound 3a (ENDF2): 5-Hydroxy-2-(4-hydroxy-phenyl)-8,8-dimethyl-2,3,9,10-tetrahydro-8H-pyrano[2,3 f]chromen-4-one.

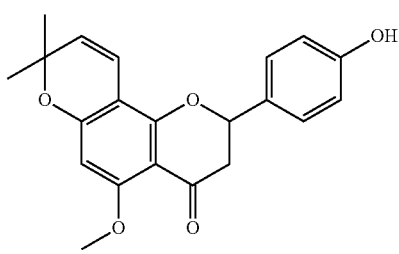 [SMILES: COc1cc2c(c3c1C(=O)CC(c1ccc(O)cc1)O3)C=CC(C)(C)O2]

Compound 3b (ENDF6): 5-Hydroxy-2-(4-hydroxy-phenyl)-8,8-dimethyl-2,3-dihydro-8H-pyrano[2,3-f]chromen-4-one.

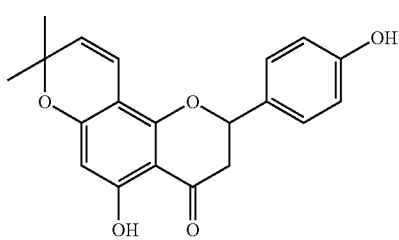 [SMILES: CC1(C)C=Cc2c(cc(O)c3c2OC(c2ccc(O)cc2)CC3=O)O1]

ENDF4: 1-(5,7-dihydroxy-2,2-dimethyl-2H-chromen-6-yl)ethanone.

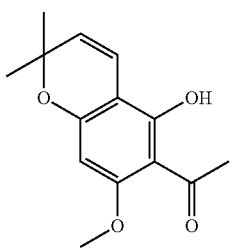 [SMILES: COc1cc2c(c(O)c1C(C)=O)C=CC(C)(C)O2]

Xanthohumol: (E)-1-(2,4-dihydroxy-6-methoxy-3-(3-methylbut-2-en-1-yl)phenyl)-3-(4-hydroxyphenyl)prop-2-en-1-one.

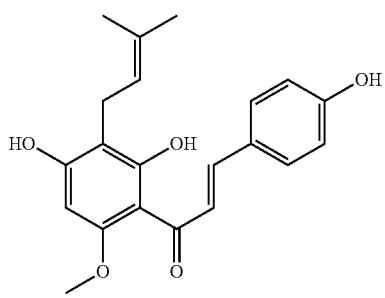 [SMILES: COc1cc(O)c(CC=C(C)C)c(O)c1C(=O)/C=C/c1ccc(O)cc1]

Isoxanthohumol: 7-hydroxy-2-(4-hydroxyphenyl)-5-methoxy-8-(3-methylbut-2-en-1-yl)chroman-4-one.

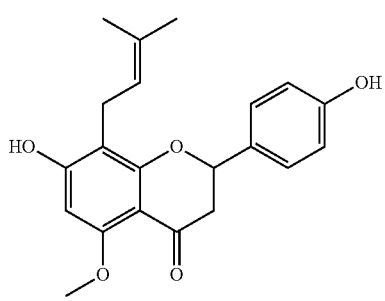 [SMILES: COc1cc(O)c(CC=C(C)C)c2c1C(=O)CC(c1ccc(O)cc1)O2]

Osajin: 5-hydroxy-3-(4-hydroxyphenyl)-8,8-dimethyl-6-(3-methylbut-2-enyl)pyrano[2,3-h]chromen-4-one.

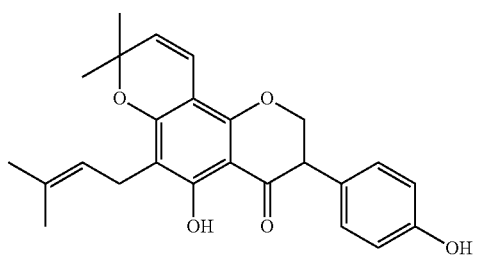 [SMILES: CC(C)=CCc1c(O)c2c(c3c1OC(C)(C)C=C3)OCC(c1ccc(O)cc1)C2=O]

6-Prenylnaringenin: 5,7-dihydroxy-2-(4-hydroxyphenyl)-6-(3-methylbut2-en-1yl)chroman-4-one.

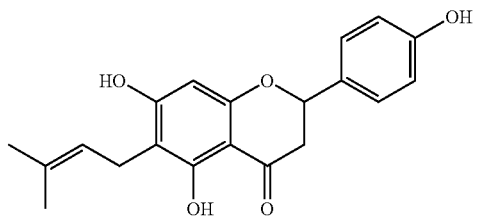 [SMILES: CC(C)=CCc1c(O)cc2c(c1O)C(=O)CC(c1ccc(O)cc1)O2]

8-Prenylnaringenin: 5,7-dihydroxy-2-(4-hydroxyphenyl)-8-(3-methylbut2-en-1yl)chroman-4-one.

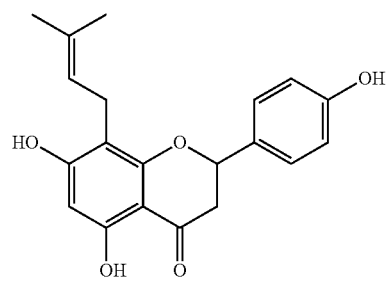 [SMILES: CC(C)=CCc1c(O)cc(O)c2c1OC(c1ccc(O)cc1)CC2=O]

Chromanol: 2,2,5,7,8-Pentamethyl-6-chromanol.

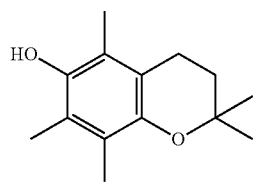 [SMILES: Cc1c(C)c2c(c(C)c1O)CCC(C)(C)O2]

Tocopherol: 2,5,7,8-tetramethyl-2-(4,8,12 trimethyltridecyl)chroman-6-ol.

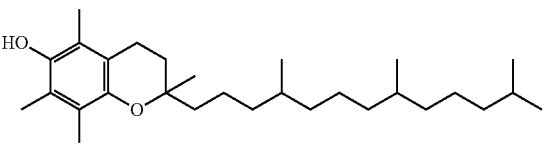 [SMILES: Cc1c(C)c2c(c(C)c1O)CCC(C)(CCCC(C)CCCC(C)CCCC(C)C)O2]

Retinoic acid: (2E,4E,6E,8E)-3,7-dimethyl-9-(2,6,6-trimethylcyclohexen-1-yl)nona-2,4,6,8-tetraenoic acid.

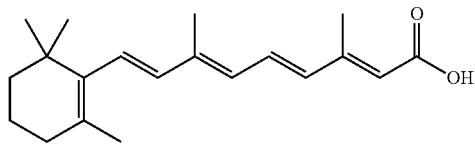 [SMILES: CC1=C(/C=C/C(C)=C/C=C/C(C)=C/C(=O)O)C(C)(C)CCC1]

Valproic acid: 2-propylpentanoic acid.

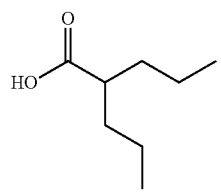

Stock solutions for the substances were 100 mM in DMSO. All trans-retinoic acid 10 µM+valproic acid sodium salt 50 µM (Sigma-Aldrich, Taufkirchen, Germany) diluted in DMEM-KO medium or Neurobasal medium+1% FCS were used as positive control. DMEM-KO medium or NB-B27+1% FCS was used as negative control.

Readouts were the abilities i) to induce the promoter of the neuronal precursor specific gene doublecortin (DCX) in a firefly-luciferase assay using primary fetal mouse brain derived cells (Karl, 2005), ii) to promote neuronal differentiation/neurite extension in different neuronal cells, iii) to promote neurite extension in a fetal chicken dorsal root ganglion neurite outgrowth assay (Aigner, 1993; Aigner, 1995), and iv) to promote neuronal survival in a PC12 cobalt-chloride stress test (Wang, 2000).

Experiments were performed in triplicates or tetraplicates and p-values of 0.05 to 0.001 were considered to be significant. Data are presented as mean+/−SD. Statistical analysis was performed using PRISM5 (GraphPad, San Diego, Calif., USA) and significance was acquired by one-way ANOVA-Tukey post hoc.

Example 17: The Chromane-Like Cyclic Prenylflavonoids According to the Invention Activate a Neuronal Differentiation Program Chromane-like cyclic prenylflavonoids, including the compounds 1a to 1g, 2a, 3a and 3b according to the invention, were tested for their ability to induce the promoter of the neuronal precursor specific gene doublecortin (DCX) in a firefly-luciferase assay using primary fetal mouse brain derived cells (Karl, 2005) in Neurobasal plus 1% FCS.

Neuronal Stem Cell (NSC) Isolation from Mouse Embryonic Forebrain (MEF E16) Cultures Primary mouse embryonic day 16 forebrain (MEF) cultures were prepared as follows. Pregnant NMRI mice (Charles River Laboratories, Sulzfeld, Germany) were sacrificed and the uteri promptly removed and immersed in ice-cold Dulbecco's phosphate buffered saline solution—DPBS (PAA, Pasching, Austria). Eight embryonic day (E) 16 embryos were released from the uteri; forebrains were taken out, separated from surrounding tissues and mechanically dissociated using a razor blade. Subsequently the dissociated cells were collected by 5 min centrifugation at 120×g. The pellet was resuspended in 10 ml PPD-solution containing 0.01% papain (Worthington, England), 0.1% Dispasell (Roche, Basel, Switzerland), 0.01% DNaseI (Worthington, England), 12.4 mM $MgSO_4$ dissolved in HBSS w/o Ca/Mg (PAA, Pasching, Austria). The cell suspension was incubated at 37° C. and triturated every ten minutes for three times. The cell suspension was then centrifuged at 120×g for 5 minutes and washed three times in Neurobasal medium (Gibco BRL, Germany) supplemented with 2% (v/v) B27 (Gibco BRL, Karlsruhe), 2 mM L-glutamine, 100 µg/ml Penicillin/Streptomycin (PAN Biotech GmbH, Aidenbach, Germany). Finally, the cell preparation was resuspended in 12 ml Neurobasal medium supplemented with B27 (Gibco BRL, Karlsruhe), 2 mM L-glutamine, 100 µg/ml Penicillin/Streptomycin (PAN Biotech GmbH, Aidenbach, Germany), 20 ng/ml Epidermal Growth Factor—rhEGF, 20 ng/ml Fibroblast Growth Factor—rhFGF (R&D Systems, Wiesbaden-Nordenstadt, Germany) and 2 µg/ml Heparin (Sigma-Aldrich, Taufkirchen, Germany) (NB plus all), seeded in one T75 flask (TPP, Switzerland) and maintained in a humidified atmosphere at 37° C. and 5% $CO_2$. Within the first two days in culture, MEF cells had formed neurospheres. On this day (day 2), half of the medium was refreshed and on day 4 cells were passaged. To passage the cells, the culture medium containing the floating neurospheres was collected in a 15 ml tube (Corning, Lowell, USA) and centrifuged at 120×g for 5 min. For dissociation, the pellet was resuspended in 500 µl Accutase (PAA, Pasching, Austria) and triturated using a 1 ml pipette. The cell suspension was incubated at 37° C. for 10 min, and then, 10 ml media were added. Cell number was determined by Trypan blue exclusion.

Luciferase Assay

Luciferase assays were performed using a noncommercial dual luciferase enzyme assay system (Dyer et al., 2000, Anal Biochem). In this system, a co-transfection with pDCX-Luci and a control vector driving Renilla-luciferase under the CMV promoter was performed. The two different luciferases have different specific substrates and, therefore, the DCX regulatory region driven firefly luciferase activity can be distinguished from CMV driven Renilla-luciferase. For analysis, the firefly luciferase activity was normalized against the CMV driven Renilla-luciferase. For each transfection reaction, a volume containing two million cells was transferred into a 15 ml tube (Corning, Lowell, USA), centrifuged at 120×g for 5 min to pellet the cells and resuspended in 100 µl Amaxa Mouse Neural Stem Cell Nucleofector Kit (Lonza, Kln, Germany). Then, pDCX-Luci (Karl, 2005) and pRL3 (Promega, Mannheim, Germany) (5 µg each) were added and the entire reaction mix was transferred into an Amaxa transfection cuvette. Transfection was done using the A-033 program in the Amaxa Nucleofector II (Lonza, Kln, Germany). Transfected cells were then pipetted into 20 ml of DMEM knockout medium (Gibco BRL, Germany) containing 20% serum replacement supplement (PAN Biotech GmbH, Aidenbach, Germany), 2 mM L-glutamine (PAN Biotech GmbH, Aidenbach, Germany) and 100 µg/ml Penicillin/Streptomycin (PAN Biotech GmbH, Aidenbach, Germany) (DMEM-KO plus supplements) in a 50 ml tube (Corning, Lowell, USA). From this resulting cell suspension, 200 µl per well were plated in Poly-Ornithine/Laminin coated 96-well-luciferase plates (Wimmer & Macho, Wels, Austria) in a cell density of 20.000 cells per well, as described herein below. For some experiments, cells were taken up after transfection and further cultivated in Neurobasal medium (Gibco BRL, Germany) supplemented with 2% (v/v) B27 (Gibco BRL, Karlsruhe) and 1% fetal calf serum (PAN Biotech, Aidenbach, Germany), 2 mM L-glutamine, 100 µg/ml Penicillin/Streptomycin (PAN Biotech, Aidenbach, Germany) (NB-B27, 1% FCS) instead of DMEM-KO plus supplement.

For coating of the 96-well-luciferase plates, wells were incubated for one hour at 37° C. with Poly-Ornithine 100 µg/ml in sterile $H_2O$. After three times of washing with sterile $H_2O$ the wells were coated with Laminin (Sigma-Aldrich, Taufkirchen, Germany) (5 µg/ml in DPBS) for two hours at 37° C. Immediately after removing Laminin, cells were plated.

Substances were tested in 0.1 µM, 1 µM, 10 µM and 100 µM final concentrations in DMEM-KO plus supplement or NB-B27, 1% FCS. Cells were stimulated starting one day after seeding for a total of three days by replacing the medium with 200 µl fresh medium containing the various substances. Stimulations were done in 4 wells/condition (tetraplicates) at 37° C. in 5% $CO_2$ containing humidified atmosphere.

Prior to measurement the stimulation medium was carefully taken off with a pipette. Cells were then lysed in 25 µl lysis solution consisting of 25 mM Tris-phosphate pH 7.8, 2 mM DTT, 1% Triton X-100 (Sigma-Aldrich, Taufkirchen, Germany), 2 mM EDTA, 10% Glycerol (Merck, Darmstadt, Germany) per well for ten minutes. For analysis of the firefly luciferase activity, 80 µl of 25 mM glycylglycine (Acros, Geel, Belgium), 15 mM $KH_2PO_4$ pH 8.0, 4 mM EGTA, 15 mM $MgSO_4$ (Merck, Darmstadt, Germany), 2 mM ATP, 1 mM DTT, 0.1 mM Coenzyme A, 75 mM luciferin (Sigma-Aldrich, Taufkirchen, Germany) were added to each well and the bioluminescent measurement is performed in a Victor™ X Multilable Plate Reader (Perkin Elmer, Calif., USA) according to the manufacturer's instructions. Then, 100 μl of freshly prepared Renilla assay solution consisting of 1.1 M NaCl (VWR, Vienna, Austria), 2.2 mM $Na_2EDTA$, 0.22 M $KH_2PO_4$ pH 5.1 (Merck, Darmstadt, Germany), 0.44 mg/mL BSA (Biomol, Hamburg, Germany), 1.3 mM $NaN_3$ (Sigma-Aldrich, Taufkirchen, Germany), 1.43 mM coelenterazine (p.j.k., Kleinblittersdorf, Germany) per well were added and measurements were performed using the Victor™ X Multilable Plate Reader as described above. Data were normalized the following way: i) firefly (FF) luciferase activity is related to the renilla (R) luciferase activity; and ii) the FF/R values of the individual samples are related to the FF/R value obtained by stimulation with the control medium and expressed as x-fold change compared to control. The renilla luciferase activity values (R values) obtained for the test substances were furthermore related to the R value obtained by stimulation with control medium (i.e., $R_{substance}/R_{control}$) to give normalized renilla activity values which, supposing a constant number of transfected cells, provide an approximate measure of the test substances' effect on cell survival and, thus, their relative cytotoxicities.

Results

Among all substances tested, the compounds 1a ("ENDF1"), 1b ("ENDF3"), 1c ("ENDF8"), 1e ("ENDF10") and 1f ("ENDF11") according to the invention exerted a very strong and significant stimulatory effect on the DCX promoter activity, as also shown in FIGS. 1A and 1C, respectively. The effect was similar or even higher compared to the one exerted by the positive control retinoic acid plus valproic acid (denoted as "RA10+VPA50" in FIG. 1A). A stimulatory effect on the DCX promoter activity was also observed for compounds 1d ("ENDF9") and 2a ("ENDF5") and, to a lesser extent, for compounds 1g ("ENDF7"), 3a ("ENDF2") and 3b ("ENDF6") according to the invention, as can be seen in FIGS. 1A, 1B and 1C. The FF/R values indicated in FIGS. 1A, 1B and 1C are relative to the respective control.

The reference compounds ENDF4, tocopherol, osajin, chromanol and isoxanthohumol did not have any significant stimulatory effect on the DCX promoter activity. Actually, a 10 μM concentration of osajin induced a down-regulation of the DCX promoter (FIG. 1A).

The compounds according to the present invention, and particularly compounds 1a, 1b, 1c, 1e and 1f, as well as compounds 1d, 1g, 2a, 3a and 3b, have thus been shown to induce the activity of the neuronal precursor and neuronal differentiation specific promoter DCX, which demonstrates the suitability of the compounds according to the invention as neuroprotective agents and in promoting neuronal differentiation. Moreover, the compounds of the invention show a considerably improved efficacy in inducing the DCX promoter as compared to the reference compounds tested. The normalized renilla activity values of the substances tested (FIG. 1D) furthermore indicate that the compounds according to the invention exhibit a favorably low cytotoxicity, particularly in comparison to the reference compounds xanthohumol and osajin.

Example 18: The Chromane-Like Cyclic Prenylflavonoids According to the Invention Enhance the Percentage of Cells Expressing the Neuronal Specific Markers DCX and Map2ab in MEF Cultures Following the results from the Luciferase assay described in Example 17, the inventors examined the ability of compounds according to the invention and reference compounds to promote differentiation of MEF E16 cells, using immunocytochemical staining with DCX and Map2ab antibodies.

Compound 1a at 10 and 100 μM was analyzed for its effect on the expression of the neuronal specific markers DCX and Map2ab using primary fetal mouse brain derived cells stimulated in DMEM-KO media. Furthermore, compounds 1a ("ENDF1"), 1b ("ENDF3") and 3a ("ENDF2") according to the invention as well as the reference compounds xanthohumol, isoxanthohumol, ENDF4, 6-prenylnaringenin, 8-prenylnaringenin, chromanol and tocopherol were analyzed for their effect on the expression of the neuronal specific markers DCX and Map2ab using primary fetal mouse brain derived cells stimulated in Neurobasal plus 1% FCS media.

Mouse embryonic day 16 forebrain cells were prepared as described in Example 17. Before seeding the cells, glasscoverslips were coated and prepared. Glass-coverslips (13 mm) (Menzel GmbH, Braunschweig, Germany) were incubated in 1 M HCl at 65° C. overnight and stored in isopropanol until further use. Coverslips were put into 24-well test plates and air-dried. Subsequently coverslips were incubated for 1 h with 100 μg/ml Poly-L-ornithin solution at 37° C. After washing three times with sterile water coverslips were incubated with 5 μg/ml Laminin solution for 2 h. Immediately after removal of the Laminin solution cells were seeded (40.000 cells/well) in DMEM-KO plus supplement or in NB-B27 plus 1% FCS medium. One day later, cells had attached to the substrate. Cells were stimulated with the above-mentioned substances (in DMEM-KO plus supplement medium: 10 μM and 100 μM; in NB-B27 plus 1% FCS medium: 10 μM) for 3 or 7 days. In the 7 day group, medium including the substances was replaced after three days. Cultures were maintained at 37° C. in a humidified incubator with 5% $CO_2$.

Cells were fixed with phosphate-buffered 4% paraformaldehyde (Sigma-Aldrich, Taufkirchen, Germany). The fixed cells were washed three times in DPBS (PAA, Pasching, Austria) and subsequently blocked for a minimum of 1 hour at room temperature in fish skin gelatine buffer (FSGB) containing 0.1M Tris-HCl pH 7.5, 0.15 M NaCl, 1% bovine serum albumin, 0.2% Teleostean gelatin and 0.1% Triton X-100 (Sigma-Aldrich, Taufkirchen, Germany) to make the cell membrane permeable for the antibody. The specimens were incubated overnight at 4° C. with the primary antibodies at the following dilutions in FSGB: rabbit anti Doublecortin (DCX) 1:500 (NEB, Frankfurt, Germany) and mouse anti-Map 2a+2b 1:400 (Sigma-Aldrich, Taufkirchen, Germany). After washing three times with FSGB, cells were incubated with the species-specific secondary antibodies, which were conjugated to fluorochromes, for 2 hours in the dark at room temperature. To remove unbound secondary antibodies, cells were washed again with PBS. Nuclear counterstaining was performed with 4',6'-diamidino-2-phenylindole dihydrochloride hydrate (DAPI) at 0.25 μg/μl (Sigma Aldrich, Taufkirchen, Germany). Finally, cells were washed again three times with PBS and mounted on microscope slides using Prolong Antifade reagent (Invitrogen, Oreg., USA).

The immunostainings were examined using Olympus IX81 inverted research microscope and the software Volocity 5.3.1. To quantify the number of cells, five indiscriminately chosen visual fields per coverslip were selected under a focus of 40 times. The total number of cells (DAPI positive cells), the number of DCX positive, Map2ab positive, and DCX/Map2ab double positive cells was determined.

The results of these experiments are shown in FIGS. 2 and 3. As can be seen, compound 1a according to the invention enhances the expression of the neuronal specific markers DCX and Map2ab in primary fetal mouse brain derived cells stimulated in DMEM-KO media (FIG. 2). When primary fetal mouse brain derived cells were stimulated in Neurobasal plus 1% FCS media, compound 1a showed the most vigorous effect on DCX and Map2ab expression ($p<0.001$), while compound 1b ($p<0.01$) and ENDF4 ($p<0.01$) also strongly enhanced the number of DCX positive cells (FIG. 3A). The effect of compound 3a ($p<0.05$) was similar to that of 8-prenylnaringenin ($p<0.05$), 6-prenylnaringenin ($p<0.05$) and tocopherol ($p<0.05$) whereas ENDF4 increased slightly more the number of DCX/Map2ab double positive cells (FIG. 3B). The highest number of DCX and Map2ab double positive cells showed compounds 1a ($p<0.001$) and 1b ($p<0.001$). It has thus been demonstrated that the compounds of the present invention enhance neuronal differentiation.

Example 19: The Chromane-Like Cyclic Prenylflavonoids According to the Invention Promote Neurite Growth and Branching Further to the effects on the activation of the DCX promoter and on the percentage of neuronal cells in MEF cultures as determined in Examples 17 and 18, the effects of chromane-like cyclic prenylflavonoids, including compound 1a according to the invention, on neuronal neurite extension and branching was tested in primary MEF cells, in the neuroblastoma cell line Neuro-2a and in fetal chicken dorsal root ganglion cells (RDGs).

Effects of Chromane-Like Cyclic Prenylflavonoids on Neurite Length and Branching in MEF Cultures Mouse embryonic day 16 forebrain cells were prepared and treated as described in Example 17.

The morphology of MEF cells after a 7 day treatment with retinoic acid/valproic acid or with compound 1a (ENDF1) is illustrated in FIG. 4. Cells were fixed and stained with DCX and Map2ab antibodies as described in Example 18. Three independent experiments were performed and evaluated. Data acquisition was done by using the software Volocity 5.3.1 for measurement and photographical documentation. The following parameters were analyzed: polarity, process, number of branches, number and length of sprouts, neurite-length and growth cone morphology. At the qualitative level, compound 1a strongly increases neurite length and neurite branching (FIG. 4).

For quantitative analysis of neurite length, neurons with long neurites were taken into consideration. MEF cells stimulated with 10 µM and 100 µM compound 1a (ENDF1) displayed much longer neurites compared to control or retinoic acid/valproic acid treated MEF cells, as also shown in FIG. 4I. For quantitative analysis of neurite branching, the branch density (number of branches per 100 µm of neurite length) was counted. For analysis, the DCX staining with DMEM-KO medium was used, since DCX, in contrast to Map2ab, is localized throughout the neurites. MEF cells stimulated with 10 µM and 100 µM compound 1a (ENDF1) displayed a dramatic increase in branching/sprouting compared to control or retinoic acid/valproic acid treated MEF cells, as shown in FIG. 4J.

Effects of Chromane-Like Cyclic Prenylflavonoids on Neurite Length in Neuro2a Cells For more precise analysis of neurite length Neuro2a cells were selected and stimulated for 2 days with RA/VPA as positive control and ENDFs in MEM+10% FCS. Immunocytochemical analysis was performed using GAP43 antibody which is known as a strong neuronal plasticity marker.

Neuro2a cells were grown in MEM with Earle's Salts (PAA, Pasching, Austria) containing 2 mM L-glutamine, 100 µg/ml Penicillin/Streptomycin (PAN Biotech GmbH, Aidenbach, Germany), 100 mM sodium pyruvate (Sigma-Aldrich, Taufkirchen, Germany) and 10% FCS (Lonza, Wuppertal, Germany).

The cells were passaged with 6 ml trypsin 0.5 mg/ml+ EDTA 0.22 mg/ml (PAA, Pasching, Austria) two times per week. For analysis of neurite length Neuro2a cells were seeded on coverslips in a 24 well plate coated with Poly-L-ornithine and Laminin in a differentiation media MEM with Earle's Salts (PAA, Pasching, Austria) containing 2 mM L-glutamine, 100 µg/ml Penicillin/Streptomycin (PAN Biotech GmbH, Aidenbach, Germany), 100 mM sodium pyruvate (Sigma-Aldrich, Taufkirchen, Germany) and 1% FCS (Lonza, Wuppertal, Germany) and treated for 2 days with retinoic acid plus valproic acid and compound 1a (ENDF1) 10 µM, compound 1b (ENDF3) 10 µM, compound 3a (ENDF2) 10 µM, or ENDF4 10 µM. Cells were fixed as described in Example 18. Immunostaining was performed using GAP-43 1:500 (AbD Serotec, Oxford, UK).

Neuro2a cells stimulated with compound 1a (ENDF1) and compound 1b (ENDF3) 10 µM display a strong and significant increase on neurite length and more elaborated branches as compared to control and RAA/PA treated cells, which is also shown in FIG. 5. Compound 3a (ENDF2) shows more sprouting than the other substances.

Effects of Chromane-Like Cyclic Prenylflavonoids on Neurite Length in Primary Chicken DRG Neurons Dorsal root ganglion neurons comprise of an axon with two branches and are a good model for neuronal differentiation. Embryonic day 8 and 15 chicken dorsal root ganglions were examined for immunochemical staining with GAP43 after incubation with NGF 20 ng/ml and compound 1a (ENDF1) 10 µM to analyze whether compound 1a alone or in combination with the nerve growth factor enhances neurite outgrowth and branching.

Embryonic day (E) 8 and E15 chicken Dorsal Root Ganglions (DRGs) were prepared as described in: Aigner, 1993; Aigner, 1995. Briefly, foetuses were taken out of the egg, decapitated and the DRGs were targeted from the ventral side. The 10 lumbar region DRGs per foetus were dissected, and a total of 100 DRGs were collected in 10 ml DPBS in a 15 ml Falcon tube. DRGs were centrifuged 120×g for 3 min and then enzymatically treated with 1 ml trypsin 0.5 mg/ml+EDTA 0.22 mg/ml (PAA, Pasching, Austria) for 15 min. Then, 9 ml of DMEM 10% FCS were added to inactivate the trypsin and DRGs were centrifuged 120×g for 5 min. DRGs were resuspended and washed with 5 ml of DMEM 10% FCS, pipetted up and down to dissociate them, centrifuged, resuspended in 5 ml of DMEM 10% FCS and transferred into a 60 mm diameter cell culture dish. This cell culture dish with the DRGs were placed into a humidified incubator with 5% $CO_2$ and 37° C. for three hours to allow non-neuronal cells to adhere to the bottom of the dish, while DRG neurons remained non-adherent. After three hours of incubation, the non-adherent fraction was collected, centrifuged 5 min at 120×g and resuspended in 700 µl of DMEM 10% FCS. 20 µl of cell suspension were transferred into each well of a 24 well plate, in which a Poly-L-ornithine/Laminin coated glass coverslip and 400 µl of DMEM 10% FCS with the different compounds (compound 1a and/or NGF) were prepared. Cultures were maintained at 37° C. in a humidified incubator (Heraeus, Germany) with 5% $CO_2$ for 24 hours.

Cells were fixed with phosphate-buffered 4% paraformaldehyde (Sigma-Aldrich, Taufkirchen, Germany). The fixed cells were washed three times in DPBS (PAA, Pasching, Austria) and subsequently blocked for a minimum of 1 hour at room temperature in fish skin gelatine buffer (FSGB) containing 0.1 M Tris-HCl pH 7.5, 0.15 M NaCl, 1% bovine serum albumin, 0.2% Teleostean gelatin and 0.1% Triton X-100 (Sigma-Aldrich, Taufkirchen, Germany) to make the cell membrane permeable for the antibody. The specimens were incubated overnight at 4° C. with primary antibody rabbit anti GAP-43 1:500 (AbD Serotec, Oxford, UK). After washing three times with FSGB, cells were incubated with the species-specific secondary antibody, which was conjugated to fluorochromes, for 2 hours in the dark at room temperature. To remove unbound secondary antibodies, cells were washed again with PBS. Nuclear counterstaining was performed with 4',6'-diamidino-2-phenylindole dihydrochloride hydrate (DAPI) at 0.25 µg/µl (Sigma Aldrich, Taufkirchen, Germany). Finally, cells were washed again three times with PBS and mounted on microscope slides using Prolong Antifade reagent (Invitrogen, Oreg., USA). The immunostainings were examined using Olympus IX81 inverted research microscope and the software Volocity 5.3.1.

The results are indicated in FIG. 6 and show NGF as a potent enhancer of neuronal differentiation by increasing neurite growth and branching. Interestingly, compound 1a (ENDF1) was almost in the range of NGF and in combination (ENDF1+NGF) there was a slight but significant increase compared to NGF alone.

In view of the above, it has been demonstrated that the compounds of the present invention, including compound 1a, promote neuronal differentiation and enhance neurite outgrowth and sprouting, e.g., in MEF cultures, Neuro2a cells and chicken dorsal root ganglions. Moreover, it has been found that the compounds of formula (III) according to the invention, including compound 3a, are particularly advantageous with respect to the promotion of neurite sprouting.

Example 20: The Chromane-Like Cyclic Prenylflavonoids According to the Invention are Neuroprotective For the neuroprotection assay PC12 cells were stressed with cobalt chloride 300 µM for 24 hours and the activity of Caspase 3/7 and LDH release were measured. NGF 50 ng/ml was used as a positive control for Caspase 3/7 activity and NGF 100 ng/ml was used as a positive control for LDH release.

For the PC12-$CoCl_2$-Assay PC12 cells were used (ATCC: CRL-1721 ™). These cells were growing in RPMI supplemented with 10% Horse Serum (heat inactivated) (Sigma Aldrich, Taufkirchen, Germany), 5% Fetal Bovine Serum (Lonza, Wuppertal, Germany), 2.5% Penicillin/Streptomycin and Glutamine (PAA, Pasching, Austria) as adherent cultures when the plates are coated with Poly-L-ornithine (100 mg/ml in water) for at least one hour at 37° C. For passaging PC12-cells were resuspended with Accutase (PAA, Pasching, Austria) for 10 minutes at 37° C. once a week.

For all experiments cells were plated (quadruplicates) on Poly-L-ornithine-coated 96-well plates at a density of 104 cells per well. For Caspase 3/7-measurement cells were seeded in a white 96-well-plate to detect luminescence. As positive-control for neuroprotection Nerve Growth Factor (NGF) (50 ng/ml and 100 ng/ml) was used. To induce hypoxia $CoCl_2$ (300 µM) was added to the cells after 20-24 hours. The control-treatment was compound 1a (ENDF1), compound 1b (ENDF3), compound 3a (ENDF2), ENDF4 or Osajin in the concentrations 1 µM and 10 µM in proliferation-media without $CoCl_2$.

For Caspase 3/7-activation Caspase 3/7 substrate was added to the cells in an equal amount 22 hours after stimulation. Plates are incubated for 2 hours at room temperature in the dark, luminescence was measured 24 hours after stimulation and the blank-values are subtracted.

For LDH-release cells were centrifuged at 1050 rpm for 5 minutes. After 24 hours of stimulation, the supernatant was mixed in an equal amount with LDH-substrate and incubated in the dark for 30 minutes. Afterwards stop solution was added and absorbance was measured at 490 nm, the blank-values are subtracted.

The results shown in FIG. 7A confirm that $CoCl_2$ induces stress in PC12 cells whereas NGF inhibits $CoCl_2$ induced Caspase 3/7 activity. Compounds 1a (ENDF1) and 1b (ENDF3) 10 µM display a significant neuroprotective effect similar to NGF.

The results of the LDH release assay (FIG. 7B) show that NGF 100 ng/ml as well as compound 1a (ENDF1), compound 1b (ENDF3) and compound 3a (ENDF2) 10 µM slightly decrease the LDH release whereas Osajin does not significantly diminish cell death.

These results indicate that the compounds of the present invention, including compounds 1a, 1 b and 3a, are neuroprotective, as has been demonstrated in PC12 cells.

LITERATURE

Brattström A. (2007): Scientific evidence for a fixed extract combination (Ze 91019) from valerian and hops traditionally used as a sleep-inducing aid. Wen Med Wochenschr 157(13-14), 367-70.

Brunelli E., Minassi A., Appendino G. and Moro L. (2007): 8-Prenylnaringenin inhibits estrogen receptor-α mediated cell growth and induces apoptosis in MCF-7 breast cancer cells. The Journal of Steroid Biochemistry and Molecular Biology 107, (3-5), 140-148.

Dajas F., Rivera-Megret F., Blasina F., Arredondo F., Abin-Carriquiry J. A., Costa G., Echeverry C., Lafon L., Heizen H., Ferreira M. and Morquio A. (2003): Neuroprotection by flavonoids. Braz J Med Biol Res 36(12), 1613-20.

Goto K., Asai T., Hara S., Namatame I., Tomoda H., Ikemoto M. and Oku N. (2005): Enhanced antitumor activity of xanthohumol, a diacylglycerol acyltransferase inhibitor, under hypoxia. Cancer Letters 219, 215-222.

Gutierrez-Merino C., Lopez-Sanchez C., Lagoa R., Samhan-Arias A. K., Bueno C. and Garcia-Martinez V. (2011): Neuroprotective actions of flavonoids. Curr Med Chem 18(8), 1195-212.

Liu R. T., Zou L. B., Fu J. Y. and Lu Q. J. (2009): Promotion of rat brain-derived progenitor cell neurogenesis by liquiritigenin treatment: Underlying mechanisms. Neuroscience Letters 481 (3), 139-143.

Ramon y Cajal S. (1913): Degeneration and Regeneration of the Nervous System. London: Oxford Univ. Press.

Valente T., Hidalgo J., Bolea I., Ramirez B., Angl es N., Reguant J., Morell o J. R., Guti errez C., Boada M. and Unzeta M. (2009): A diet enriched in polyphenols and polyunsaturated fatty acids, LMN diet, induces neurogenesis in the subventricular zone and hippocampus of adult mouse brain. Journal of Alzheimer's disease 18, 849-865.

The invention claimed is:

1. A method of treating a neurological disorder selected from the group consisting of a spinal cord injury and a peripheral nerves injury, the method comprising the administration of a compound of the following formula (I) or a pharmaceutically acceptable salt or solvate of said compound to a subject in need of such a treatment,

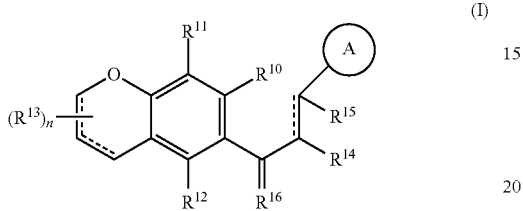

wherein:
A is aryl or heteroaryl, wherein said aryl or said heteroaryl is optionally substituted with one or more groups independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN;

$R^{10}$ is —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), hydrogen, or $C_{1-6}$ alkyl;

$R^{11}$ and $R^{12}$ are each independently selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN;

each $R^{13}$ is independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN;

$R^{14}$ and $R^{15}$ are each independently selected from hydrogen, $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO—$C_{1-6}$ alkyl, —O—CO-phenyl, —O—CO—($C_{1-6}$ alkylene)-phenyl, —O—CO—O($C_{1-6}$ alkyl), —CO—$C_{1-6}$ alkyl, —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl)($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl)($C_{1-6}$ alkyl), —N($C_{1-6}$ alkyl)-CO—N($C_{1-6}$ alkyl)($C_{1-6}$ alkyl), halogen, —CF$_3$, or —CN;

$R^{16}$ is O, S or N(—OH);

n is 0, 1, 2 or 3; and each ═══ in formula (I) is independently a single bond or a double bond, provided that at least one of the two adjacent bonds ═══ is a single bond.

2. The method of claim 1, wherein said compound is a compound of formula (I) or a pharmaceutically acceptable salt or solvate thereof, wherein A is phenyl which is optionally substituted with one or more groups independently selected from $C_{1-6}$ alkyl, $C_{2-6}$ alkenyl, $C_{2-6}$ alkynyl, —OH, —O($C_{1-6}$ alkyl), —SH, —S($C_{1-6}$ alkyl), —NH$_2$, —NH($C_{1-6}$ alkyl), —N($C_{1-6}$ alkyl)($C_{1-6}$ alkyl), —O—CO-phenyl, —O—CO—($C_{1-6}$ alkylene)-phenyl, —O—CO—O($C_{1-6}$ alkyl), —CO—$C_{1-6}$ alkyl, —COOH, —CO—O($C_{1-6}$ alkyl), —CO—NH$_2$, —CO—NH—($C_{1-6}$ alkyl), —CO—N($C_{1-6}$ alkyl)($C_{1-6}$ alkyl), —O—CO—NH$_2$, —O—CO—NH—($C_{1-6}$ alkyl), —O—CO—N($C_{1-6}$ alkyl) ($C_{1-6}$ alkyl), —NH—CO—($C_{1-6}$ alkyl), —N($C_{1-6}$ alkyl)-CO—($C_{1-6}$ alkyl), —NH—CO—O($C_{1-6}$ alkyl), —N($C_{1-6}$ alkyl)-CO—O($C_{1-6}$ alkyl), —NH—CO—NH$_2$, —N($C_{1-6}$ alkyl)-CO—NH$_2$, —NH—CO—NH($C_{1-6}$ alkyl), —N($C_{1-6}$ alkyl)-CO—NH($C_{1-6}$ alkyl), —NH—CO—N($C_{1-6}$ alkyl) ($C_{1-6}$ alkyl), —N($C_{1-6}$ alkyl)-CO—N($C_{1-6}$ alkyl)($C_{1-6}$ alkyl), halogen, —CF$_3$, or —CN.

3. The method of claim 1, wherein said compound is a compound of formula (I) or a pharmaceutically acceptable salt or solvate thereof, wherein A is phenyl which is optionally substituted with one group selected from $C_{1-6}$ alkyl, —OH, —O($C_{1-6}$ alkyl), or halogen.

4. The method of claim 1, wherein said compound is a compound of formula (I) or a pharmaceutically acceptable salt or solvate thereof, wherein $R^{10}$ is —OH, or —O($C_{1-6}$ alkyl).

5. The method of claim 1, wherein said compound is a compound of formula (I) or a pharmaceutically acceptable salt or solvate thereof, wherein $R^{10}$ is —OCH$_3$.

6. The method of claim 1, wherein said compound is a compound of formula (I) or a pharmaceutically acceptable salt or solvate thereof, wherein $R^{11}$ and $R^{12}$ are each independently selected from hydrogen, $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN.

7. The method of claim 1, wherein said compound is a compound of formula (I) or a pharmaceutically acceptable salt or solvate thereof, wherein each $R^{13}$ is independently selected from $C_{1-6}$ alkyl, —OH, —O($C_{1-6}$ alkyl), —NH$_2$, —NH($C_{1-6}$ alkyl), —N($C_{1-6}$ alkyl)($C_{1-6}$ alkyl), halogen, —CF$_3$, or —CN.

8. The method of claim 1, wherein said compound is a compound of formula (I) or a pharmaceutically acceptable salt or solvate thereof, wherein $R^{14}$ and $R^{15}$ are each independently selected from hydrogen, $C_{1-6}$ alkyl, —OH, —O($C_{1-6}$ alkyl), or halogen.

9. The method of claim 1, wherein said compound is a compound of formula (I) or a pharmaceutically acceptable salt or solvate thereof, wherein n is 0.

10. The method of claim 1, wherein said compound is a compound of formula (I) or a pharmaceutically acceptable salt or solvate thereof, wherein n is 2 and each $R^{13}$ is independently selected from hydrogen, $C_{1-6}$ alkyl, —OH, —O($C_{1-6}$ alkyl), or halogen.

11. The method of claim 1, wherein said compound is a compound of formula (I) or a pharmaceutically acceptable salt or solvate thereof, wherein $R^{16}$ is O.

12. The method of claim 1, wherein said compound is a compound of formula (I) or a pharmaceutically acceptable salt or solvate thereof, wherein each ==== in formula (I) is a single bond.

13. The method of claim 1, wherein said compound is a compound of formula (I) or a pharmaceutically acceptable salt or solvate thereof, wherein one of the two adjacent bonds ==== in formula (I) is a single bond and each one of the other two bonds ==== in formula (I) is a double bond.

14. The method of claim 1, wherein said compound is a compound of the following formula 1a, 1b, 1c, 1d, 1e, 1f, or 1g

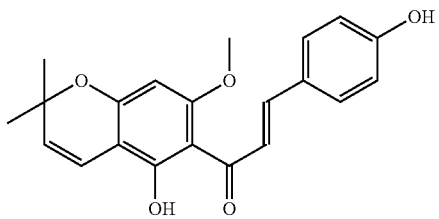

1a

-continued

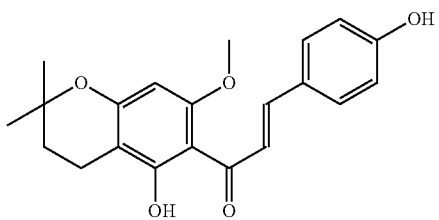

1b

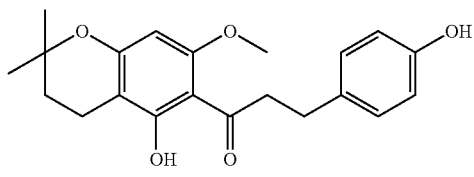

1c

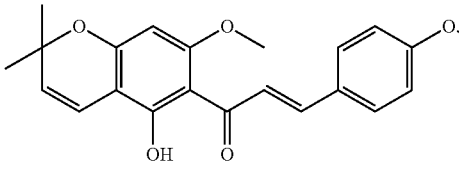

1d

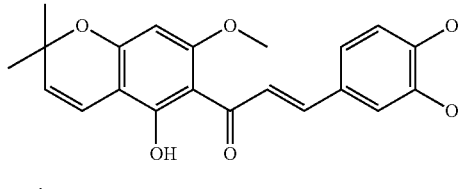

1e

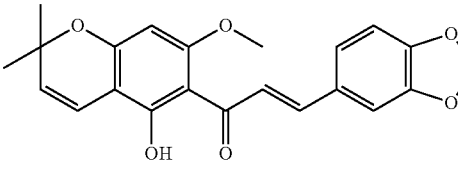

1f

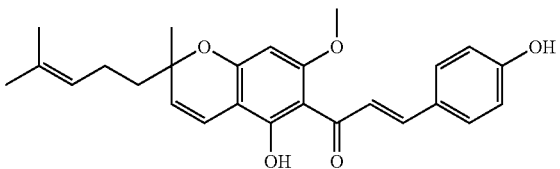

1g or a pharmaceutically acceptable salt or solvate thereof.

15. The method of claim 1, wherein said subject is a human.

16. The method of claim 1, wherein the neurological disorder is a spinal cord injury.

17. The method of claim 1, wherein the neurological disorder is a peripheral nerves injury.

* * * * *

UNITED STATES PATENT AND TRADEMARK OFFICE
CERTIFICATE OF CORRECTION

PATENT NO. : 9,956,199 B2  
APPLICATION NO. : 15/354325  
DATED : May 1, 2018  
INVENTOR(S) : Ludwig Aigner et al.

Page 1 of 1

It is certified that error appears in the above-identified patent and that said Letters Patent is hereby corrected as shown below:

On the Title Page

Item (72) Inventors, Line 5, country of residence for Francisco Javier Rivera, delete "(AT)" and insert --(CL)-- therefor.

Signed and Sealed this  
Fourteenth Day of August, 2018

Andrei Iancu  
*Director of the United States Patent and Trademark Office*